US012594250B2

(12) United States Patent
Swanson

(10) Patent No.: US 12,594,250 B2
(45) Date of Patent: Apr. 7, 2026

(54) PREVENTION OF ACCUMULATED TOLERANCE TO STIMULANT MEDICATION FOR THE TREATMENT OF ADHD

(71) Applicant: James Martin Swanson, Seattle, WA (US)

(72) Inventor: James Martin Swanson, Seattle, WA (US)

( * ) Notice: Subject to any disclaimer, the term of this patent is extended or adjusted under 35 U.S.C. 154(b) by 0 days.

(21) Appl. No.: 19/176,038

(22) Filed: Apr. 10, 2025

(65) Prior Publication Data

US 2025/0255836 A1      Aug. 14, 2025

Related U.S. Application Data

(62) Division of application No. 17/716,932, filed on Apr. 8, 2022, now abandoned.

(60) Provisional application No. 63/201,057, filed on Apr. 9, 2021.

(51) Int. Cl.

| | |
|---|---|
| *A61K 31/137* | (2006.01) |
| *A61K 9/48* | (2006.01) |
| *A61K 31/135* | (2006.01) |
| *A61K 31/138* | (2006.01) |
| *A61K 31/16* | (2006.01) |
| *A61K 31/165* | (2006.01) |
| *A61K 31/407* | (2006.01) |
| *A61K 31/4168* | (2006.01) |
| *A61K 31/4458* | (2006.01) |
| *A61K 31/5375* | (2006.01) |
| *A61K 31/55* | (2006.01) |

(52) U.S. Cl.
CPC .......... *A61K 31/137* (2013.01); *A61K 9/4808* (2013.01); *A61K 31/135* (2013.01); *A61K 31/138* (2013.01); *A61K 31/16* (2013.01); *A61K 31/165* (2013.01); *A61K 31/407* (2013.01); *A61K 31/4168* (2013.01); *A61K 31/4458* (2013.01); *A61K 31/5375* (2013.01); *A61K 31/55* (2013.01)

(58) Field of Classification Search
CPC ......... A61K 31/137; A61P 25/00; A61P 25/26
See application file for complete search history.

(56) References Cited

U.S. PATENT DOCUMENTS

| | | | | |
|---|---|---|---|---|
| 6,217,904 B1 * | 4/2001 | Midha | ..................... | A61P 25/22 |
| | | | | 424/490 |
| 2011/0262496 A1 * | 10/2011 | Desai | ..................... | A61P 25/00 |
| | | | | 564/381 |

OTHER PUBLICATIONS

Abikoff, et al., "The normalizing effects of methylphenidate on the classroom behavior of ADDH children," J. Abnorm. Child Psychol., 1985, 13(1): 33-44.

Ahmed, et al., "An update on medication adherence and persistence in children, adolescents, and adults." Expert Review Pharmacoeconomics Outcome Research, 2013, 13(6): 791-815.

Arnold, et al., "National Institute of Mental Health collaborative multimodal treatment study of children with ADHD (the MTA): Design Challenges and Choices," Arch. Gen. Psychiatry, 1997, 54:865-870.

Arnold, et al., "Effect of treatment modality on long-term outcomes in attention-deficit/hyperactivity disorder: A systematic review." PLOS One, 2015, 10: 1-19.

Atzori, et al., "Predictive factors for persistent use and compliance of immediate-release methylphenidate: a 36-month naturalistic study." Journal of child and adolescent psychopharmacology, 2009, 19(6): 673-681.

Barkley, et al., "The Adverse Health Outcomes, Economic Burden, and Public Health Implications of Unmanaged Attention Deficit Hyperactivity Disorder (ADHD): A Call to Action to Improve the Quality of Life and Life Expectancy of People with ADHD," ADHD Public Health Summit, 2020; Washington DC, pp. 1-22.

Bhat, et al., "Considerations for selecting treatments for attention deficit hyperactivity disorder," Clinical Pharmacist, 2016, 8(2): 1-24.

Biederman, et al., "A randomized, 3-phase, 34-week, double-blind, long-term efficacy study of osmotic-release oral system-methylphenidate in adults with attention-deficit/hyperactivity disorder." Journal of clinical psychopharmacology, 2010, 30(5): 549-553.

Biederman, et al., "Evidence of low adherence to stimulant medication among children and youths with ADHD: An Electronic Health Records Study," Psychiatric Services, 2019, 70(10): 874-880.

Bradley, C., "Benzedrine and dexedrine in the treatment of children's behavior disorders." Pediatrics, 1950, 5(1): 24-37.

Brinkman, et al., "Reasons why children and adolescents with ADHD stop and restart taking medicine." Academic pediatrics, 2018, 18(3): 273-280.

Buitelaar et al., "Long-term efficacy and safety outcomes with OROS-MPH in adults with ADHD", International Journal of Neuropsychopharmacology, 2012, 15:1-13.

Charach, et al. "Stimulant treatment over five years: Adherence, effectiveness, and adverse effects," Journal of the American Academy of Child and Adolescent Psychiatry, 2004; 43: 559-567.

Charach, et al., "Enhancing ADHD Medication Adherence: Challenges and Opportunities," Curr. Psychiatry Reports, 2013; 15(371): 1-8.

(Continued)

*Primary Examiner* — Micah Paul Young

(74) *Attorney, Agent, or Firm* — Knobbe, Martens, Olson & Bear, LLP

(57) ABSTRACT

It is proposed that dissipation of relative benefit during long-term treatment is due to long-term tolerance to stimulant medications. To improve adherence and persistence of medication use, it is advantageous to develop medications that are not undermined by long-term tolerance. Disclosed herein in certain implementations are methods for the prevention of accumulated tolerance to stimulant medication for the treatment of ADHD based on two principles: (a) retaining the initial immediate-release component of controlled-release formulations, and (b) replacing the subsequent sustained-release component (i.e., an ascending delivery of stimulant medication to counteract acute tolerance) with a controlled-release component designed to prevent carry-over effects on background tonic dopamine.

16 Claims, 6 Drawing Sheets

(56) References Cited

OTHER PUBLICATIONS

Coghill, et al., "Effective management of attention-deficit/ hyperactivity disorder (ADHD) through structured re-assessment: the Dundee ADHD Clinical Care Pathway." Child and adolescent psychiatry and mental health, 2015, 9(52): 1-15.

Coghill, et al., "The management of ADHD in children and adolescents: bringing evidence to the clinic: perspective from the European ADHD Guidelines Group (EAGG)." European Child & Adolescent Psychiatry, 2021, in 25 pages.

Cortese, et al., "Comparative efficacy and tolerability of medications for attention-deficit hyperactivity disorder in children, adolescents, and adults: asystematic review and network meta-analysis," Lancet Psychiatry, 2018, 5: 727-738.

Cortese, et al., "Debate: Are Stimulant Medications for Attention-Deficit/Hyperactivity Disorder Effective in the Long Term?" Journal of the American Academy of Child and Adolescent Psychiatry, 2019, 58(10): 936-939.

Diagnostic and Statistical Manual (DSM), Edition II, American Psychiatric Association, 1968, Washington DC.

Diagnostic and Statistical Manual (DSM), Edition III, American Psychiatric Association, 1980, Washington DC.

Diagnostic and Statistical Manual (DSM), Edition IV, American Psychiatric Association, 1994, Washington DC.

Diagnostic and Statistical Manual (DSM), Edition V, American Psychiatric Association, 2013, Washington DC.

Faraone, et al., "The world federation of ADHD international consensus statement: 208 evidence-based conclusions about the disorder," Neuroscience & Biobehavioral Reviews, 2021, 128: 789-818.

Gajria, et al., "Adherence, persistence, and medication discontinuation in patients with attention-deficit/hyperactivity disorder—a systematic literature review", Neuropsych. Disease and Treatment, 2014, 10: 1543-1569.

Gill, et al., "The effects of rearing environment and chronic methylphenidate administration on behavior and dopamine receptors in adolescent rats." Brain Research, 2013, 1527: 67-78.

Goto, et al., "The Yin and Yang of dopamine release: a new perspective." Neuropharmacology, 2007, 53(5): 583-587.

Grace, A.A., "The tonic/phasic model of dopamine system regulation and its implications for understanding alcohol and psychostimulant craving." Addiction, 2000, 95(2): S119-S128.

Grace, A.A., "Psychostimulant actions on dopamine and limbic system function: Relevance to the pathophysiology and treatment of ADHD." Stimulant Drugs and ADHD: Basic and Clinical Neuroscience, 2001, in 26 pages.

Grace, A.A., "Dopamine," In Neuropsychopharmacology: the fifth Generation of Progress, 2002, pp. 119-132.

Grace, et al., "The circuitry of dopamine system regulation and its disruption in schizophrenia: insights into treatment and prevention." Schizophrenia bulletin, 2019, 45(1): 148-157.

Greenhill, et al., "Methylphenidate in the clinical office practice of child psychiatry." Ritalin: Theory and patient management, 1991, pp. 97-117.

Greenhill, et al., "Ritalin: Theory and Management," 1991; Mary Ann Liebert: New York City: NY.

Greenhill, et al., "Impairment and deportment responses to different methylphenidate doses in children with ADHD: the MTA titration trial", J. Am. Acad. Child Adolesc. Psychiatry, 2001; 40(2): 180-187.

Greenhill, et al., "A pharmacokinetic/pharmacodynamic study comparing a single morning dose of Adderall to twice-daily dosing in children with ADHD," J. Am. Acad. Child Adolesc. Psychiatry, 2003; 42:1234-1241.

Greenhill, et al., "Efficacy and safety of immediate-release methylphenidate treatment for preschoolers with ADHD." Journal of the American Academy of Child & Adolescent Psychiatry, 2006, 45(11): 1284-1293.

Hechtman, et al., "Functional adult outcomes 16 years after childhood diagnosis of attention-deficit/hyperactivity disorder: MTA results," 2016, Journal of the American Academy of Child and Adolescent Psychiatry, 2016, 55(11): 945-952.

Individuals with Disabilities Education Act. US Congress: Reauthorization of the Education for All Handicapped Children Act (Public Law 94-142), Wikipedia.

Internation Classification of Diseases (ICD), Version 9, World Health Organization, 1979, Geneva.

Internation Classification of Diseases (ICD), Version 10, World Health Organization, 1992, Geneva.

Internation Classification of Diseases (ICD), Version 11, World Health Organization, 2019, Geneva.

Jensen, et al., "3-year follow-up of the NIMH MTA study," J. Am. Acad. Child Adolesc. Psychiatry, 2007, 46(8): 989-1002.

Lam, et al., "Long-term effects of multimodal treatment on adult attention-deficit/hyperactivity disorder symptoms: follow-up analysis of the COMPAS trial." JAMA network open, 2019, 2(5): 1-17.

Lawson, et al., "Utilization Patterns of Stimulants in ADHD in the Medicaid Population," Clinical Therapeutics, 2012; 34: 944-956.

Marcus, et al., "Stimulant adherence and academic performance in urban youth with attention-deficit/hyperactivity disorder," Journal of the American Academy of Child and Adolescent, Psychiatry, 2011; 50(5): 480-489.

Matthijssen, et al., "Continued benefits of methylphenidate in ADHD after 2 years in clinical practice: a randomized placebo-controlled discontinuation study." American Journal of Psychiatry, 2019, 176(9): 754-762.

Mattingly, et al., "Individualization of attention-deficit/ hyperactivity disorder treatment: pharmacotherapy considerations by age and co-occurring conditions," CNS Spectrums, 2021, 26(3): 202-221.

McCracken, et al., "Analog classroom assessment of a once-daily mixed amphetamine formulation, SLI381 (Adderall XR), in children with Adhd", J. Am. Acad. Child Adolesc. Psychiatry, 2003, 42(6): 673-683.

McGough, et al., "Pharmacokinetics of SLI381 (Adderall XR), an extended-release formulation of Adderall," J. Am. Acad. Child Adolesc. Psychiat., 2003, 42(6): 684-691.

Miller, et al., "Children's persistence with methylphenidate therapy: A population-based study," Canadian Journal of Psychiatry, 2004; 49(11): 761-768.

Molina, et al., "Delinquent behavior and emerging substance use in the MTA at 36 months: prevalence, course, and treatment effects," J. Am. Acad. Child Adolesc. Psychiatry, 2007, 46(8): 1027-1039.

Molina, et al., "The MTA at 8 years: Prospective follow-up of children treated for combined-type ADHD in a multisite study," J. Am. Acad. Child Adolesc. Psychiatry, 2009, 48(5): 484-500.

Molina, et al., "Adolescent substance use in the Multimodal Treatment Study of ADHD (MTA) as a function of childhood ADHD, random assignment to childhood treatments, and subsequent medication." J. Am. Acad. Child Adolesc. Psychiatry, 2013, 52: 250-263.

Molina, et al., "Why Are Long-term Benefits of Stimulant Medication So Difficult to Detect?" The ADHD Report, 2020, 28: 1-7.

MTA Cooperative Group. A 14-month randomized clinical trial of treatment strategies for attention deficit hyperactivity disorder. Arch Gen Psychiatry, 1999, 56:1073-1086.

MTA Cooperative Group. Moderators and mediators of treatment response for children with attention-deficit/hyperactivity disorder. Arch Gen Psychiatry. 1999; 56: 1088-1096.

MTA Cooperative Group: National Institute of Mental Health Multimodal Treatment Study of ADHD follow-up: changes in effectiveness and growth after the end of treatment. Pediatrics, 2004, 113(4): 762-769.

National Institute on Clinical Excellence. NICE guideline: 2018 (Update on Mar. 14, 2018), in 61 pages, www.nice.org.uk/guidance/ng87.

National Research Council, Research on Children and Adolescents with Mental, Behavioral, and Developmental Disorders: Mobilizing a National Initiative. 1989, Washington, DC: The National Academies Press.

US 12,594,250 B2

Page 3

(56) References Cited

OTHER PUBLICATIONS

Pelham, et al., "Pemoline effects on children with ADHD: a time-response by dose-response analysis on classroom measures." Journal of the American Academy of Child & Adolescent Psychiatry, 1995, 34(11): 1504-1513.
Philipsen, et al., "Effects of group psychotherapy, individual counseling, methylphenidate, and placebo in the treatment of adult attention-deficit/hyperactivity disorder: a randomized clinical trial." JAMA psychiatry, 2015, 72(12): 1199-1210.
Pliszka, S. and AACAP Workgroup, "Practice Parameter for the Assessment and Treatment of Children and Adolescents with Attention-Deficit/Hyperactivity Disorder," J. Am. Acad. Child Adolesc. Psychiatry, 2007, 46(7): 894-921.
Polanczyk, et al., "ADHD prevalence estimates across three decades: an updated systematic review and meta-regression analysis," Int. J. Epidemiol., 2014, 43: 434-442.
Pozzi, et al., "Emerging drugs for the treatment of attention-deficit hyperactivity disorder (ADHD)." Expert Opinion on Emerging Drugs 2020, 25(4): 395-407.
Raman, et al., "Trends in attention-deficit hyperactivity disorder medication use: a retrospective observational study using population-based databases", Lancet Psychiatry. 2019; 5: 824-835.
Request for Application (RF) MH9203 MH-92-03 P101, Cooperative Agreement for a multi-site treatment study of ADHD Disorder, NIH Guide, 1992, 21(9): 1-25.
Safer, et al., "Hyperactive Children: Diagnosis and Management," 1976, University Park Press, Baltimore.
Safer, et al. "Absence of tolerance to the behavioral effects of methylphenidate in hyperactive and inattentive children," Journal of Pediatrics, 1989, 115: 1003-1008.
Shaw, et al., "A systematic review and analysis of long-term outcomes in attention deficit hyperactivity disorder: effects of treatment and non-treatment." BMC medicine, 2012, 10(99): 1-15.
Sibley, et al., "Defining ADHD symptom persistence in adulthood: optimizing sensitivity and specificity," Journal of Child Psychology and Psychiatry, 2016, pp. 1-8.
Solanto, M.V., "Clinical psychopharmacology of AD/HD: Implications for animal models," Neuroscience & Biobehavioral Reviews, 2000, 24(1): 27-30.
Solanto, et al., Stimulant Drugs and ADHD: Basic and Clinical Neuroscience, Oxford University Press, 2001.
Stanford et al., New Discoveries in the Behavioral Neuroscience of Attention-Deficit Hyperactivity Disorder, Springer, 2022.
Storebo, et al., "Methylphenidate for children and adolescents with attention deficit hyperactivity disorder (ADHD) (Review)," Cochrane Library Review. 2015; 11: 1-766.
Strohl, M.P., "Bradley's Benzedrine Studies on Children with Behavioral Disorders," Yale Journal of Biology and Medicine, 2011, 84: 27-33.
Swanson et al., "Should you use stimulants to treat the hyperactive child?", Modern Medicine, 1978, pp. 71-80.
Swanson et al., "Time-response analysis of the effect of stimulant medication on the learning ability of children referred for hyperactivity", Pediatrics, 1978, 61(1): 21-29.
Swanson, et al., "Methylphenidate hydrochloride given with or before breakfast: I. Behavioral, cognitive, and electrophysiologic effects", Pediatrics. 1983, 72(1) :49-55. (Presented in 1984 at AACAP meeting).
Swanson, et al., "Effects of stimulant medication on learning in children with ADHD." Journal of Learning Disabilities, 1991, 24(4): 219-230.
Swanson, et al., "Effect of stimulant medication on children with attention deficit disorder: A Review of Reviews," Exceptional Children, 1993, 60(2): 154-162.
Swanson, et al., "More frequent diagnosis of attention deficit-hyperactivity disorder," New England Journal of Medicine, 1995, 333(14): 944.
Swanson et al., "Analog classroom assessment of Adderall in children with ADHD," J. Am. Acad. Child Adolesc. Psychiatry, 1998; 37(5): 519-526.

Swanson, et al., "Acute tolerance to methylphenidate in the treatment of attention deficit hyperactivity disorder in children," Clin. Pharmacol. Ther., 1999, 66(3): 295-305.
Swanson, et al., "Initiating Concerta (OROS methyphenidate HC1) qd in children with attention-deficit hyperactivity disorder," J. Clinical Research, 2000, 3: 59-76.
Swanson, et al., "Pharmacokinetic and pharmacodynamic properties of stimulants: implications for the design of new treatments for ADHD," Behav. Brain Res., 2002; 130: 73-78.
Swanson, et al., "The use of a laboratory school protocol to evaluate concepts about efficacy and side effects of new formulations of stimulant medications," J. Atten. Disord., 2002, 6: S77-S92.
Swanson, et al., "Development of a new once-a-day formulation of methylphenidate for the treatment of Attention-deficit/Hyperactivity Disorder: Proof-of-concept and proof-of-product studies", Arc. Gen. Psy., 2003, 60: 204-211.
Swanson, et al. "Serum and brain concentrations of methylphenidate: implications for use and abuse." Neuroscience and Biobehavioral Reviews, 2003, 27: 615-621.
Swanson, et al., "A comparison of once-daily extended-release methylphenidate formulations in children with attention-deficit/hyperactivity disorder in the laboratory school (the Comacs Study)." Pediatrics, 2004, 113(3): e206-e216.
Swanson, et al., "Effects of stimulant medication on growth rates across 3 years in the MTA follow-up," J. Am. Acad. Child Adolesc. Psychiatry, 2007, 46(8): 1014-1026.
Swanson, et al., "Secondary evaluations of MTA 36-month outcomes: propensity score and growth mixture model analyses," J. Am. Acad. Child Adolesc. Psychiatry, 2007, 46(8):1002-1013.
Swanson, et al., "Psychopharmacology: concepts and opinions about the use of stimulant medications," J. Child Psychol. Psychiatry, 2009; 50: 180-193.
Swanson, J., "Short and Long-term Tolerance to Stimulant Medication," Presentation at AACAP, 2012, San Fransisco, CA.
Swanson, et al., "Young adult outcomes in the follow up of the multimodal treatment study of ADHD: symptom persistence, source discrepancy, and height suppression," Journal of Child Psychology and Psychiatry, 2017, 58(6): 1-16.
Swanson, J., "ADHD in the 21st Century: Inconvenient but Incontrovertible Scientific Truths and Critical Unmet Needs," University of California, Irvine, Presentation, 2022.
Swanson, J., "Succinct Summary of a Theory of Accumulated Tolerance as the Basis for Long-term Tolerance", 2022.
Swanson, J., Invited Presentation (Hot Topic: Special Issues on Pharmacological Treatment of ADHD): Acute and late tolerance: Are these real problems using stimulants? World Federation of ADHD. 2023: Amsterdam.
Thanos, et al., "A pharmacokinetic model of oral methylphenidate in the rat and effects on behavior," Pharmacology, Biochemistry and Behavior, 2015, 131: 143-153.
United Nations, International Narcotics Control Board (INCB), Annual Report Psychotropic Substances, 2020, New York City NY.
Vitiello, et al., "Methylphenidate dosage for children with ADHD over time under controlled conditions: lessons from the MTA", J. Am. Acad. Child Adolesc. Psychiat., 2001; 40(2): 188-196.
Volkow, et al., "Is methylphenidate like cocaine? Studies on their pharmacokinetics and distribution in the human brain." Archives of general psychiatry, 1995, 52(6): 456-463.
Volkow, et al., "Relationship between blockade of dopamine transporters by oral methylphenidate and the increases in extracellular dopamine: therapeutic implications," Synapse, 2002; 43:181-187.
Volkow et al., "Variables that affect the clinical use and abuse of methylphenidate in the treatment of ADHD." Am. J. Psychiatry, 2003, 160: 1909-1918.
Volkow, et al., "Brain dopamine transporter levels in treatment and drug naïve adults with ADHD," NeuroImage, 2007, 34: 1182-1190.
Volkow, et al., "Basic Neuropsychopharmacology," Rutter's Child and Adolescent Psychiatry, 5th Edition, Blackwell Publishing. 2008, pp. 212-233.
Volkow, et al., "Evaluating dopamine reward pathway in ADHD: clinical implications," JAMA, 2009. 302: 1084-1091.

(56) References Cited

OTHER PUBLICATIONS

Volkow, et al., "Neurochemical and metabolic effects of acute and chronic alcohol in the human brain: Studies with PET," Neuropharm., 2017; 122: 175-188.

Vrijens, et al., "A new taxonomy for describing and defining adherence to medications." British journal of clinical pharmacology, 2012, 73(5): 691-705.

Walkup, J., "Practice parameter on the use of psychotropic medication in children and adolescents." Journal of the American Academy of Child & Adolescent Psychiatry, 2009, 48(9): 961-973.

Wallis, C., "Behavior: Attention Deficit Disorder: Life in Overdrive," Time Magazine, Jul. 18, 1994, vol. 144, in 2 pages.

Wang, et al., "Long-term stimulant treatment affects brain dopamine transporter level in patients with attention deficit hyperactive disorder," PLoS One, 2013, 8(5): 1-6.

Wender, P.H., "Minimal brain dysfunction in children." New York: Wiley-Interscience, 1971.

Wigal, et al., "Selection of the optimal dose ratio for a controlled-delivery formulation of methylphenidate," The Journal of Applied Research, 2003, 3(1): 46-63.

Wolraich, et al., "Clinical practice guideline for the diagnosis, evaluation, and treatment of attention-deficit/hyperactivity disorder in children and adolescents." Pediatrics, 2019, 144(4): 1-25.

Yano, et al., "Methylphenidate and cocaine: the same effects on gene regulation?" Trends in pharmacological sciences, 2007, 28(11): 588-596.

Zetterqvist, et al., "Stimulant and non-stimulant attention deficit/hyperactivity disorder drug use: total population study of trends and discontinuation patterns 2006-2009," Acta Psychiatr. Scand., 2013, 128: 70-77.

"Education of the Handicapped Act Amendments of 1990." US Congress (Public Law 101-476), 104 Stat. 1103, Oct. 30, 1990, in 49 pages.

Wallis, C., "Behavior: Attention Deficit Disorder: Life in Overdrive," Time Magazine, Jul. 18, 1994, in 17 pages.

* cited by examiner

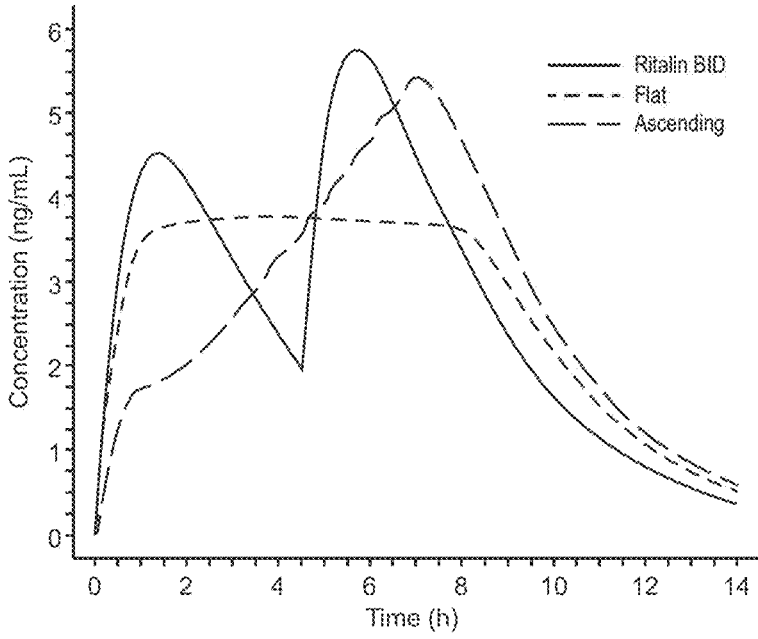

Study 1: Simulated plasma methylphenidate concentrations for a 20-mg total daily dose
delivered by twice-daily (bid), flat, and ascending dosing regimens.

FIG. 1A

Mean Pharmacokinetic Parameters Derived Using a Noncompartmental Model for 10mg QD Dose of Adderall

|  | *d*-Amphetamine | | *l*-Amphetamine | |
|---|---|---|---|---|
|  | QD | BID | QD | BID |
| $T_{max}$ (hours)[a] | 2.5 ± 1.2 | 6.5 ± 0.9 | 2.5 ± 1.2 | 6.4 ± 0.7 |
| $C_{max}$ (ng/mL)[a] | 28.4 ± 6.5 | 52.7 ± 16.8 | 9.6 ± 2.4 | 17.7 ± 5.2 |
| $AUC_{0-24}$ (ng/mL)[a] | 342.1 ± 108.6 | 630.6 ± 161.5 | 124.2 ± 37.2 | 227.3 ± 65.9 |
| $AUC_{0-inf}$ (ng/mL)[a] | 384.4 ± 108.6 | 789.3 ± 242.3 | 146.3 ± 51.6 | 305.8 ± 112.0 |
| $T_{1/2}$ | 7.5 ± 1.0 | 7.8 ± 1.8 | 8.6 ± 1.6 | 8.9 ± 2.5 |
| $K_C$ | 0.09 ± 0.01 | 0.09 ± 0.02 | 0.08 ± 0.02 | 0.08 ± 0.02 |

[a]For both isomers, the differences between QD and BID schedules were statistically significant.

FIG. 1B

Psychostimulant Actions on Dopamine and Limbic System

A comparison of Once-Daily Extended-Release Methylphenidate
Formulations in Children With Attention-Deficit/Hyperactivity Disorder
in the Laboratory School (The Comacs Study)

PREVENTION OF ACCUMULATED TOLERANCE TO STIMULANT MEDICATION FOR THE TREATMENT OF ADHD

RELATED APPLICATIONS

This application is a divisional of U.S. patent application Ser. No. 17/716,932, filed Apr. 8, 2022, which claims the benefit of U.S. Provisional Application No. 63/201,057, filed Apr. 9, 2021, the entireties of which are incorporated by reference herein.

BACKGROUND

The population prevalence of recognition of ADHD school-aged children has been increasing for decades (e.g., from <1% before 1970 to >10% by 2012 in the USA, and recently worldwide in adults as well as in children). A majority of recognized cases initiate treatment with stimulant medication, which is justified by many randomized clinical trials of short-term treatment that provide evidence of efficacy compared to alternatives (resulting in greater decrease in severity of ADHD symptoms for at least 3 to 6 months with an effect size ~0.8 in children and 0.5 in adults). Since childhood-onset ADHD is considered to be a chronic disorder that continues into adulthood in a majority of cases and confers elevated risk for a variety of adverse outcomes, and stimulant medications are considered to provide acute symptomatic benefit when taken, clinical guidelines recommend long-term treatment. However, this seldom occurs. Longitudinal evaluations of medication use in individuals indicate adherence and persistence of treatment has remained poor, even after development, approval, and widespread acceptance of sustained-release formulations of stimulant medications with ascending drug delivery, which provided effective once-a-day administration at home, reducing stigma associated with taking medication in public and inconvenience of taking medication two or three times a day. Retrospective studies of prescription records suggest most cases do not refill prescriptions in a timely manner, and prospective studies of cases that initiate adequate treatment in early childhood indicate most discontinue medication use in late childhood or in adolescence (often within the first year of treatment). Also, long-term relative benefit of long-term medication is notoriously difficult to document, even in the few cases that maintain long-term treatment with stimulant medication compared to cases that seek and obtain alternative treatments or are never treated with medication. There is a critical unmet need for a medication to treat chronic ADHD that will be used consistently from childhood to adulthood and will result in clear long-term clinical benefit.

From the 1930s to the 1970s, the approved stimulant medications for the treatment of DSM-II-diagnosed "hyperactivity" were short-acting drugs (methylphenidate and d-amphetamine), with onset of effects within 30 minutes and duration of effects 2 to 3 hours. These medications required multiple administrations across the day to provide effective treatment during school, and the common assumption was that the second and third doses should be reduced since the carryover associated with the pharmacokinetic (PK) properties would maintain a constant level of medication across the day and maintain behavioral or pharmacodynamic (PD) effects. Once-a-day formulations were available during this era (Ritalin SR® and Dexedrine Spansules®), but they were ineffective and were seldom used in clinical practice.

In the 1980s, when the modern diagnosis was revised in DSM-III (1980)[1] to Attention Deficit Disorder (ADD) without or with hyperactivity (ADDH), new approaches were developed to address the inconvenience and stigma associated with taking a controlled substances (amphetamine and methylphenidate). A Laboratory Protocol for repeated cognitive and behavioral assessments across they day was developed to measure the time course of PD effects (see Swanson et al, 1978)[2], and this approach was paired with PK measurements of methylphenidate (Ritalin®) and pemoline (Cylert®), the two most often used stimulant medications of the era, which showed the PD effect followed the PK levels of medication, and this led to an increase in the frequency of administration (e.g., for methylphenidate, every 3 to 4 hours). Based on decades of clinical use, the consensus was to administer medication twice a day with a sculpted dose regime (the $2^{nd}$ dose lower than the $1^{st}$), which Abikoff et al (1985)[3] proposed would be optimal, but some suggestions were to administer medication three times a day at the same dose even though the serum concentration of medication would gradually increase across they day, which Swanson et al (1983)[4] proposed would be optimal.

In the 1990s, this led to a compromise for treatment by-protocol in the MTA (Arnold et al, 1997)[5], with three times a day dosing but with the successive doses sculpted, which was considered (perhaps inappropriately) optimal for treatment with stimulant medication in the 14-month randomized clinical trial (RCT). The optimal benefit for a specific drug to treat a specific disorder depends on temporal factors, including duration of the disorder (e.g., whether it is a chronic or temporary clinical condition) and the frequency and intensity of the treatment with medication that is related to the drug's duration of action (e.g., which may be different for different individuals). The usual procedure for well-managed treatment is to match these temporal factors. This can be accomplished by trying different doses and timing of administration of the drug, which is called (i.e., titration). In the MTA, a double-blind titration trial was conducted (see Greenhill et al, 2001)[6], and the best dose for initiating treatment with methylphenidate was selected for each case. Over the 14-month RCT, continuation of medication was reviewed in monthly clinic visits, and adjustments to dose were recommended to maintain full efficacy, which resulted in regular increases in dose by about 15% over the 14-months of the MTA (Vitiello et al, 2001)[7].

When the diagnosis was revised in DSM-IV (1994)[8] to Attention-Deficit/Hyperactivity Disorder (ADHD), the Laboratory Protocol was extended to evaluate the PD effects of a mixture of the d- and l-isomers of amphetamine (Adderall®), which was revived and proposed as a longer-acting stimulant medication to treat ADHD, with a claimed duration of behavioral effect of a single morning dose that would cover the school-day (e.g., of 8 to 10 hours) compared to 3 hours for Ritalin® and 6 hours for Cylert.® However, the observed duration (PD half-life) was 6 hours, so two daily doses were required to cover the school day. Also, the Laboratory Protocol was applied to evaluate the PK/PD properties of methylphenidate. Swanson et al (1999)[9] reported the dissipation of benefit on classroom behavior when the level of methylphenidate was held constant across the day (mimicking Ritalin SR®), which suggested acute tolerance (or tachyphylaxis) may undermine efficacy, but dissipation was not observed for an ascending drug delivery, which counteracted acute tolerance and maintained a constant PD effect on behavior. This knowledge was used to develop an Osmotic Release Oral System (OROS®) for a sustained-release formulation of methylphenidate (Concerta®) with a 10-12 hour duration (Swanson et al, 2003)[10], which was approved for use in 2000 and was rapidly accepted in clinical practice as an effective once-a-day pharmacological treatment for ADHD.

The Laboratory Protocol was used to evaluate the PK/PD properties of Adderall® (Swanson et al, 1998)[11], which also showed tachyphylaxis (dissipation of efficacy with 3 hours even though serum concentration remained high for 6 hours), and to evaluate a coated-bead delayed-release system for a once-a-day formulation (Adderall XR®) designed to overcome the acute tolerance with an ascending serum concentration of amphetamine, which produced a 12-hour duration of efficacy. However, this formulation also showed carry-over tolerance the next day before the morning administration of Adderall XR® (see FIG. 1A) when cognitive performance (number of problems worked) was reduced compared to the first test of the day in the placebo condition (McCracken et al, 2003)[12]. This pattern of carry-over tolerance was also manifested in a coated-bead formulation of methylphenidate that delivered an ascending serum concentration of methylphenidate across 8 hours (see FIG. 1). Despite the carry-over tolerance, these controlled-release formulations of stimulant medications (with long-duration of efficacy that allowed for once-a-day administration of stimulant medication) were well-accepted, and from 2000 to 2005 essentially replaced the multiple daily dose regimes (TID for methylphenidate and BID for amphetamine) that had been used for decades.

Concern about abuse potential of amphetamine led to the development of a pro-drug with lower abuse potential (Vyvanse®) as an alternative for Adderall XR®. Also, other sustained-release formulations based on coated-beads of immediate-release methylphenidate (e.g., Metadate CD® and Ritalin LA®) and amphetamine (e.g., were developed and were being used in clinical practice, and by the mid-2000s, a large majority of ADHD cases were being treated with once-a-day administration of stimulant medication. Many studies documented that adherence and persistence were better for once-a-day clinical regimes of sustained-release formulations than for TID or BID clinical regimes of immediate-release formulations. Also, non-stimulant medications have been evaluated and approved for the treatment of ADHD, including atomoxetine (Strattera®), guanfacine (Intuiv®), and clonidine (Kapay®), and some other medications not approved for ADHD but approved for other disorders have been used to treat ADHD, including modafinil (Provigil®) and mazindol (Quilience®). However, Concerta® and Adderall XR® remain as the two most often prescribed medications for the treatment of ADHD.

Despite the proliferation of approved medications for the treatment of ADHD (see Mattingly et al, 2021[13] for a summary), the adherence and persistence of medication use has remained poor. As indicated in the Background, the population prevalence of use of stimulant and non-stimulant medications for the treatment of ADHD has increased dramatically, but this is due to more cases initiating treatment and not to cases remaining in treatment for longer times.

The optimal frequency of use (how often a drug is taken) depends on the relationship of the pharmacokinetic (PK) properties of the medication (what the drug does to the body) and the pharmacodynamic (PD) properties (what the body does to the drug). The PK properties described how drugs are absorbed, reach the site of action, are metabolized and deactivated, and then excreted. The PD properties describe the impact when the drug reaches the site of action, which can be measured by observing the physiological, behavioral, or other responses. The basic principles of PK/PD evaluation are described by Swanson and Volkow (2008)[14], developed and applied in the 1980s to measure the PK and PD properties of stimulant medications (methylphenidate and pemoline) in children, and in the 1990s extended to evaluate PD properties of amphetamine (Swanson et al, 1998)[15]. This approach was applied to evaluate dynamic processes may occur that reduce the PK and PD effects of drugs over time and subsequent effects of repeated administrations of the drug, which led to an innovative proposal for drug delivery (i.e., an ascending profile). The immediate dynamic effects are called acute tolerance (or tachyphylaxis). The Laboratory School Protocol was applied to develop drug delivery patterns that would overcome tachyphylaxis and maintain efficacy across the day. This was used to document PK and PD properties of methylphenidate (Swanson et al, 1999)[16] and amphetamine (Greenhill et al, 2003)[17]. Swanson et al (2000)[18] proposed an increase in dose across the day to overcome tachyphylaxis, which was the basis for the application of the OROS technology for an ascending delivery of methylphenidate across the day for Concerta® with ascending PK and constant PD profiles across the day. This provided an effective once-a-day administration of this drug as the treatment of ADHD. McCracken et al. (2003)[19] proposed a two-pulse release of d,l-amphetamine to achieve and ascending PK and constant PD profiles delivery of this drug as Adderall-XR®. This provided effective once-a-day administration to treat ADHD. Wigal et al (2003)[20] proposed a 2-pulse release of d-threo-methylphenidate to achieve and ascending PK and constant PD profiles delivery as Metadate-CD. After appropriate titration, the optimal benefit across days depends on adherence (how often) and persistence (how long) of daily use of medication. However, when taken as prescribed, the relative benefit of a constant titrated daily dose of medication may dissipate. This is called long-term tolerance.

SUMMARY

In accordance with certain implementations there is a pharmaceutical composition for treating ADHD, comprising a first component comprising a first unit dose of a first drug formulated for immediate release, wherein the first drug is a stimulant drug having effectiveness against ADHD and which causes tachyphylaxis; and a second component comprising an extended-release formulation of a second drug having effectiveness against ADHD and configured to be delivered over a time period beginning about 2 to 4 hours following administration of the composition and ending about 6 to 14 hours following administration of the composition, wherein the second drug does not cause tachyphylaxis; wherein the composition is in a single unit dosage form; and wherein the composition treats ADHD without accumulating tolerance for the first drug when administered on a once-daily basis.

In accordance with certain implementations there is a pharmaceutical composition for treating ADHD, comprising a first component comprising a first unit dose of a first drug formulated for immediate release, wherein the first drug is a stimulant drug having effectiveness against ADHD and which causes tachyphylaxis; and a second component comprising an extended-release formulation of a second drug having effectiveness against ADHD and configured to be delivered and/or have efficacy over a time period beginning about 30 minutes to 4 hours following administration of the composition and ending about 6 to 14 hours following administration of the composition, wherein the second drug does not cause tachyphylaxis, does not contribute to the accumulation of tolerance, and/or does not contribute significantly to the accumulation of tolerance; wherein the composition is in a single unit dosage form; and wherein the composition treats ADHD without accumulating tolerance for the first drug when administered on a once-daily basis.

In accordance with certain implementations there is a pharmaceutical composition for treating ADHD, comprising a first component comprising a first unit dose of a first drug formulated for immediate release, wherein the first drug is a stimulant drug having effectiveness against ADHD and which causes tachyphylaxis; and a second component comprising an extended-release formulation of a second drug having effectiveness against ADHD and configured to be delivered over a total period of about 6 to 10 hours, such period beginning about one hour before the pharmacodynamic half-life of the first drug and ending about one hour after the pharmacodynamic half-life of the first drug, wherein the second drug does not cause tachyphylaxis; wherein the composition is in a single unit dosage form; and wherein the composition treats ADHD without accumulating tolerance for the first drug when administered on a once-daily basis.

In accordance with certain implementations there is a pharmaceutical composition for treating ADHD, comprising a first component comprising a first unit dose of a first drug formulated for immediate release, wherein the first drug is a stimulant drug having effectiveness against ADHD and which causes tachyphylaxis; and a second component comprising an extended-release formulation of a second drug having effectiveness against ADHD and configured to be delivered and/or have efficacy over a total period of about 6 to 10 hours, such period beginning about one hour before the pharmacodynamic half-life of the first drug and ending about one hour after the pharmacodynamic half-life of the first drug, wherein the second drug does not cause tachyphylaxis, does not contribute to the accumulation of tolerance, and/or does not contribute significantly to the accumulation of tolerance; wherein the composition is in a single unit dosage form; and wherein the composition treats ADHD without accumulating tolerance for the first drug when administered on a once-daily basis.

In accordance with certain implementations, the second component is a solid dosage form (e.g., pill, tablet, caplet, osmotic dosage form) and the first component is in the form of a coating applied upon some or all of an outer surface of the second component. In accordance with certain implementations, the composition is in the form of a capsule containing therein one or more first beads comprising the first component for immediate release and two or more second beads comprising the second component for extended release. In accordance with certain implementations, the first drug is selected from the group consisting of: dextroamphetamine, amphetamine, dexmethylphenidate, methylphenidate, lisdexamfetamine, and combinations thereof. In accordance with certain implementations the second drug is selected from the group consisting of: mazindol, modafinil, atomoxetine, clonidine, guanfacine, viloxazine, bupropion, desipramine, imipramine, nortriptyline, and combinations thereof. In accordance with certain implementations, the composition is effective for a period of about 10 to 16 hours following administration. Some composition implementations may include two or more of the foregoing.

In accordance with certain implementations, there is a method of treating ADHD or symptoms thereof, comprising: administering a first unit dose of a first drug formulated for immediate release wherein the first drug is a stimulant drug having effectiveness against ADHD and which causes tachyphylaxis to a patient in need thereof; and administering an extended-release formulation of a second drug having effectiveness against ADHD and configured to be delivered over a time period lasting about 6 to 12 hours, wherein the second drug does not cause tachyphylaxis; wherein the extended-release formulation of the second drug is administered such that the delivery of the second drug is initiated within a period beginning one hour before the pharmacodynamic half-life of the first drug and ending one hour after the pharmacodynamic half-life of the first drug; and wherein the composition treats ADHD or symptoms thereof without accumulating tolerance for the first drug when administered on a once-daily basis.

In accordance with certain implementations, there is a method of treating ADHD or symptoms thereof, comprising: administering a first unit dose of a first drug formulated for immediate release wherein the first drug is a stimulant drug having effectiveness against ADHD and which causes tachyphylaxis to a patient in need thereof; and administering an extended-release formulation of a second drug having effectiveness against ADHD and configured to be delivered over a time period lasting about 6 to 12 hours, wherein the second drug does not cause tachyphylaxis, does not contribute to the accumulation of tolerance, and/or does not contribute significantly to the accumulation of tolerance; wherein the extended-release formulation of the second drug is administered such that the delivery of the second drug is initiated within a period beginning one hour before the pharmacodynamic half-life of the first drug and ending one hour after the pharmacodynamic half-life of the first drug; and wherein the composition treats ADHD or symptoms thereof without accumulating tolerance for the first drug when administered on a once-daily basis.

In accordance with certain implementations, there is a method of treating ADHD, comprising: administering a first unit dose of a first drug formulated for immediate release wherein the first drug is a stimulant drug having effectiveness against ADHD and which causes tachyphylaxis to a patient in need thereof; and administering an extended-release formulation of a second drug having effectiveness against ADHD and configured to be delivered over a time period lasting 6 to 10 hours, wherein the second drug does not cause tachyphylaxis; wherein the extended-release formulation of the second drug is administered such that the second drug is delivered beginning about 2-4 hours following administration of the first drug; and wherein the composition treats ADHD without accumulating tolerance for the first drug over time.

In accordance with certain implementations, there is a method of treating ADHD, comprising: administering a first unit dose of a first drug formulated for immediate release wherein the first drug is a stimulant drug having effectiveness against ADHD and which causes tachyphylaxis to a patient in need thereof; and administering an extended-release formulation of a second drug having effectiveness against ADHD and configured to be delivered and/or have efficacy over a time period lasting 5 to 13 hours, wherein the second drug does not cause tachyphylaxis, does not contribute to the accumulation of tolerance, and/or does not contribute significantly to the accumulation of tolerance; wherein the extended-release formulation of the second drug is administered such that the second drug is delivered beginning about 30 minutes to 4 hours following administration of the first drug; and wherein the composition treats ADHD without accumulating tolerance for the first drug over time.

In accordance with certain implementations, the first and second drug are administered simultaneously. In accordance with certain implementations, the first and second drug are administered at different times and the first drug is delivered before the second drug is delivered. In accordance with certain implementations, the second drug is a solid dosage form and the first drug is in the form of a coating applied upon some or all of an outer surface of the second drug. In accordance with certain implementations, the first and second drugs are contained in a capsule containing therein one or more first beads comprising the first drug for immediate release and two or more second beads comprising the second drug for extended release. In accordance with certain implementations, the first drug is selected from the group consisting of: dextroamphetamine, amphetamine, dexmethylphenidate, methylphenidate, lisdexamfetamine, and combinations thereof. In accordance with certain implementations, the second drug is selected from the group consisting of: mazindol, modafinil, atomoxetine, clonidine, guanfacine, viloxazine, bupropion, desipramine, imipramine, nortriptyline, and combinations thereof. Some method implementations may include two or more of the foregoing.

In some implementations there is a pharmaceutical dosing pack for treating ADHD, comprising: a blister pack divided into at least two sections that permits the dispensing of individual doses of one or more drugs; wherein a first section contains one or more individual daily first doses of a first drug formulated for immediate release, wherein the first drug is a stimulant drug having effectiveness against ADHD and which causes tachyphylaxis; and wherein a second section contains one or more individual daily second doses of a second drug formulated for extended-release and has effectiveness against ADHD, wherein the second drug does not cause tachyphylaxis, does not contribute to the accumulation of tolerance, and/or does not contribute significantly to the accumulation of tolerance. In some implementations, the dosing pack is adapted for the first and second sections to be physically separated, such as by tearing along a perforated line separating the first and second sections. This allows for a daily dose of stimulant drug, or multiple doses of stimulant drug, to be separated from their corresponding daily dose of alternative ADHD drug. This can be useful for circumstances, such as schools, where the regulatory or legal classification of the drug (e.g., Schedule II stimulants in the U.S.) may complicate the possession, handling or administration of the drug. Following separation of the sections, there will be a first section with one or more daily doses of the first drug and a second section with one or more daily doses of the second drug. Such a pack can allow for the first section to remain at home where a child can take the first drug at home under the supervision of an appropriate adult or guardian while leaving the second section (or portions thereof) at a separate location where the child spends most of their day, such as a school, and be administered the daily dose of alternative ADHD drug when appropriate. In certain implementations, the dosage pack can further include instructions for use on or accompanying the pack. In certain implementations, the dosage pack delivers drugs so as to have efficacy over a time period of about 10 to 16 hours when taken as instructed.

BRIEF DESCRIPTION OF THE DRAWINGS

FIG. 1A: Simulated plasma methylphenidate concentration for a daily dose; FIG. 1B: Mean pharmacokinetic parameters derived using a noncompartmental model.

DETAILED DESCRIPTION

Figure 2:
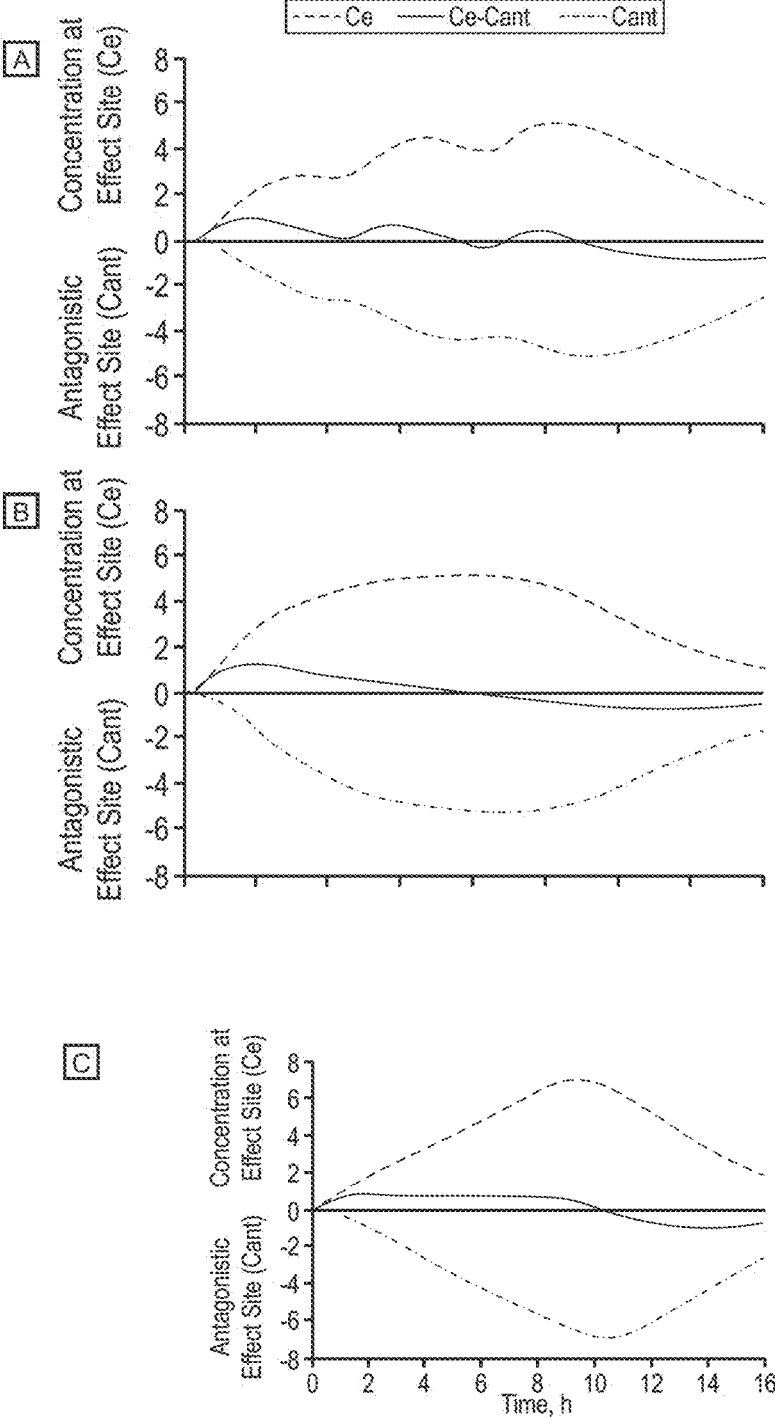
FIG. 2: Effect site (Ce), antagonist site (Cant), and net (Ce-Cant) profiles from pharmacokinetic-pharmacodynamic modeling for the following three conditions A: those receiving a regimen of immediate-release methylphenidate hydrochloride three times daily; B: those receiving a bolus that created a flat pattern based on the prototype drug delivery profile for sustained-release methylphenidate hydrochloride formulations (i.e. 8 mg at 7:30 AM, followed by small constant 1.25 mg doses at 30-minute intervals; and C: those receiving a bolus that created an ascending pattern based on the concept of acute tolerance (8 mg at 7:30 AM followed by small and increasing doses from 1.3 to 2.6 mg at 30-minute intervals)

Stimulant medications (methylphenidate or amphetamine) are often initiated for short-term treatment of ADHD, but are seldom continued even though long-term treatment is recommended. One reason (that is not appreciated) is that clinical benefit (reduction of symptoms) wanes due to emergence of long-term tolerance. There is an unmet need for new treatments that will remain effective and be continued in the long-term and provide long-term clinical benefit.

New analyses and insights regarding long-term use of stimulant medication and pharmacodynamic and homeostatic properties of neural response to dopamine-agonist drugs suggest innovative pharmacological approaches to avoid long-term tolerance. One solution is based on retaining the first component of available controlled-release formulations (i.e., a titrated bolus dose of stimulant medication to elicit rapid but temporary reduction of symptoms) and replacing the second component (i.e., ascending delivery of stimulant medication to counteract acute tolerance) with a non-dopamine agonist drug, titrated and delivered to maintain efficacy but to avoid carry-over and accumulated tolerance that undermine long-term efficacy.

Recent reviews indicate adherence and persistence remain poor in modern clinical practice (even when controlled-release formulations have essentially replaced immediate-release formulations), and new analyses of long-term follow-up studies indicate continuation of medication use (even for a decade, with regular dose increases) is not associated with relative benefit compared to discontinuation or negligible use. Thus, new and innovative approaches are needed, since treatment with higher daily dose and with controlled-release formulations (i.e., with two components, a bolus dose to elicit rapid clinical benefit and ascending drug delivery across the day to counteract acute tolerance), and regular monitoring to provide increases in daily dose to counteract a short-term tolerance), have not been successful in increasing long-term adherence and persistence of medication use.

Proposals are provided here based on insights about long-term neural responses to stimulant drugs, and the realization that application of the standard approach (i.e., increasing dose) is counter-productive in the long-term, and inevitably results in long-term tolerance that undermines long-term efficacy. An alternative is proposed based on retaining a bolus dose of stimulant medication to elicit a rapid response, and replacing the subsequent ascending delivery (that overcomes initial tolerance but elicits long-term tolerance) by a non-stimulant drug, delaying the next bolus to allow for dissipation of tolerance.

As used herein, especially as regards drugs and pharmaceutical formulations, XL refers to extended-release, CR refers to controlled release, and these terms may be used interchangeably. DA refers to dopamine, PK refers to pharmacokinetic, PD refers to pharmacodynamic, and ADHD refers to attention-deficit hyperactivity disorder or attention-deficit disorder.

Neuroanatomical and neurochemical models of ADHD and models of neural processes underlying and linking response to the sites of action suggest stimulant medication (that are considered to be dopamine-agonists drugs with specific anatomic sites of action). Stimulant medications (methylphenidate and amphetamine) are rapidly absorbed and are taken by blood flow to dopamine (DA) synapses in specific brain regions (e.g., the caudate nucleus), which can be monitored by Positron Emission Tomography (PET) imaging, which uses special compounds (ligands) labeled with radioactive isotopes that emit signals that are detected by the PET imaging device and are used to localize their location in the brain.

The hypothesis underlying the use of stimulant medication to treat ADHD is that these drugs are DA agonists (and increase the action of this neurotransmitter by blocking the DA Transporter (DAT) that recycles released DA and increases the synaptic level, which propagates neural transmission (Swanson and Volkow, 2002)[21]. Homeostatic processes that maintain levels of synaptic DA are engaged, including the increase in density of DAT (see Volkow et al, 2008)[22]. In adults with ADHD, consistent treatment with methylphenidate (i.e., a potent DA agonist drug) increases DAT density over a year of consistent medication use (Wang et al, 2013)[23].

The acute treatment of ADHD with stimulant medication is associated with acute tolerance (tachyphylaxis), which requires increases in the concentration of the drug at the site of action in the brain to maintain efficacy across the day. For the OROS® formulation designed for Concerta®, the ascending drug delivery was programmed to terminate after 8-10 hours, which was intended to allow for dissipation of acute tolerance and to prevent carryover tolerance to the next day. However, Swanson (2012)[24] summarized PK/PD studies and suggested acute tolerance does not dissipate completely overnight, and proposed carry-over tolerance emerges across 7 days of treatment that must be overcome when the next dose is administered the next day. The increased density of DAT is presumed to be a mechanism of long-term tolerance.

The recognition of Attention-Deficit/Hyperactivity Disorder (ADHD) in the worldwide population has been increasing for decades (e.g., from <3% of school aged-children in 1990 to ~10% of children and 5% of adults by 2020; see Faraone et al, 2021)[25], and use of stimulant medication to treat ADHD has been increasing also (e.g., by 500% from 1990 to 2020; see UN-INCD, 2020)[26]. These high recognition and treatment rates have been justified by evidence of relative efficacy (greater decrease in symptom severity for treatment with medication compared to alternatives) in rigorous reviews of randomized controlled trials (Storebo et al, 2015[27] and Cortese et al, 2018[28]), with large-to-medium average effect size in many short-term trials (≤3 or ≤6 months) for children (~0.8) and adults (~0.5), and medium-to-small in long-term trials (>1 year) for children (0.47) and adults (0.21). Since ADHD is usually a chronic condition associated with a variety of adverse functional outcomes (see Hechtman et al, 2016)[29], clinical practice guidelines recommend continuation of treatment for as long as symptoms of ADHD continue (i.e., through adolescence and into adulthood in a majority of childhood-onset cases). But, significant long-term relative benefit for extended treatment with stimulant medication has been difficult to document for a variety of reasons (see Molina and Swanson, 2020)[30], including decreasing efficacy and increasing discontinuation over time. Recent reviews of prospective observational follow-up studies and retrospective studies of prescription records (Gajria et al, 2014[31] and Ahmed and Aslani, 2013[32]) indicate the average duration of adequate treatment with stimulant medication is surprisingly low (<1 year). In contrast to dramatic increases in cross-sectional estimates of population prevalence, longitudinal estimates of adherence and persistence of medication use in individuals have not changed since the 1970s. There is a critical unmet need for a pharmacologic treatment of ADHD that will remain effective and will not be inappropriately discontinued (see Charach and Fernandez, 2013)[33].

Recently, Cortese (2019)[34] commissioned a debate to address the issue of long-term benefit. Coghill (2019)[35] proposed exemplary clinical care based on the MTA medication algorithm (with frequent monitoring and regular dose increases to maintain efficacy) is seldom provided but could result in good adherence and persistence and long-term relative benefit. In contrast, Swanson (2019)[36] proposed even for exemplary clinical care, unrecognized and unappreciated long-term tolerance would inevitably emerge for long-term treatment with stimulant medications (considered to be dopamine agonist drugs), undermining long-term efficacy and resulting in poor adherence and persistence and complete dissipation of relative benefit. New analyses and insights regarding long-term use of stimulant medication and pharmacodynamic and homeostatic properties of neural response to dopamine-agonist drugs are presented here, which suggest innovative pharmacological approaches to avoid long-term tolerance. One solution is based on retaining the first component of available controlled-release formulations (i.e., a titrated bolus dose of stimulant medication to elicit rapid but temporary reduction of symptoms) and replacing the second component (i.e., ascending delivery of stimulant medication to counteract acute tolerance) with a non-dopamine agonist drug, titrated and delivered to maintain efficacy but to avoid carry-over and accumulated tolerance that undermine long-term efficacy.

Over the past 30 years, the population prevalence of the use of stimulant medication to treat ADHD has increased dramatically (by >274%), but the longitudinal use by individuals has not changed (and shows the opposite trend of dramatic decreases over time). The drugs approved to treat this very common disorder (affecting ~10% of the school-aged population), are very effective in the short-term (weeks to months), but long-term benefits of long-term treatment (>2 year) has not been shown (see Molina and Swanson, 2020)[37]. Relative efficacy of treatment with stimulant medication (compared to alternative treatment) has been documented for short-term treatment (from a few weeks or months), but it the relative benefit dissipates completely over longer periods of treatment (years to decades). ADHD in most cases is a chronic disorder that needs effective treatment from childhood to adulthood. A medication treatment with long-term efficacy is needed, but usually treatment is stopped in childhood. The most common reason given for stopping medication is "the medication stopped working".

The general consensus of clinicians is that response to stimulant medication is maintained over long periods of treatment, but that patients still have poor adherence and persistence that limits long-term benefit. Education and clinical follow-up are recommended to improve long-term treatment by increasing adherence and persistence of use of currently approved medications. However, the dissipation of relative benefit associated with long-term treatment may be due to long-term tolerance. If so, then to improve adherence (how often) and persistence (how long) of medications for long-term treatment of ADHD, it may be necessary to develop medications that are not undermined by long-term tolerance. This would meet a critical clinical need.

Details Regarding Current Treatments

To summarize, stimulant medications (methylphenidate or amphetamine) are often initiated for short-term treatment of ADHD, but are seldom continued even though long-term treatment is recommended. One reason (that is not appreciated) is that clinical benefit (reduction of symptoms) wanes due to emergence of long-term tolerance. There is an unmet need for new treatments that will remain effective and be continued in the long-term and provide long-term clinical benefit.

Attention Deficit Hyperactivity Disorder (ADHD) is a common neurodevelopmental disorder with an estimated worldwide prevalence of 5-10% in children, which is considered to be a chronic condition in most cases with substantial risk for adverse outcomes in childhood, adolescence, and adulthood. Professional guidelines recommend early recognition and treatment. Clinical experience and research indicate stimulant medication (methylphenidate or amphetamine) and behavior modification (home-based and school-based contingency management) provide effective symptomatic treatment for ADHD. Stimulant medications are rapidly absorbed and metabolized, which defined their pharmacokinetic (PK) properties measured as the serum concentrations of methylphenidate (see FIG. 1A) and amphetamine (see FIG. 1B). Non-stimulant medication are also used but are not as effective as these two stimulant medications.

The use of stimulant medication to treat ADHD has been controversial in the past, but meta-analyses of controlled studies conclude that short-term treatment with stimulant medication provides greater relative efficacy than alternative non-pharmacological treatments, non-stimulant medications, or treatment with inactive placebo. Since ~1990 clinical use has become well accepted and worldwide use increased dramatically, and now stimulant medication is prescribed for up to 10% of school-aged children and 2% of adults in some countries. Most cases show beneficial effects (i.e., significant reduction of symptom severity) when treatment is initiated, but are "symptomatic effects" and are present only when the drug is taken, and are proportional to the serum concentrations of the drugs (see FIGS. 1A,B). Professional guidelines recommend continuation of prescribed treatment for as long as symptoms persist, but in practice this rarely occurs. Observational follow-up studies consistently have shown that almost all cases inexplicably discontinue use of medication in childhood or adolescence. Prescription records of modern clinical practice confirm this pattern.

The outdated concept of medication compliance (passive acceptance of the physician's prescribed use) suggests discontinuation may be inappropriate, but the modern concept of medication adherence (active collaboration of the patient and physician for decisions about adjustments to prescribed medication) suggests discontinuation may be appropriate. In follow-up studies of children the primary reasons cited by patients for discontinuation are "medication is no longer effective" or "I do not need it" and "medication makes me feel bad". Also, in observational follow-up studies of children with clear short-term benefits, neither naturalistic nor randomized discontinuation of medication during long-term treatment results in significant deterioration, and randomized discontinuation in controlled studies of adults have not documented the expected deterioration when the use of medication is stopped.

A recent debate regarding the lack of long-term benefit of long-term treatment with medication presented two alternatives explanation for these observations: (a) treatment as-usual may not be effective because well-established exemplary clinical practices were not applied or (b) long-term treatment may result in long-term tolerance that accumulates and inevitably undermines long-term efficacy. FIG. 2 suggests typical clinical practices and strategies to overcome acute tolerance (i.e., ascending daily doses to extend efficacy across the day) may be counterproductive, and insight suggests usual practices implemented to overcome long-term tolerance (i.e., regular increases in daily dose to maintain full efficacy across months of treatment) may eventually become ineffective.

There is an unmet need for a formulation of stimulant medication that will maintain efficacy and adherence in long-term treatment of ADHD. Based on experience in and information from clinical pharmacology, brain imaging, and neurochemistry), FIGS. 3A, 3B and 3C outline advantageous insights about the neural mechanisms that underlie acute tolerance, and FIG. 4 outlines insights about carry-over tolerance and the emergence of long-term tolerance.

These insights suggest innovative alternative strategies designed and intended to maintain efficacy of extended pharmacological treatment of ADHD without resulting in accumulation of long-term tolerance and dissipation of long-term clinical benefit, which contribute to poor adherence and persistence of medication use and provide direction for development of new formulations of medication for long-term treatment of ADHD.

New analyses and insights regarding long-term use of stimulant medication and pharmacodynamic and homeostatic properties of neural response to dopamine-agonist drugs suggest innovative pharmacological approaches to avoid long-term tolerance. One solution is based on retaining the first component of available controlled-release formulations (i.e., a titrated bolus dose of stimulant medication to elicit rapid but temporary reduction of symptoms) and replacing the second component (i.e., ascending delivery of stimulant medication to counteract acute tolerance) with a non-dopamine agonist drug, titrated and delivered to maintain efficacy but to avoid carry-over and accumulated tolerance that undermine long-term efficacy.

Attention Deficit Hyperactivity Disorder (ADHD) is classified as a neurodevelopmental disorder according to the most recent diagnostic criteria in DSM-5 (2013)[38] and ICD-11 (2019)[39] manuals. Usually, ADHD has onset in early childhood and is characterized by normal intellectual and physical development but abnormal behavior due to specific psychiatric symptoms (inattention, impulsivity, and hyperactivity), which are considered pathological due to age-inappropriate frequency and intensity and are associated with significant impairment in multiple settings at home and in school. ADHD is a chronic disorder in a majority of cases with continued manifestation of some symptoms and impairment in adolescence and adulthood (Faraone et al, 2021)[40]. Follow-up documents increased risk for adverse outcomes in childhood (school, family, peer problems, etc.), adolescence (substance use, school dropout, delinquency, etc.), and adulthood (unemployment, martial problems, psychiatric diagnoses, etc.). Therefore, early recognition and effective treatment are considered essential. The recognition of ADHD has been controversial in the past, due in part to large cross-national differences (e.g., from <1% in some parts of Asia, Australia, Africa, and Western Europe to ~10% in some parts of North America, Northern Europe, and South America) and an increasing secular trend (3-fold since 1990). However, when the same criteria are applied, meta-analyses concluded that the worldwide epidemiological prevalence of ADHD is similar across difference countries and cultures and has been stable (5-10% of children and 2-5% of adults) since the development of ICD-9 (1979)[41] and DSM-III (1980)[42] criteria (see Polanczyk et al, 2014)[43].

The use of stimulant medication (amphetamine) was discovered serendipitously almost century ago by Bradley (1937)[44]. Clinical application increased when methylphenidate was developed in the 1960s. Amphetamine and methylphenidate are highly controlled substances with abuse potential when administered intravenously, intra-nasally, or orally at high doses, so their clinical use to treat children is controversial. However, for decades (see Safer and Allen, 1976)[45] standard clinical practice has suggested methylphenidate and amphetamine have immediate and clear clinical benefits (acute reduction in symptom severity) and are safe (few serious side effects other than suppression of appetite and sleep disturbance, which usually dissipate with continuation of treatment). At the end of the 20th century, thousands of uncontrolled studies were summarized in systematic reviews (see National Research Council, 1989[46] and Swanson et al, 1993)[47], which documented efficacy and safety of short-term treatment. However, when recognition and treatment of ADHD in the USA increased suddenly in the 1990s (from about 1% in 1990 to over 3% in 1994), there was scientific concern since there were no adequately-controlled studies of long-term treatment for more than a few weeks or months (National Research Council, 1989[48] and NIMH RFA, 1992[49]), and there was substantial public controversy about the use of controlled drug with abuse potential to treat children with behavioral problems (see Time, 1994)[50].

As outlined above, in the 1990s there were no controlled studies of long-term treatment (defined for >1 year), which generated public controversy and scientific concern. To address this deficiency, the Multimodal Treatment Study of ADHD (MTA) was solicited in 1992 by Request for Applications (NIMH, RFA 92-178)[51]. The MTA was designed in 1993 and implemented from 1994 to 1997 as a randomized clinical trial (RCT) of childhood-onset ADHD. In a 6-site study, a statistically-powered sample was recruited and diagnosed by DSM-IV (1994)[52] criteria, with a target of 144 children per site between 7.0 to 9.9 years of age), and 579 cases were identified and assigned to long-term treatment (defined at the time as >1 year) provided "by-protocol" (see Arnold et al, 1997)[53] according to state-of-the-art stimulant medication (Med), intensive behavior modification (Beh), or the combination (Comb) compared to treatment as-usual in community (CC) settings (if sought and obtained). The primary goal of the MTA was to evaluate the hypothesis of relative efficacy (i.e., greater reduction in symptom severity) of stimulant medication compared to the alternative treatments when methylphenidate was initiated with a double-blind dose-response titration trial to select the best daily dose (see Greenhill et al, 2001)[54] and continued for the remainder of the 14-month controlled trial, with regular monitoring by the MTA medication algorithm (based on monthly clinic visits to evaluate and adjust prescribed medication to maintain full benefit). The findings of the RCT (MTA Group, 1999)[55] documented long-term benefits of long-term treatment. The groups randomly assigned to receive stimulant medication as a component of treatment had significantly greater efficacy for the groups assigned to treatment with behavior modification or treatment as-usual (Med+Comb>Beh+CC). Based on the standard RCT methodology (rigorous intent-to-treat analyses of all randomized cases), the effect size (standardized mean difference) was 0.6, indicating a medium-to-large clinical benefit. In addition, there was a non-significant additional benefit for the combination of the two modalities compared to medication alone (Comb vs Med). Thus, the MTA provided what is considered to be the "gold standard" for evidence of efficacy, which muted the controversy of the era and contributed to increased acceptance of use of stimulant medication. One of the secondary findings of the MTA (se Vitiello et al, 2001)[56] indicated exemplary treatment by-protocol (designed and intended to counteract dissipation of full benefit) resulted in regular increases in daily dose (by ~5%-20% per year), which at the end of the 14-month RCT phase resulted in a higher average daily dose (~30 mg/day) than treatment provided as-usual with medication (~20 mg/day).

The MTA was extended as an observational follow-up study, with a planned maintenance phase, in which use of stimulant medication could be continued by treatment as-usual (if sought and obtained in community practices). By 2 years after baseline, intent-to-treat analyses revealed that after transition, the initial greater efficacy had dissipated by 50% over the 10-month maintenance phase (see MTA Group, 2004a[57] and 2004b[58]). Subsequently at the follow-up 3 years after baseline, the initially greater relative benefit for ratings of symptom severity had dissipated completely based on intent-to-treat analyses of the randomized groups (see Jensen, et al, 2007)[59] or companion of naturalistic subgroups defined that were Consistently, Newly, Inconsistently, or Negligibly treated with stimulant medication (Swanson et al, 2007a[60] and 2007b[61]), and these groups did not differ significantly based on assessments of emergent problems associated with delinquency or substance use (see Molina et al, 2007)[62]. In adolescence, current use or past history of medication use did not account for dissipation of relative benefit on symptom severity (or for the lack of prevention of the emergence of substance use or delinquency; see Molina et al, 2009[63] and 2013[64]). Over the 16-year follow-up, about 50% of cases had persistence of symptoms (see Sibley et al, 2016[65]) and adverse functional outcomes were observed compared to a local normative comparison group (LNCG) of classmates (see Hechtman et al, 2016)[66]. By the end-point of the MTA (16 years after baseline, when the average age of participants was ~26 years of age), almost all cases (except about 5%) HAD discontinued treatment with stimulant medication that had been initiated in childhood or adolescence, and in early adulthood few cases (n=35 of the 476 cases or 7.4% of the cases retained in the long-term observational follow-up) had a Consistent pattern of long-term treatment from childhood through adolescence and into adulthood (see Swanson et al, 2017)[67], while n=112 (23.5%) had a Negligible pattern of treatment and n=329 (69.1%) had and Inconsistent pattern.

Oral administration of stimulant medication (methylphenidate or amphetamine) has an immediate beneficial effect and reduce symptoms for 2 to 3 hours. For decades, exemplary clinical treatment with stimulant medication (see Safer and Allen, 1976)[68] required multiple administrations of immediate-release formulations of amphetamine (e.g., twice a day) or methylphenidate (e.g., three time a day) to maintain efficacy across the day, due to short duration of action of immediate-release formulations of these drugs. This required administration in in public (i.e., in supervised school-settings that caused embarrassment and stigma and required scarce school resources). The first-generation sustained release formulation intended for once-a-day administration were ineffective for extending duration of action and were seldom used in clinical practice. (see Greenhill and Osman, 1991)[69]. Two decades ago tachyphylaxis (acute tolerance) to methylphenidate was discovered (Swanson et al, 1999)[70] and was later documented for amphetamine (Greenhill et al, 2003)[71]. Based on the theory of acute tolerance, pharmacokinetic and pharmacodynamic studies were conducted to evaluated how to overcome this property of stimulant medication, which led to the development of second-generation controlled-release formulations with ascending drug delivery for 8 to 10 hours that provided long duration of efficacy for once-a-day administration (see Swanson et al, 2002)[72]. The controlled-release formulations were based on a standard method to overcome tolerance (i.e., by increasing dose), which was achieved by controlled-release formulations that delivered an ascending drug delivery after a morning administration of methylphenidate via an oral release osmotic system (OROS) that was used to develop Concerta® (see Swanson et al, 2000)[73] or a coated-bead system that was used to develop Adderall® XR (see Greenhill et al, 2003)[74]. Since about 2000, these controlled-release formulations have essentially replaced the immediate-release formulations that had been used clinical for 60 years (see Swanson and Volkow, 2009)[75].

As outlined above, the primary treatment for ADHD is with stimulant medication, which serendipitously was discovered almost a century ago by Bradley (1937)[76] to be clinically effective by improving school performance and reducing disruptive behavior (i.e., age-inappropriate inattention and impulsivity with or without hyperactivity) that affects 5-10% of children worldwide (Polanczyk et al, 2014)[77]. In a majority of cases, symptoms persist into adolescence and adulthood and are associated with elevated risk for adverse outcomes (e.g., school problems, substance use, delinquency, etc.), so treatment is considered essential. Awareness, education, and research about ADHD increased public acceptance of diagnosis and treatment (see IDEA, 1994)[78]. In the 21st century, the incidence of clinical use has increased dramatically in most countries with substantial cross-national differences (Raman et al, 2019)[79]. In 2015, the annual administrative treatment prevalence across countries ranged from <0.5% to 10% for children and from <0.1% to 2% for adults. However, recent reviews of prescription records and observational follow-up studies have concluded that long-term adherence and persistence of use of stimulant medication to treat ADHD has remained poor (Gajria et al, 2014[80] and Ahmed and Aslani, 2013)[81]. Most children initiating treatment in discontinue use of stimulant medication in childhood or adolescence, and very few continue treatment consistently into adulthood even when symptoms persist (as recommended by professional guideline when ADHD is manifested as a chronic disorder). Discontinuation occurs even for exemplary treatment when it is individualized by initial dose titration to select the best dose and formulation (see Vitiello et al, 2001)[82] and regular monitoring to adjust prescribed medication by increasing dose or switching formulation (see Charach et al, 2004[83] and Zetterviqst et al, 2013[84]), and repetition of episodes of uninterrupted treatment is uncommon and when this occurs the typical duration is less than the initial duration (Miller et al, 2004)[85].

Effective treatment with stimulant medication requires titration to select an effective starting daily dose and regular monitoring and adjustment to maintain efficacy (usually with an increase in daily dose), which was provided for cases assigned to the Med and Comb groups in the RCT phase of the MTA. Modern clinical guidelines recommend long-term use of medication for as long as symptoms persist (see Plitska et al, 2007)[86], but this seldom occurs in clinical practice, and it did not occur in the MTA follow-up, either. By the 3 year follow-up, the percentage of cases being treated with stimulant medication in the 4 randomly assigned groups had converged, due to different patterns of starting and stopping use of stimulant medication, and the residual effects of random assignment had dissipated (as described above). In contrast to the dramatic secular trend of increasing cross-sectional administrative prevalence of use of stimulant medication (i.e., by 300% from the 1990 to 1994; see Swanson, Lerner, and Williams, 1995[87]) and continued linear increases over the decades since then (see Swanson and Volkow, 2009)[88], longitudinal estimates of adherence and persistence of medication use in the MTA was poor and the percentage of cases with continuation of medication use eventually was very low (<10%). Thus, compared to the cross-sectional trend in population administrative prevalence, the longitudinal evaluation of medication use in individuals showed the opposite trajectory (e.g., a dramatic decrease in the annual percentage of cases continuing treatment, with a majority of cases discontinuing treatment in the first year).

Premature cessation of medication is proposed a major reason for lack of long-term benefit (see Coghill, 2022)[89], and long-term benefit remains inexplicably difficult to document (see Molina and Swanson, 2020)[90]. Adverse outcomes remain common (e.g., low educational attainment, increased substance use, and other functional problems; see Faraone et al 2021)[91], and some studies even show a large decrease in longevity (see Barkley, 2020)[92]. Therefore, there is a critical unmet need for long-term effective treatment of ADHD.

As outlined in the recent commissioned debate (see Cortese, Swanson, and Coghill, 2019)[93], many reasons have been proposed for poor persistence of medication use. In the past, many clinicians considered poor compliance was due to inconvenience and stigma associated with the need for multiple daily administration of short-acting immediate-release formulations, but even when this was addressed and overcome by the development of second-generation controlled-release formulations that were effective for once-a-day administration (see Swanson et al, 2002)[94], poor adherence and persistence of medication use were still observed in long-term follow-up studies (see Swanson et al, 2017)[95] and in analyses of prescription records (see Miller et al, 2004[96]; Zetterqvist et al, 2013[97], and Wong et al, 2019[98]; Lawson et al, 2012[99]; Biederman et al, 2019[100]; and many others). Also, a typical assumption is that treatment as-usual in community settings is non-optimal (see Coghill, 2019)[101], but this has been addressed by development of clinical guidelines and algorithms for frequent monitoring and adjustments to prescribed medication. Recent analyses of the MTA follow-up indicated treatment as-usual has changed since the 1990s, and now for extended episodes of treatment, adherence remains high and regular dose increases are prescribed up-to the point of discontinuation (see Marcus and Durkin, 2011[102] and Swanson et al, 2023[103]). Thus, even though solutions were proposed and have been implemented in many modern clinical practices, and adequate frequency (average annual adherence) and intensity (average daily dose) are now relatively high and in line with national and international treatment guideline at least for the duration of episodes of uninterrupted medication use, the percentage of cases that discontinue medication use increases dramatically over time, and most childhood-onset cases discontinue medication in childhood or adolescence, and very few cases continue medication use into adulthood (as recommended for at least 50% of the cases with persistence of symptoms and impairment).

Recent reviews indicate adherence and persistence remain poor in modern clinical practice (even when controlled-release formulations have essentially replaced immediate-release formulations), and new analyses of long-term follow-up studies indicate continuation of medication use (even for a decade, with regular dose increases) is not associated with relative benefit compared to discontinuation or negligible use. Thus, new and innovative approach are needed, since treatment with higher daily dose and with controlled-release formulations (i.e., with two components, a bolus dose to elicit rapid clinical benefit and ascending drug delivery across the day to counteract acute tolerance), and regular monitoring to provide increases in daily dose to counteract a short-term tolerance) have not been successful in increasing long-term adherence and persistence of medication use.

Neurochemistry of Response to Stimulant Medication

Diverse findings from basic science studies suggest an etiological hypothesis that ADHD is associated with neural mechanism that results in a dopamine deficit that is considered to underlie behavioral and cognitive deficits of ADHD. Volkow et al (2017)[104] summarized studies of human brain chemistry and function conducted by applying positron emission tomography (PET) imaging to measure occupancy of dopamine receptors. Neural mechanisms of action of the approved stimulant drugs have been documented, which are considered to target a specific class of brain neurotransmitters (e.g., the catecholamines, dopamine and norepinephrine). Several methods have been used to investigate the effects of methylphenidate on the brain, including PET imaging. Volkow et al (2002)[105] provides a summary of a series of studies using this method, which (a) clearly identified involvement of dopamine regions (Volkow et al, 2009)[106], (b) tracked the time-course of effect at these neural sites of action for direct assessment of PK and PD effects (Volkow and Swanson, 2008)[107], and (c) documented changes after a year of clinical treatment of adults in the density of dopamine transporters in the caudate nucleus (CN) and nucleus accumbens (NaC) that recycle released dopamine, which is a likely correlate of long-term tolerance.

The primary neural site action of stimulant drugs (methylphenidate and amphetamine) is dopamine network in the striatal region of the human brain. These drugs are considered to be dopamine agonists because their administration increases this neurotransmitter by occupying the dopamine transporter that blocks the reuptake of dopamine when it is released. The initial study (Volkow et al, 1995)[108] provided an account for different responses to methylphenidate (i.e., behavioral and cognitive benefit provided by clinical treatment of ADHD) and cocaine (i.e., euphoria associate with substance abuse) despite the same brain site and mechanism of action (blockade of the dopamine transporter in striatal brain regions), based on different brain pharmacokinetic (PK) properties (a longer PK half-life for methylphenidate than for cocaine). A subsequent study (Volkow et al, 2007)[109] of treatment naïve adults with ADHD suggested consensus based on a previous report (i.e., that the ADHD diagnosis was associated with high dopamine transporter levels) was an artifact of treatment response that increased the level from lower to higher than normal. An additional study provided a detained description of the brain regions affected by clinical doses of methylphenidate, which PET imaging localized in specific components of the striatum (the nucleus accumbens and caudate nucleus) that are associated with attention and motivation (Volkow et al, 2009)[110]. A study of long-term treatment with stimulant medication of adults with ADHD used PET imaging that was repeated after a year of clinical treatment with stimulant medication, which revealed dopamine transporter density was increased in specific dopamine regions of the brain (the nucleus accumbens and caudate nucleus (Wang et al, 2013)[111].

Regulation of dopamine is complicated and involves several intricately connected brain nuclei, and Grace et al (2019)[112] provide a summary of processes that regulate tonic and phasic dopamine levels and are critical for the short-term and long-term effects of drugs that mediated neural effects, including the stimulant drugs that are considered dopamine agonists and neuroleptic drugs that are considered to be dopamine antagonists. Based on this knowledge, it is clear that methylphenidate blocks dopamine transporters in the CN and NaC, increasing tonic extra-cellular dopamine levels and increasing the short-term neural response, but over time a compensatory processes occurs that reduces phasic dopamine release, blunting the long-term neural response to methylphenidate. This is a likely correlate of long-term tolerance. It is clear that adherence and persistence of the use of stimulant medications are poor, and very few cases that initiate treatment in childhood continue medication use into adolescence or adulthood. One reason proposed for this is the development of tolerance to stimulant medications Grace (2001)[113] summarized a series of studies conducted that identified and characterized adaptive mechanisms of the dopamine systems of the brain associated with complex connections of brain nuclei. These studies show there are two classes of dopamine neurons, which are characterized by tonic firing that releases low levels of dopamine and sets the extra-synaptic level, and phasic firing that releases high levels of synaptic dopamine that is recycled by the dopamine transporter (Grace, 2000)[114]. The effects of stimulant medications on the phasic and tonic dopamine are governed by interacting effects, with immediate or short-term agonist effect on tonic dopamine levels (that are increased by blockade of the dopamine transporter or reversal of its action), which elicits compensatory long-term antagonist effects (decreased phasic firing and reduced response by the dopamine receptors (Goto and Grace, 2005)[115]. A decrease in the homeostatic level of tonic dopamine is sensitive to exposure to and duration of physiological stress, which has been proposed as factor that creates a dopamine deficit considered to be neurochemical characteristic of ADHD that can be corrected by immediate effects of stimulant medication (Goto and Grace, 2007)[116]. The regulatory properties of the tonic and phasic dopamine have been applied to account for the short-term agonist effects of stimulant medications that underlie the clinical benefit of treatment, and long-term effects that counteract the initial clinical benefit and underlie the emergence of long-term tolerance.

Modern sustained-release formulations of methylphenidate (Concerta® and Metadate®) and amphetamine (Adderall® XR®) are considered to be dopamine agonist drugs. Oral administration of these formulations consists of a bolus immediate-release (IR) component to elicit rapid clinical effects, followed by controlled sustained-release (SR) component for ascending drug delivery for 6 to 10 hours to counteract the emergence of acute tolerance and to provide long-duration of efficacy with once-a-day administration. Based on serum drug concentrations, PK/PD modeling suggested 24 hours between administrations would be sufficient to allow for complete dissipation of tolerance. However, carry-over effects on behavior and performance were documented in laboratory evaluations. Clearance of dopamine agonist drugs from the brain is slower than from blood, which may allow tolerance to accumulate with extended treatment and eventually undermine efficacy. Instead of delivering an increasing dose of the dopamine agonist drug to counteract acute tolerance, the SR component could be replaced with an alternative drug that is not a dopamine agonist, which could be titrated to maintain the initial effect of the IR component. This would provide a longer delay between the bolus doses of the dopamine agonist drug, allowing for dissipation of acute tolerance and avoiding carry-over effects. The three formulations of sustained-release stimulant medication (Concerta,® Adderall XR,® and Metadate CDR) were developed and approved two decades ago and are still frequently prescribed pharmacological treatments for ADHD. They were based on the concept of acute tolerance, and provide long duration of action for effective once-a-day administration.

However, as outlined above, adherence and persistence of use is still relatively poor. Laboratory school studies document that carry-over tolerance emerges during the $1^{st}$ week of treatment with second-generation sustained-release formulations, based on comparisons of surrogate measures from the laboratory school protocol, including the average symptom rating on the SKAMP rating scale and permanent product (PERMP) of the 10-minute math test (the number of problems completed correctly). In the laboratory school protocol, for subsets of cases evaluated across the day the trajectory of the average SKAMP rating is a marker for the trajectory of average phasic dopamine levels and the trajectory of the PERMP score is a marker for average trajectory of tonic dopamine levels.

Observational follow-up studies document high adherence and regular increases in daily dose for subsets of cases during episodes of uninterrupted use of medication, but this does not result in significant long-term benefit (decreased ratings of symptom severity) compared to cases with negligible use of medication. Transition of medication status after discontinuation of uninterrupted adequate medication use does not result in a significant increase in ratings of symptom severity during the subsequent episodes of uninterrupted inadequate or no medication use.

Possible alternatives are non-stimulant drugs that are approved for treatment of ADHD, including atomoxetine, guanfacine, clonidine, and mazindol. Also, modafinil is approved for the treatment of narcolepsy and sleep disturbances associated with shift-work, and it has been documented to be effective for the treatment of ADHD. However, to extend duration of action of the IR formulation, dose was increased in the initial efficacy trials, and at high dose a few cases were suspected of serious dermatologic side effects (Steven-Johnson syndrome). Rather than conduct very large trial to discount this rare side effects, the request for approval was withdrawn. The neural mechanisms of action of the approved non-stimulant medication are less well-established.

New Insights About Homeostatic Properties of Dopamine

Proposals are provided here based on insights about long-term neural responses to stimulant drugs, and the realization that application of the standard approach (i.e., increasing dose) is counter-productive in the long-term, and inevitably results in long-term tolerance that undermines long-term efficacy. An alternative is proposed based on retaining a bolus dose of stimulant medication to elicit a rapid response, and replacing the subsequent ascending delivery (that overcomes initial tolerance but elicits long-term tolerance) by a non-stimulant drug, delaying the next bolus to allow for dissipation of tolerance.

Neuroanatomical and neurochemical models of ADHD and models of neural processes propose underlying neural response at sites of action, which suggest stimulant medication are dopamine-agonists drugs with specific anatomic sites of action. Stimulant medications (methylphenidate and amphetamine) are rapidly absorbed and are taken by blood flow to dopamine (DA) synapses in specific brain regions (e.g., the caudate nucleus), which can be monitored by Positron Emission Tomography (PET) imaging, which uses special compound (ligands) labeled with radioactive isotopes that emit signals that are detected by the PET imaging device and are used to localize their location in the brain.

The hypothesis underlying the use of stimulant medication to treat ADHD is that these drugs are DA agonists (and increase the action of this neurotransmitter by blocking the DA Transporter (DAT) that recycles released DA and increases the synaptic level, which propagates neural transmission (Volkow et al, 2002)[117]. Homeostatic processes that maintain levels of synaptic DA are engaged, including the increase in density of DAT (see Volkow et al, 2007)[118]. In adults with ADHD, consistent treatment with methylphenidate (i.e., a potent DA agonist drug) increases DAT density over a year of consistent medication use (Wang et al, 2013)[119].

The acute treatment of ADHD with stimulant medication is associated with acute tolerance (tachyphylaxis), which requires increases in the concentration of the drug at the site of action in the brain to maintain efficacy across the day. For the OROS® formulation designed for Concerta®, the ascending drug delivery was programmed to terminate after 8-10 hours, which was intended to allow for dissipation of acute tolerance and to prevent carryover tolerance to the next day. However, Swanson (2012)[120] summarized PK/PD studies and suggested acute tolerance does not dissipate completely overnight, and carry-over tolerance emerges across 7 days of treatment that must be overcome when the next dose is administered the next day. The increased density of DAT is presumed to be a mechanism that contributes to long-term tolerance.

The recognition of Attention-Deficit/Hyperactivity Disorder (ADHD) in the worldwide population has been increasing for decades (e.g., from <3% of school aged-children in 1990 to ~10% of children and 5% of adults by 2020; see Faraone et al, 2021)[121], and use of stimulant medication to treat ADHD has been increasing also (e.g., by 500% from 1990 to 2020; see UN-INCD, 2020)[122]. These high recognition and treatment rates have been justified by evidence of relative efficacy (greater decrease in symptom severity for treatment with medication compared to alternatives) in rigorous reviews of randomized controlled trials (Storebo et al, 2015[123] and Cortese et al, 2018[124]), with large-to-medium average effect size in many short-term trials (≤3 or <6 months) for children (~0.8) and adults (~0.5), and medium-to-small in long-term trails (>1 year) for children (0.47) and adults (0.21). Since ADHD is usually a chronic condition associated with a variety of adverse functional outcomes (see Bhat and Hechtman et al, 2016)[125], clinical practice guidelines recommend continuation of treatment for as long as symptoms of ADHD continue (i.e., through adolescence and into adulthood in a majority of childhood-onset cases). But, significant long-term relative benefit for extended treatment with stimulant medication has been difficult to document for a variety of reasons (see Molina and Swanson, 2020)[126], including decreasing efficacy and increasing discontinuation over time. Recent reviews of prospective observational follow-up studies and retrospective studies of prescription records (Gajria et al, 2014[127] and Ahmed and Aslani, 2013[128]) indicate the average duration of adequate treatment with stimulant medication is surprisingly low (<1 year). In contrast to dramatic increases in cross-sectional estimates of population prevalence, longitudinal estimates of adherence and persistence of medication use in individuals have not changed since the 1970s. There is a critical unmet need for a pharmacologic treatment of ADHD that will remain effective and will not be inappropriately discontinued (see Charach and Fernandez, 2013)[129].

As summarized previously, recently Cortese (2019)[130] commissioned a debate to address the issue of long-term benefit. Coghill (2019)[131] proposed exemplary clinical care based on the MTA medication algorithm (with frequent monitoring and regular dose increases to maintain efficacy), resulting in good adherence and persistence and long-term relative benefit. In contrast, Swanson (2019)[132] proposed even for exemplary clinical care, unrecognized and unappreciated long-term tolerance would inevitably emerge for long-term treatment with stimulant medications (considered to be dopamine agonist drugs), undermining long-term efficacy and resulting in poor adherence and persistence and complete dissipation of relative benefit. New analyses and insights regarding long-term use of stimulant medication and pharmacodynamic and homeostatic properties of neural response to dopamine-agonist drugs are presented here, which suggest innovative pharmacological approaches to avoid long-term tolerance. One solution is based on retaining the first component of available controlled-release formulations (i.e., a titrated bolus dose of stimulant medication to elicit rapid but temporary reduction of symptoms) and replacing the second component (i.e., ascending delivery of stimulant medication to counteract acute tolerance) with a non-dopamine agonist drug, titrated and delivered to maintain efficacy but to avoid carry-over and accumulated tolerance that undermine long-term efficacy.

Most formulations of stimulant medications (considered to be dopamine agonists drug) have an initial bolus component and a second controlled-release component. The prime examples that have been used for about 20 years are Concerta® (for methylphenidate) and Adderall® XR (for amphetamine). The first component of controlled-release formulations of methylphenidate and amphetamine have the advantageous property of rapid onset, so a child with ADHD can take the medication in the morning and it will have the full effect almost immediately. The second component is designed to maintain the full effect across the day.

Other formulations of these two stimulant medications have similar drug delivery profiles Also, there are several non-stimulant medications that have been developed for the treatment of ADHD, including, but not limited to, atomoxetine, guanfacine, and clonidine.

Examples of formulations with a bolus dose as the first component include:

Concerta. This formulation of methylphenidate was designed for once-a-day administration based on the osmotic release oral system (OROS). It has an "overcoat" of immediate-release methylphenidate that provides a bolus component that allows for a fast or unimpeded absorption of the drug according to the pharmacokinetic (PK) properties of this drug (i.e., for methylphenidate, relatively rapid absorption after oral administration with a maximum serum concentration or C-max level achieved in about 1 hour). The drug is metabolized and the half-life or T-½ value is about 2-3 hours, which represents the time required for the serum concentration to decrease by 50% from the maximum level achieved by the bolus component. For decades before the development of Concerta®, bolus doses of methylphenidate were administered multiple times a day (e.g., every 3 to 4 hours or two to three times a day). For equal bolus doses, the carry-over effect of the first bolus (added to the effect of the second and subsequent bolus doses) resulted in an ascending profile across the day (but with peaks and troughs), which was effective for maintaining the full effect of stimulant medication across the school day. The PK profile for the twice-a-day (BID) dosing is shown in the solid line in FIG. 1A. Concerta® replaced this with the OROS system that provided a bolus dose in the morning (the first component), followed by an ascending delivery of medication across the day (the second component) to counteract acute tolerance (see below) that surprisingly occurred when the second bolus dose was reduced to maintain a constant level based on the addition to carry-over (see FIG. 1a).

Metadate-CD. This medication is based on a combination of uncoated and coated beads of methylphenidate. It has uncoated beads of immediate-release methylphenidate that provide a bolus component, which also allows for rapid unimpeded absorption based on the pharmacokinetic properties (i.e., relatively rapid absorption after oral administration with a maximum serum concentration or C-max achieved in about 1 hour, with a half-life (T-½) of about 2-3 hours. This formulation also produced a rapid initial pharmacodynamic effect based on the pharmacokinetic properties of this drug (based on the first component), and then maintained the effect across the day with the second component (coated beads). The first component (the bolus dose) provided about the same initial effect as Concerta®, but the second component maintained the effect for 6-8 hours rather than 10-12 hours.

Adderall-XR. This medication also is based on uncoated and coated beads of a different stimulant drug (an amphetamine mixture of d- and l-amphetamine). This formulation has uncoated beads of immediate-release amphetamine that provide the bolus component, which produces a rapid initial effect based on the pharmacokinetic properties of this drug. Amphetamine has a relatively rapid absorption after oral administration with maximum serum concentration or C-max level achieved in about 2 hours, and a longer half-life or T-½ value of about 3-4 hours). Based on the longer half-life, twice-a-day or BID dosing (with the addition to the carry-over from the first bolus) was sufficient provided a constant effect for 10-12 hours that matched the duration of action of TID dosing of methylphenidate (see FIG. 1B).

Other Formulations. Over the past 20 years, several formulations of methylphenidate and amphetamine have been developed and approved for the treatment of ADHD, which have bolus components based on various methods to allow for rapid absorption and fast onset of effect associated with an immediate-release bolus (the first component), followed by controlled-release to maintain the effects across the day (the second component). Other (non-stimulant) drugs, which do not all have the rapid onset after an initial (bolus) dose similar to methylphenidate and amphetamine, and may have longer PK half-life values, may not require the two-component drug delivery that has been described above.

The second component of controlled-release formulations of the two stimulant medications (methylphenidate and amphetamine) are designed to deliver an ascending profile of drug across the day, which is considered to be necessary to counteract acute tolerance that occurs after administration of these medications (that primarily target the neurotransmitter DA).

Examples of controlled-release formulations with an ascending (or equivalent) component include:

Concerta. This formulation was designed for once-a-day administration, which was intended to provide the same duration and efficacy of immediate-release methylphenidate administered three-time-a-day in equal bolus doses (see FIG. 2, part A). Concerta® is based on the osmotic release oral system (OROS) that has a reservoir of methylphenidate contained inside of semi-permeable membrane along with polymer that expands in the presences of water, The membrane has a laser-drilled hole at the end that contains the drug. As water moves through the membrane, it expands the polymer and creates pressure to pump the medication out through the opening. In contrast to previous formulations (see FIG. 2, part B), the system for Concerta® was designed to deliver the second component of medication at a programmed "ascending" rate (see FIG. 2, part C) as the OROS device moves through the stomach and intestines for a fixed period not time, and then the drug delivery is stopped. The ascending rate of drug delivery is programmed to counteract acute tolerance, which occurs when the drug reaches it site of action and an adaptation process occurs (see below). Due to this process, the effect of a constant concentration over the day is reduced over time, so an increasing concentration is required to maintain the full effect elicited at the time when the maximum level or C-max is achieved (i.e., T-max). The time before the next dose of medication was assumed to be long enough for acute tolerance to dissipate in late in the evening (see FIG. 2, part C) before the next dose in administered the next morning.

Metadate-CD. This formulation based on coated and uncoated beads. The coated beads created a barrier that delays the release of drug in the coated beads. The coating I can be varied, and thus can be designed to provide programmed delivery of methylphenidate to achieve an ascending level of medication for a fixed period of time.

Adderall-XR. This formulation is also based on coated and uncoated beads, which allow for the controlled delivery of this medication and an ascending level across the day.

Other Formulations. Other formulations of methylphenidate and amphetamine have slightly different properties, but they are designed to delay the second component and deliver the drug via the second component to achieve an ascending profile, which is considered necessary (due to acute tolerance) to maintain the full effect across 8 to 12 hours.

The pharmacodynamic (PD) effects of controlled-release formulation of methylphenidate (i.e., effects of the drug on the body, primarily on the neurotransmitter DA at the site of action in the brain) are summarized in FIG. 2. This shows the predicted effects at the site of action in the brain for three-times-a-day [TID] bolus doses (see FIG. 2, part A), for small constant doses after a bolus (see FIG. 2, part B), and for small ascending doses across the day for an approximation of the drug delivery profile for OROS-methylphenidate (see FIG. 2, part C). These graphs show the predicted effects on DA in the brain that are expected to mediate the clinical effects on behavior (i.e., symptoms of ADHD) and on cognition or attention (i.e., on productivity on laboratory or school tasks). The neural effects are based on the process of methylphenidate attaching to the dopamine transporter protein at the site of action in the brain, which prevents the re-update of released DA, and thus increasing the availability of this neurotransmitter to activate the DA receptor and propagate neural activity in the brain.

There are two classes of dopamine receptors that are distinguished by their location at the synapse (presynaptic and postsynaptic). The properties and characteristics of activation and rates of neural propagation (firing) are known for presynaptic DA (tonic firing) and postsynaptic DA (phasic firing) receptors. The effects are summarized in FIGS. 3A, 3B and 3C, which show the effects of an acute dose of methylphenidate on tonic and phasic DA after oral administration when the drug reaches the brain site of action (see FIG. 3A), after DA escapes from the synapse and reached the presynaptic DA receptor, and across the day as dynamic effects occur and alter the subsequent release of DA (see FIG. 3B). Dynamic effects occur associated with the action of the drug (methylphenidate) on DA transporters, which affected the level of DA in the synaptic gap as well as surrounding the synapse (when the DA transporter does not recycle the DA after it is released). Eventually, the level of presynaptic DA regulates the amount of DA released, altering the levels that are present across the day (as shown in FIG. 3C) via a homeostatic mechanism that acts to preserve levels of DA in the brain. The initial increase in DA associated with the blockade of the DA transporter has a homeostatic effects of decreasing release, which reduces the DA level (i.e., an "antagonist" net effect after the initial increase in DA (i.e., an "agonist" effect).

Figure 3A:
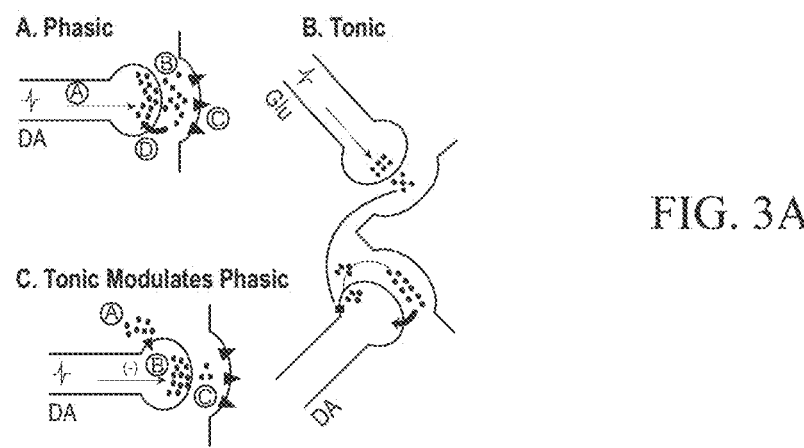
FIG. 3A: Effects of an acute dose of methylphenidate on tonic and phasic dopamine when the drug reaches the brain site of action.
Figure 4A:
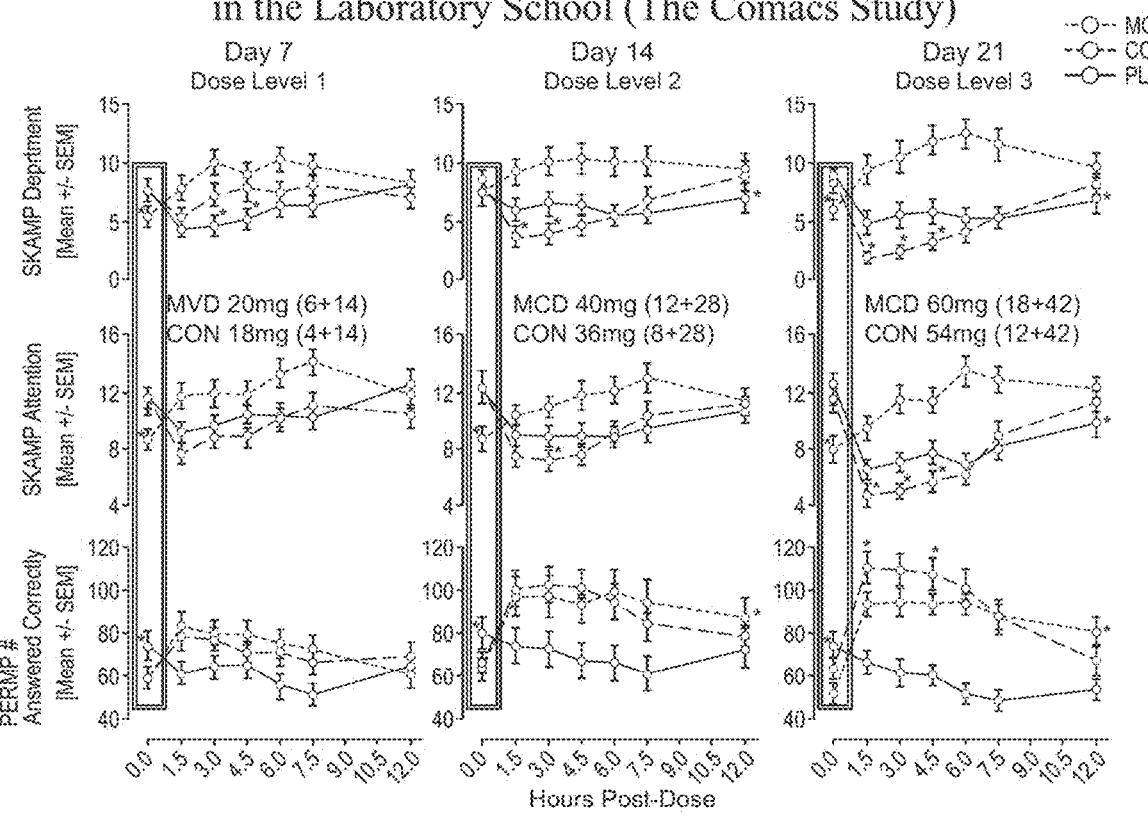
FIG. 4A: Comparison of extended-release methylphenidate formulations in children with ADHD.
Figure 4B:
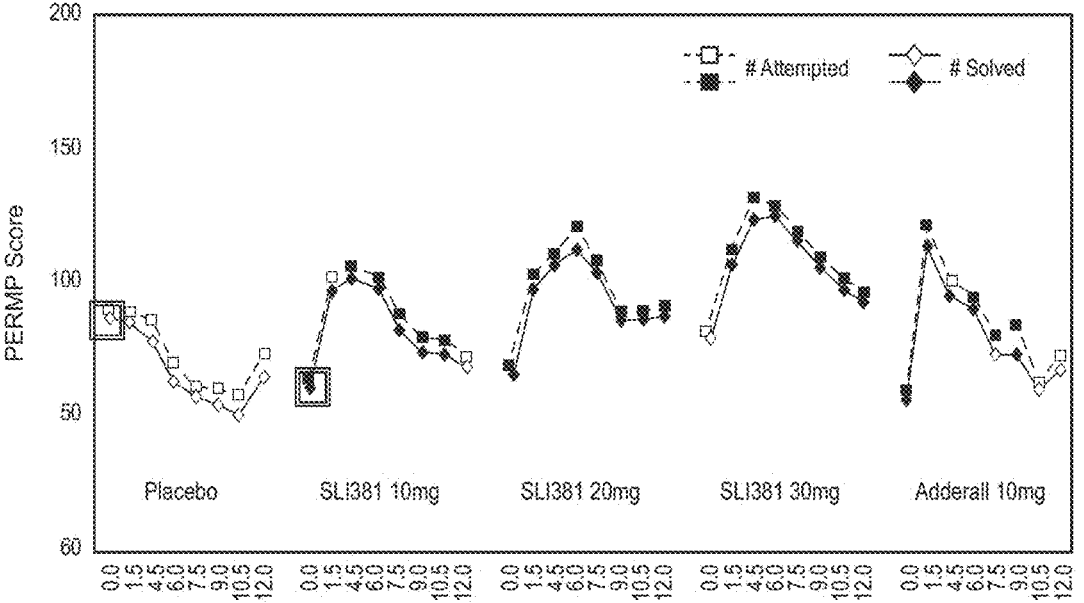
FIG. 4B: Comparison of extended-release amphetamine formulations.

FIG. 3A provides an illustration of the tonic/phasic model of DA system function. Part A. Phasic DA release: This high-amplitude DA release process is triggered by DA neurons firing (A) leading to calcium-dependent DA release into the synaptic cleft (B) where it reaches sufficiently high concentrations (i.e. up to mM) to stimulate postsynaptic DA receptors (C). The DA is then rapidly removed from the synaptic cleft by the DA transporter (D) before it can escape into the extrasynaptic space. Part B: Tonic DA: Tonic DA is the low-concentration but tightly regulated DA present in the extrasynaptic space. This DA level is derived from two sources: 1) it is modulated by glutamatergic afferents in close proximity to the DA terminal Glutamate released from these terminals (A) stimulates presynaptic glutamate heteroreceptors on the DA terminal (B) to release DA from an intraterminal pool distal from the synaptic cleft (D) to contribute to this pool, particularly during periods of slow spike discharge. This extrasynaptic DA (E) is maintained at low (mM) concentrations. Part C: Tonic modulates Phasic: The tonic extracellular DA pool (A) is too low in concentration to stimulate postsynaptic DA receptors. Nonetheless, it is of sufficient amplitude to provide a tonic down-modulation of spike-dependent DA release (B) by stimulating release- and synthesis-modulating DA autoreceptors on the DA terminal. This causes a decrease in spike-dependent DA release into the synaptic cleft (C).

Figure 3B:
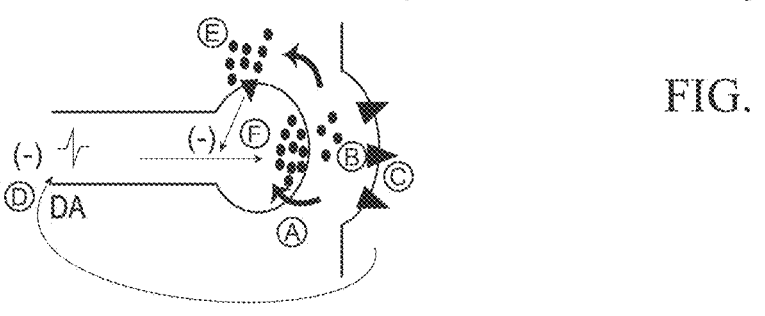
FIG. 3B: Effects of an acute dose of methylphenidate on the system following administration.
Figure 3C:
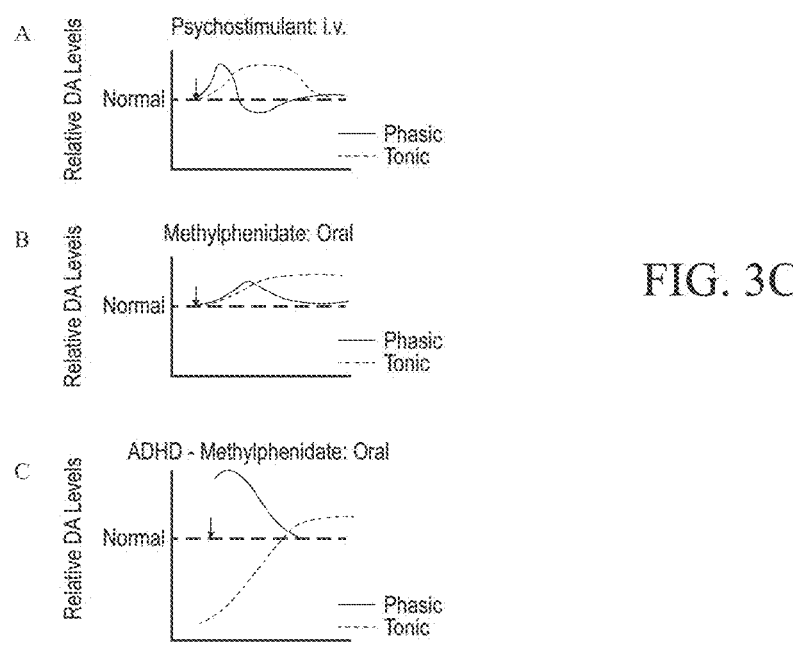
FIG. 3C: Relative levels of tonic and phasic dopamine from methylphenidate bolus dose.

FIG. 3B illustrates a model of methylphenidate actions. By blocking the DA transporter (A) methylphenidate will cause an accumulation of DA in the synaptic cleft (B). Although this may initially cause increased stimulation of postsynaptic DA receptors (C), in the long term the consequence is a down-regulation of DA release. This occurs via several processes. First, increased postsynaptic DA stimulation will cause a feedback inhibition of DA neuron firing (D) to decrease spike-dependent DA release. More significantly, the blockade of DA uptake will enable much larger quantities of DA to escape from the synaptic cleft and accumulate in the extrasynaptic space (E). This will substantially increase presynaptic DA autoreceptor stimulation, resulting in a potent attenuation of spike-dependent DA release (F). The result is a dramatic decrease in the concentration of DA that is released into the synaptic cleft (B) thereby decreasing the amount of phasic DA that can be released upon activation of DA neuron firing.

FIG. 3C illustrates a model of psychostimulant drug action in treatment of ADHD, as derived from the tonic/phasic model of DA system function. The "normal" level of tonic and of phasic DA transmission in control individuals is indicated as a horizontal dashed line in each case. (A) The response of a control individual is indicated to a psychostimulant administered intravenously. In this case, the psychostimulant causes a rapid rise in phasic DA transmission (solid line). This is due to the blockade of the reuptake process and consequent potentiation of spike-dependent DA release. The increase in phasic DA produces the rapid behavioral activation (or feelings of euphoria) associated with intravenous psychostimulant administration. This is followed by efflux of the released DA from the synaptic cleft, and accumulation in the extra synaptic space as tonic DA (dotted line). The increased tonic DA causes an inhibition of spike-dependent phasic DA release, causing the phasic DA response to dip below baseline before returning to control levels. (B) The response to oral doses of methylphenidate. In contrast to the intravenous route of administration, the oral dose has a much slower onset of action. As a consequence, the phasic response is more blunted, since the slow onset preferentially augments tonic DA by allowing diffusion of DA from the synaptic cleft (the phasic component) into the extracellular space (the tonic component).

The effects of these other (non-stimulant) drugs are mediated primarily by other neurotransmitters (other than DA), and are not subject to dynamic homeostatic effects (which are special characteristics of the DA system). Thus, they are not associated with the development of acute tolerance across the day after oral doses (as described and summarized in FIG. 2).

Also, the effects of controlled-release formulations of methylphenidate (Concerta®, Metadate CD, etc.) and amphetamine (Adderall® XR, etc.) provided effects that continued across the day, as planned, but the expected dissipation of acute tolerance in the evening (or at least before the next dose on the following morning) did not occur as predicted (see FIG. 2C). Instead, there was evidence of carry-over tolerance the next morning for controlled-release methylphenidate (see FIG. 4A) and controlled-release amphetamine (see FIG. 4B). In the laboratory school protocol that evaluates the effects of a week of treatment on the 7th day. The measures of behavior (ratings on the SKAMP scale) and performance on an academic task (the 10-minute math tests) show carry-over effects on the test before medication is administered in the morning (i.e., a negative effect), which is overcome when medication is administered. The carry-over effect was unexpected, but provides evidence that acute tolerance does not dissipate at the same rate that is builds up over the day.

As a result of carry-over tolerance, in the long-term use of controlled-release stimulant medications (e.g., Concerta®, Adderall® XR, etc.), the emergence of long-term tolerance is expected to accumulate and undermine long-term benefit. This provides the basis for the proposed new strategy to replace the controlled-release component of the currently available formulation with a non-stimulant medication. This is intended to allow more time after the bolus dose for the acute tolerance to dissipate before the next bolus is administered on a subsequent day.

Figure 5A:
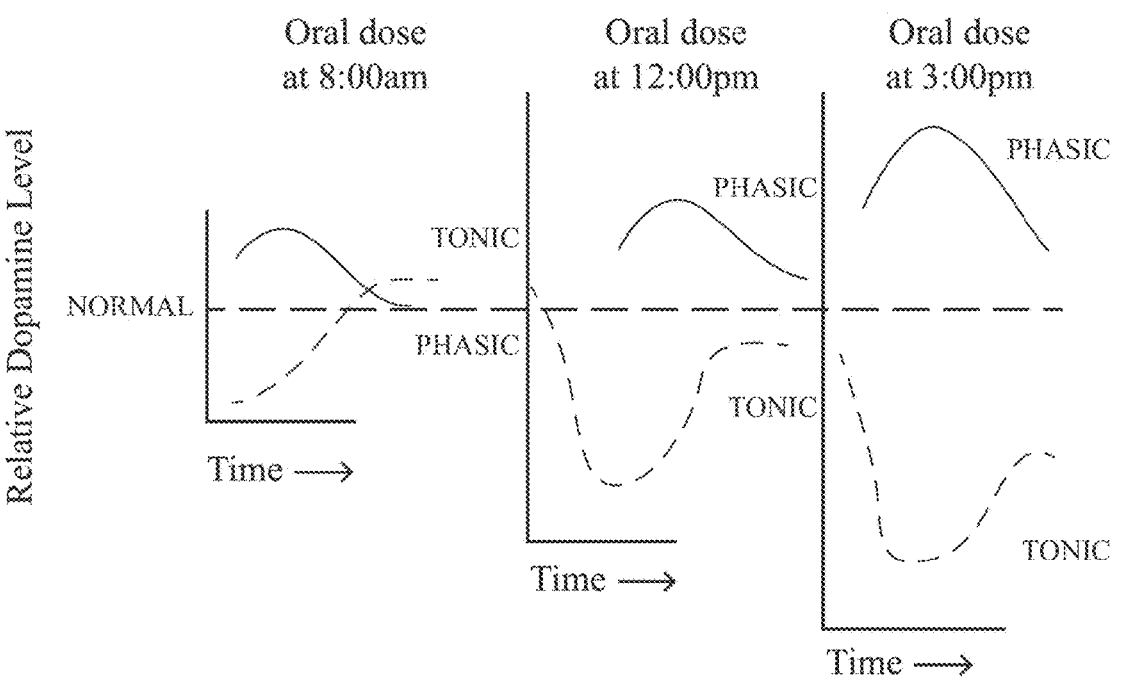
FIG. 5A: Schematic representation of accumulation of tolerance for extended-release methylphenidate illustrating tonic and phasic dopamine (DA) levels in the brain after oral doses of methylphenidate—dynamic effects that accumulates and results in acute tolerance
Figure 5B:
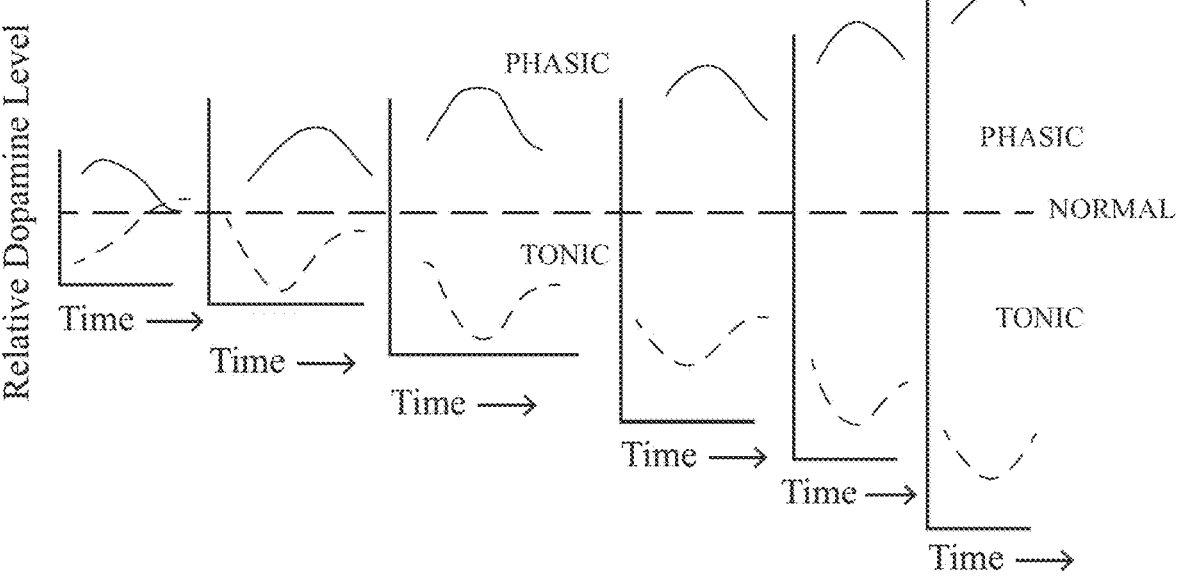
FIG. 5B: Schematic representation of accumulation of tolerance for extended-release methylphenidate illustrating tonic and phasic dopamine (DA) levels in the brain across days after oral doses of methylphenidate that continue to accumulate and results in long-term tolerance
Figure 5C:
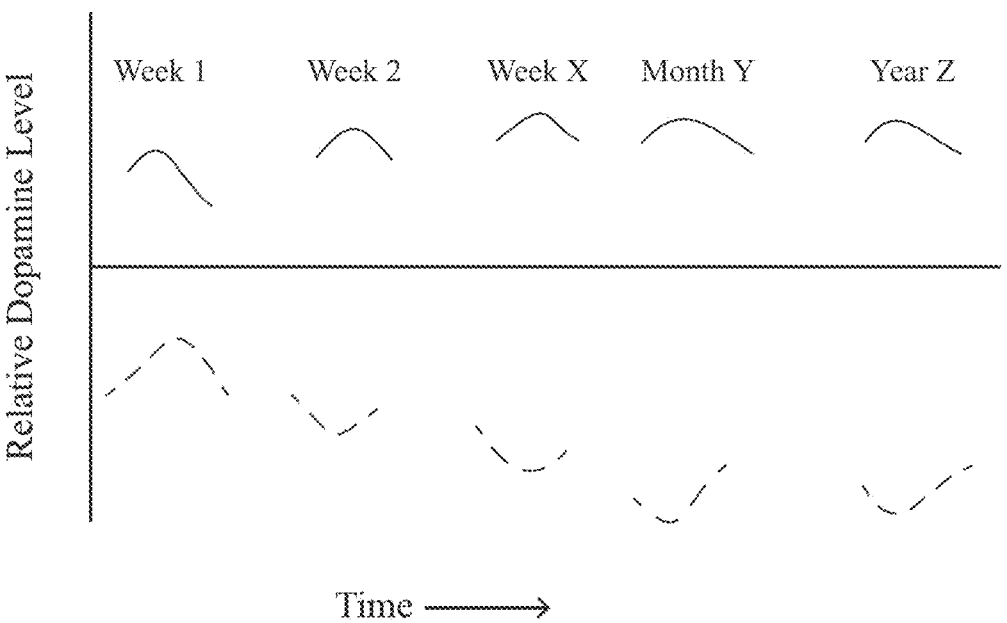
FIG. 5C: Schematic representation of accumulation of tolerance for extended-release methylphenidate illustrating tonic and phasic dopamine (DA) levels in the brain across weeks, months and years of oral doses of methylphenidate that accumulates and results in long-term tolerance

As stimulant medications are continued, the carry-over tolerance accumulates, as shown schematically in FIGS. 5A, 5B, 5C for extended-release methylphenidate. FIG. 5A is for multiple doses within a day; FIG. 5B is for doses across days; and FIG. 5C is for doses across weeks, months, or years. The level of tonic DA in the brain (which regulates the amount of DA released) decreases to an asymptote, and due to the increases in DA release, the level of phasic DA increases to an asymptote. The relationship to "normal" levels of DA are shown. The initial oral doses of methylphenidate "normalize" DA levels, but eventually tolerance undermines the clinical benefit as the DA levels return to the abnormal state that is characteristic of ADHD. Pharmacological Treatment Of ADHD:

Individuals with physical and mental disorders have clinical needs that are amenable to pharmacological treatment. When a specific clinical need is present (specified by a diagnosis), specific drugs may be associated with potential benefits that are greater than possible harms. When a drug for treatment of a disorder meets standard criteria for efficacy (significant benefit) and safety (non-significant harm), approval can be sought from and granted by regulatory agencies for approved use as a medication to treat the disorder.

An example of a mental disorder is provided by attention deficit hyperactivity disorder (ADHD), which is the most frequently recognized and treated psychiatric disorder of childhood (see Polanczyk et al, 2014)[133]. An extensive literature (see Faraone et al, 2021)[134] traces historical references to this condition, and the refinement of modern diagnosis as it evolved from hyperkinetic reaction of childhood in DSM-II (1968)[135], which was recognized in <1% of school-aged children, to ADHD in DSM-5 (2013)[136], which is now recognized in ~10% of children 5 to 18 years of age and ~5% of adults >18.

Over 80 years ago, the initial treatment of ADHD-like behavior was with amphetamine (Benzedrine® and Dexedrine®) that was used to treat children in a residential school with behavioral disturbances (Bradley, 1937[137] and 1950[138]). Methylphenidate (Ritalin®) was developed by CIBA Pharmaceuticals in the 1960s and became the primary medication used to treat the childhood disorders labeled hyperkinetic reaction of childhood (DSM-II, 1968)[139] and minimal brain dysfunction (Wender, 1971)[140], which were diagnostic labels of the era. Since these stimulant drugs were considered to have abuse potential, the clinical use to treat children with behavior and learning problems was controversial, and there was concern about diversion from clinical to illegal use. When the modern regulations were developed in 1970 for the FDA (see Greenhill and Osman, 1991)[141], methylphenidate and amphetamine were classified "Schedule II" drugs and the supply and use were highly controlled.

Safer and Allen (1976)[142] provided a summary of standard of care in clinical practice prior to the ground-breaking changes in diagnosis of Attention Deficit Disorder (ADD) without or with Hyperactivity (ADDH) provided by the third revision of the Diagnostic and Statistical Manual (DSM-III, 1980)[143]. The available formulations of methylphenidate and d-amphetamine that were usually prescribed (Ritalin® and Dexedrine®) had rapid onset of clinical effect (e.g., reduction in symptoms) within an hour of oral administration and short duration of action with gradual dissipation of clinical benefit across 3 to 4 hours. Shaywitz et al (1982)[144] and Swanson et al (1978)[145] documented that the pharmacodynamic (PD) properties of clinical effect paralleled the pharmacokinetic (PK) properties in blood (e.g., time of the maximum or peak serum concentration of the drug and the half-life or time for the peak serum concentration to decrease by 50%). Typically, to maintain clinical benefit across the day, multiple administrations of the immediate-release formulations of methylphenidate and amphetamine were necessary.

The level and range of per-administration doses of these drugs differed (e.g., 10 to 20 mg for methylphenidate and 5 to 10 mg for d-amphetamine). There was considerable variation across individuals, but the optimal dose did not seem to depend on age or weight, so absolute (mg) rather than relative (mg/kg) dosing was used. When titrated to determine the best dose based on efficacy and side effects, these drugs were considered to provide equivalent clinical benefits. After titration, an initial adjustment of dose was sometime required in the first weeks or months of treatment, but when an effective dose was established for an individual, additional tolerance was not observed and the dose for chronic use was expected to remain stable (see Safer and Allen, 1989)[146].

In the 1970 and 1980s, twice-a-day administration was typical for methylphenidate and amphetamine. Usually, the second administration was "sculpted" based the pharmacokinetic (PK) properties of the drugs. For multiple oral administrations 3 to 4 hours apart across the day, carry-over levels of the drug in the blood stream (and eventually reaching the site of action in the brain) were expected, so the reduced second dose administered was expected to provide a stable clinical effect. However, laboratory evaluations of PK and PD properties of stimulant medications were developed and applied to measure the time-course effect (see Swanson et al, 1978[147] for a summary), which suggested sculpted dosing would result in partial dissipation of full benefit in the afternoon. Based on this, the long-standing clinical practice of sculpting the daily administrations was questioned (see Swanson et al, 1991)[148], and non-sculpted regimens of methylphenidate (characterized by PK profiles with a series of ascending peaks and troughs) were recommended to provide stable PD effects for long durations of 8 to 10 hours.

Inconvenience associated with multiple administrations across the day and stigma associated with taking medication at school led to a search for alternative stimulant drugs that could be administered once-a-day. Two alternatives were approved for use, pemoline (Cylert®) and a 75%/25% mixture of the d- and l-optical isomers of amphetamine (Adderall®), which had longer PK half-lives than methylphenidate or d-amphetamine. However, evaluation of the PD properties of these alternatives medications was conducted in a laboratory school setting with hourly assessments of behavior and performance, which indicated Cyclert® (see Pelham et al, 1997)[149] and Adderall® (see Swanson et al, 1998)[150] had slightly longer durations of actions (4 to 6 hours), indicating once-a-day administration would not be sufficient to provide stable effects to cover the full day (i.e., 8 to 10 hours).

When the Multimodal Treatment Study of ADHD (MTA) was initiated in 1993, a committee reviewed clinical practice and specified state-of-the-art treatment with stimulant medication, and dose-titration with a sculpted three-times-a-day (TID) regimen of immediate-release (IR) methylphenidate was recommended (see MTA Group, 1999)[151], which was assumed to provide a stable clinical benefit across the day. Based on this clinical consensus (which may have been already outdated but was still accepted by most investigators), once the best dose was established, it was assumed that the optimal level would remain constant over time. However, during the first year of treatment by-protocol, adjustments in daily dose of medication (intended to maintain full effectiveness of treatment by-protocol) were made, and in a majority of cases, dose was increased (Vitiello et al, 2001)[152].

In the 1970s and 1980s, first-generation sustained-delivery formulations were developed and approved for methylphenidate (Ritalin SR®) and amphetamine (Dexedrine Spansules®). These early formulations were intended for once-a-day administration, and the targets were based on the sculpted regimens for IR formulations (that were assumed to achieve constant effects across the day by maintaining constant serum concentrations of the drugs. However, in clinical practice they did not provide a stable or extended duration of action and were seldom used (see Greenhill and Osman, 1991)[153]. Therefore, in 1990s when the use of stimulant medication to treat school-aged children in the USA suddenly increased dramatically from ~1% in 1990 to 3% in 1993 (Swanson, Lerner, and Williams, 1995)[154], there was public controversy and scientific concern about stigma and resources associated with administration of a controlled substance in public (i.e., at school) and the inconvenience of multiple administrations, and there was a critical unmet need for a controlled-release formulation for once-a-day administration that would maintain full benefit across the day. Pharmaceutical companies realized this, and initiated research programs to develop new approaches for designing and creating effective once-a-day formulations of stimulant medication for the treatment of ADHD.

Diverse findings across multiple studies based on the laboratory school protocol suggested that the PD effects of stimulant medications may be associated with the rapid emergence of tolerance. The literature on clinical effects of the first-generation SR medication indicated that controlled-release formulations developed to mimic the PK profiles of sculpted doses of immediate-release formulations of stimulant medications (which had been used for decades) did not maintain full efficacy across the day (Greenhill et al, 1987)[155]. Studies in the laboratory school setting with non-sculpted regimens (three equal doses of methylphenidate) resulted in a PK profile of serum concentrations across the day with a series of increasing peaks and troughs, which did maintain full effectiveness (Swanson et al, 1991)[156].

Swanson et al (1999)[157] applied the laboratory school protocol with surrogate measures of symptoms (SKAMP ratings of classroom behavior) and performance (time to complete 25 math problems) in a proof-of-principle study of the concept of acute tolerance (tachyphylaxis) to methylphenidate. In an innovative study, small oral doses given every 30 minutes (a variant of the "sipping" study), different patterns of administrations were used to establish a predicted constant (flat) or increasing (ascending) PK profile across the day. A decreasing effect (PD response) was observed across the day for the flat profile and an increasing effect was observed for the ascending profile. In a subsequent study, the same serum concentration (PK exposure) was established after high or low peak concentrations, and a time-coded analysis of PD effects versus PK levels indicated hysteresis loops that suggested the rapid emergence of tolerance (tachyphylaxis).

The proof-of-principle study led Alza Pharmaceuticals to develop a sustained-release (SR) formulation of methylphenidate (Concerta®) based on the Oral Release Osmotic System (OROS®), which delivered a bolus dose of IR methylphenidate followed by increasing amounts of methylphenidate across the day (Swanson et al, 2003)[158]. This drug delivery pattern (based on the concept that gradual dose-increases would produce an ascending PK profile that would counteract the emergence of acute tolerance) maintained PD efficacy for 10-12 hours. This second generation SR formulation of methylphenidate was enthusiastically accepted in clinical practice for once-a-day treatment, and soon after approval Concerta® essentially replaced multiple daily administrations of the IR formulations of methylphenidate and amphetamine.

Medeva Pharmaceuticals applied the laboratory school protocol to evaluate a coated-bead formulation of methylphenidate with 30%/70% mixture of IR and SR beads, which produced an ascending serum concentration profile (Swanson et al, 2004[159] and Wigal et al, 2003[160]). This provided a similar but shorter duration formulation of methylphenidate and was approved as Metadate CD,® but it was not as well-accepted for clinical use as the longer acting formulation (Concerta®). The laboratory school protocol was applied by CIBA/Novartis Pharmaceuticals to develop Ritalin LA® and by Celgene/Novartis to develop Focalin SR®, but eventually these controlled-release formulations were based on equal mixtures of IR and SR beads, which did not provide ascending serum concentration profiles. These controlled-release formulations were not well-accepted in clinical practice.

Richwood and Shire Pharmaceuticals applied the laboratory school protocol to evaluate the PK and PD effects of Adderall® (Swanson et al, 1998a[161] and 1998b[162] and Greenhill et al, 2003[163]). With a longer PK peak time and half-life (~8 hours) than methylphenidate (Ritalin®), twice-a-day administration of equal doses of d-l-amphetamine (Adderall®) resulted in an ascending PK profile and stable PD effects, while once-a-day administration resulted in a decreasing PK profile and dissipation of efficacy. These observations supported the notion that acute tolerance to amphetamine emerged. A coated-bead SR formulation for once-a-day administration (Adderall XR) was developed to mimic the serum concentration profile for twice-a-day administration of IR Adderall®, which produced an ascending serum concentration profile (McGough et al, 2003)[164]. A study using the laboratory school protocol was conducted to evaluate four doses of this formulation (Adderall XR®), which documented long duration of PD efficacy (12 hours) after a week of treatment with Adderall XR compared to placebo (Greenhill et al, 2003[165] and McCracken et al, 2003[166]).

Current state-of-the-art treatment of ADHD is with once-a-day formulations of stimulant medications, either methylphenidate (e.g., Concerta®) or amphetamine (e.g., Adderall XR®). Both of these formulations have an immediate-release (IR) or bolus dose that can be titrated to elicit an optimal and rapid clinical effect, and a sustained-release (SR) or programmed component for an increasing (ascending) delivery of the remaining dose across the day to counteract acute tolerance that is expected to emerge. In controlled trials, both formulations maintain a constant benefit for 8 to 10 hours, so the ascending drug delivery profile was effective in counteracting acute tolerance and provided an effective once-a-day administration. This improved adherence compared to immediate-release formulations by reducing stigma associated with taking medication in public and in inconvenience associated with taking medication two or three times a day.

National and international guidelines (e.g., Pliszka et al, 2007[167]; NICE, 2018[168]; Walkup et al, 2009[169]; Wolraich et al, 2019[170]) and Consensus Statements (e.g., Faraone et al, 2021[171]) agree that the first-line or primary treatment of ADHD should be with stimulant medications (e.g., methylphenidate or amphetamine). This is well-justified by extensive literature reviews (see Storebo et al, 2015[172] and Cortese et al, 2018[173]) on randomized controlled trials (RCTs), with relative benefit (e.g., significantly greater decrease in symptom severity for cases assigned to treatment with stimulant medication than to placebo or non-pharmacological treatment). ADHD is less often treated with non-stimulant medications (e.g., atomoxetine, guanfacine, clonidine, and mazindol), which have been shown to be effective and are approved for treatment of ADHD, but controlled studies reveal smaller effect sizes for non-stimulant than for stimulant medications (see Faraone et al, 2021)[174].

Swanson (2012)[175] summarized evidence from laboratory school studies regarding carry-over tolerance. A study conducted to evaluate four doses of Adderall XR® (see above) documented long duration of PD efficacy (12 hours) after a week of treatment with Adderall XR compared to placebo. In addition, this study suggested the possibility of carry-over tolerance during a week of treatment that was overcome after morning administration of Adderall XR: assessment of behavioral symptoms and performance on math tests before the administration of the drug of the $7^{th}$ day was worse for the weeks of Adderall XR than for placebo, with an effect size of −0.4, and then within an hour later administration of Adderall XR overcame carry-over effects and established efficacy with an effect size >1.0 (Greenhill et al, 2003[176] and McCracken et al, 2003[177]). A study conducted to evaluate Metadate CD® documented similar carry-over effects for methylphenidate (see Swanson et al, 2004[178] and Wigal et al, 2003[179]).

The two recent reviews identified many adequately-controlled trials of short-term (≤3 or ≤6 months) treatment with stimulant medication, but two adequately-controlled trials of long-term (≥1 year) treatment, the Multimodal Treatment Study of ADHD or MTA for children (MTA Group, 1999a)[180] and Comparison of Methylphenidate and Psychotherapy ADHD Study or COMPAS for adults (Philipsen et al, 2015)[181]. For the many short-term trials, the effect size (standardized mean difference in symptom severity for the assigned groups at the end of the RCT) was 0.8 for teacher ratings of children and 0.5 for observer ratings of adults, and for the two unique studies of long-term treatment, the effect size was significant but lower for children (0.47 in the MTA, a 39% decrease) and for adults (0.21 in the COMPAS, a 45% decrease).

In both randomized clinical trials of controlled long-term treatment (the MTA and COMPAS), adherence and clinical response to treatment by-protocol were monitored in monthly clinical visits, and daily dose of stimulant medication was adjusted if necessary. In the MTA, adherence was high but not perfect (76% of the cases were treated "as intended") and in the treated cases the average daily dose was increased from 20 to 30 mg/day by end of the RCT), and in the COMPAS adherence was lower (35% continued medication use to the end of the RCT) but in the treated cases the average dose was increased (from X to Y by the end of the RCT). Secondary analyses of the MTA suggested effect size at end of the RCT was mediated by adherence to assigned treatment (MTA Group, 1999b)[182].

Since ADHD is considered to be a chronic condition in a majority of childhood-onset cases (Faraone et al, 2021)[183], and in many follow-up studies (see Hechtman et al, 2016)[184] ADHD diagnosis has been associated with a variety of adverse functional outcomes (e.g., school failure, delinquency, substance use, etc.), general recommendation in treatment guidelines and consensus statements is for treatment to continue for as long as ADHD symptoms continue. However, even with high adherence and regular dose increases in clinical practice, long-term benefit of long-term medication use is difficult to detect, and eventually discontinuation of well-managed treatment is common. Since increases in dose provide a temporary solution, alternative strategies are needed. Based on the notion that tolerance undermines efficacy, innovative approaches based on plausible underlying neural mechanisms are proposed.

New Analyses of Long-Term Treatment as-Usual in the MTA Follow-Up

Adherence and persistence of use of stimulant medication suffers from substantial variation in the definitions adopted and methods applied to measure these complex concepts (see Gajria et al, 2014[185] and Ahmed and Aslani, 2013[186]). Based on the emerging area of pharmionics (see Vrijens et al, 2012[187]), new analyses were conducted on the long-term use of stimulant medication and outcome in the MTA.

Evidence of relative benefit of short-term medication use is extensive, but it is very sparse for long-term medication use (defined as ≥1 year). For example, Storebo et al (2015)[188] screened 9271 publications for children and adolescents treated with methylphenidate and 185 controlled trials qualified for the review, but the Multimodal Treatment Study of ADHD (MTA, 1999[189]) met the pre-set criterion for long-term treatment (>3 months). Also, Cortese et al (2018)[190] screened 9948 publications of children, adolescent, and adults treated with methylphenidate or amphetamine and 133 controlled trials qualified for the review, but the pre-set criterion for long-term treatment (52 months) was met by one study of adults, the Combined Methylphenidate and Psychotherapy in adults with ADHD Study (COMPAS; Philipsen et al, 2015[191]), and not by any study of children (the MTA was excluded based on the lack of a placebo or no-treatment control).

In addition to the meta-analyses of controlled studies of short-term treatment, Storebo et al (2015)[192] and Cortese et al (2018)[193] report the dearth of studies of long-term treatment. These reviews identified two adequately controlled studies. Storebo et al (2015)[194] included the Multimodal Treatment Study of ADHD (MTA), which was initiated in 1994 as a 14-month randomized clinical trial (RCT) and provided valid evidence that diagnosed cases benefit from a year of well-managed treatment by-protocol with stimulant medications compared to alternative treatments (see MTA Group, 1999)[195], and Cortese et al (2018)[196] included the Comparison of Methylphenidate and Psychotherapy (COMPAS), which was initiated in 2012 as a 12-month RCT and provided evidence of benefit from a year of treatment with methylphenidate with or without psychotherapy relative to placebo (Philipsen et al, 2015)[197].

For studies of short-term medication use in children, both reviews reported a large average effect size (~0.8) favoring treatment with stimulant medication, and for adults the review by Cortese et al (2018)[198] reported a moderate average effect size (~0.5), providing clear evidence of efficacy. For long-term treatment in the MTA, Storebo et al (2015)[199] reported an effect size of 0.47 vs 0.78 for teacher ratings (a 39% reduction compared to short-term treatment), and for long-term treatment in the COMPAS Cortese et al (2018)[200] reported an effect size of 0.27 vs 0.55 for observer ratings (a 45% reduction compared to short-term treatment).

However, both the MTA and COMPAS were continued as observational follow-up studies to evaluate maintenance of benefit after transition to treatment as-usual in community settings. In both studies, the initial relative benefit of stimulant medication dissipated over 1.5 to 2 years as cases in the assigned groups of the RCT had different patterns of starting and stopping medication. This is not unique to controlled trials of long-term treatment. Also, modern systematic reviews of prospective and retrospective studies of adherence and persistence of medication use (see Garjia et al, 2014[201] and Ahmed and Aslani, 2013[202]) indicate that, in general during treatment as-usual, the average treatment duration of treatment is <175 days and discontinuation occurs in most cases within a year.

Both the MTA (MTA Group, 2004)[203] and COMPAS (Lam et al, 2019)[204] continued as observational follow-up studies, and efficacy continued to dissipate. Intent-to-treat analysis of the residual effect of assigned treatment indicated most of the initial absolute benefit (the non-specific decrease in symptom severity from baseline) was maintained in all groups, but for the MTA across a 10 month follow-up the effect size for relative benefit decreased by 50% (from 0.6 to 0.3) and the for the COMPAS across an 18 months follow-up by 36% (from 0.27 to 0.17). Additional reports of extended outcome for the COMPAS have not been published, but several additional reports have been published describing medication use and outcome in the MTA follow-up through 3 years after baseline when cases were still in childhood (Jensen et al, 2007[205]; Swanson et al, 2007a[206] and 2007b[207]; Molina et al, 2007[208]), through 8 years after baseline when cases were in adolescence (Molina et al, 2009[209] and 2013[210]), and through 16 years after baseline when cases were in early adulthood (Swanson et al, 2017[211]). In the extended follow-up of the MTA, residual benefit of assigned treatment with medication dissipated completely by late childhood, and multiple analyses did not detect significant effects of medication use, evaluated either as current-observed or previous-assigned treatment, or cumulative or time-varying treatment from late childhood to early adulthood. The observed dissipation of efficacy during the RCT phase of the MTA was mediated by adherence to assigned treatment with medication, which was "as intended" for 76% of the cases based on attendance at monthly clinic visits where progress was monitored and adjustments to medication were prescribed (MTA, 1999b[212]). Mediation by adherence was not evaluated for the COMPAS, but by the end of the RCT 35% of the cases were being treated with stimulant medication. However, recent analyses of the MTA (Swanson, 2022[213]) indicate that even though the percentage of cases treated with medication decreased (from ~75% in childhood to 7% in adulthood) during treatment as-usual in the observational follow-up, during the DSM-IV era (from 1994 to 2013) annual adherence was high (>80% of days treated) from initiation to cessation of medication use and daily dose was increased regularly (from ~30 mg/day to ~60 mg/day across a decade of uninterrupted adequate treatment). This suggests that in modern clinical practice, a few cases received exemplary treatment with appropriate monitoring and adjustment of medication and continued treatment from childhood to adulthood, but even when this occurred, relative benefit dissipated and discontinuation of medication did not result in deterioration manifested by an increase in symptom severity, suggesting tolerance may have been present to undermine efficacy.

The multi-site MTA was initiated in the mid-1990s with in 3 waves across the 6 sites. Baseline assessments were conducted from 1994 to 1997, a 14-month randomized clinical trial phase conducted from 1995 to 1998, and the observational follow-up was conducted from 1998 to 2013. During the follow-up, the second generation SR formulations were developed, approved, and became available for clinical use. About 75% of the sample of 579 ADHD cases sought and obtained stimulant medication during the extended follow-up, when the SR formulations were prescribed for the treatment of almost all ADHD cases. The general trend of longitudinal use in individuals in the MTA cohort was for discontinuation of stimulant medication, with the percentage decreasing from 75% to <10% over a decade. However, for those continuing uninterrupted treatment, the average daily dose was increased (e.g., from ~30 mg/day to ~56 mg/day over the decade). Despite the switch to SR formulations (intended to deliver increasing dose across the day) and regular increased in daily dose over years, relative benefit (compared to cases never treated with stimulant medication or to those that discontinued treatment) was not detected (Swanson et al, 2017[214]). The emergence of extended tolerance across years of uninterrupted medication use during treatment as-usual in the MTA follow-up indicated the emergence of long-term tolerance (defined by dissipation of relative benefit despite upward adjustments in dose) for up to a decade compared to discontinuation or no medication use (Swanson et al, 2017[215].

Reviews of long-term treatment have reported similar findings. Shaw et al (2012[216]) and Arnold et al (2015)[217] reviewed uncontrolled pre-post studies and studies of non-randomized groups of ADHD cases treated with medication alone, psychosocial treatment alone, or the combination, and although not emphasized in the publications, close inspection indicted large non-specific benefit for all modalities of long-term treatment, with relative benefit greater for non-pharmacological than for pharmacological treatment alone, and best for the combination.

In reviews of studies of adherence and persistence of use of stimulant medications to treat ADHD, almost all cases initiating treatment in childhood discontinue treatment in late childhood (Gajria et al, 2014)[218]. In the MTA follow-up, almost all cases initiating effective treatment in childhood discontinuing the use of stimulant medication during late childhood or early adolescence (Molina et al, 2009)[219], and long-term benefit is difficult to detect (see Molina and Swanson, 2020)[220]. One explanation for discontinuation is that tolerance emerges and undermines efficacy when intensity of treatment (dose of stimulant medication) remains constant over time. This may be an unappreciated basis for some features of modern clinical practice. For example, Swanson et al (1999)[221] proposed that acute tolerance occurs rapidly after each administration of immediate-release stimulant medications (methylphenidate and amphetamine), and controlled-release formulations were developed to deliver ascending serum concentrations across to counteract tolerance and maintain full efficacy, and the MTA Group (MTA, 1999)[222] recognized dose-titration was essential since individuals varied in optimal daily dose, and after titration tolerance may emerge in some cases over the first few months of treatment, but proposed a medication algorithm to monitor clinical response based on monthly clinic visits and suggested a small increases in daily dose would be sufficient to maintain full efficacy.

The current consensus is that when these exemplary practices are implemented, long-term tolerance will not emerge, and full efficacy of well-managed treatment with stimulant medication would be maintained (Coghill, 2021)[223]. However, prospective follow-up studies indicate that discontinuation of medication occurs in most cases over the course of a few years of treatment. For example, Brinkman et al (2018)[224] evaluated self-report of reasons for stopping medication use in the MTA follow-up. When asked why they stop treatment with stimulant medication, the factor most often endorsed by cases was Lack of Perceived Need (e.g., 51.9% indicated "I felt I could manage without it", 44.8% indicated "I was tired of taking it", and 25.4% indicated "It was not helping me"). One explanation for this is that during extended treatment, even when dose is increased regularly, long-term tolerance emerges and undermines efficacy. Another factor endorsed by cases was Side Effects (27.9% indicated "it made me feel bad physically" and 21.9% indicated "It made me feel 'drugged'").

Based on pharmacokinetic (PK) and pharmacodynamic (PD) studies conducted in a laboratory school setting, Swanson et al (1999)[225] proposed that short-term or acute tolerance emerges after each dose of stimulant medication (e.g., within minutes or hours) and that an ascending drug delivery for 8 hours after a morning bolus dose could counteract this and prevent dissipation of efficacy across the day. This general strategy (of increasing dose by ascending drug delivery across the day to counteract acute tolerance and maintain full efficacy) was used to develop several effective once-a-day formulations of methylphenidate (i.e., Concerta® and Metadate CD®) and amphetamine (i.e., Adderall XR®), which essentially replaced the immediate-release formulations previously used in clinical practice for more than 50 years. Based on placebo-controlled, dose-response, randomized titration trials and prospective observational follow-up studies of school-aged children (the Multimodal Treatment Study of ADHD or MTA) and preschool children (the Preschool ADHD Treatment Study or PATS), multisite groups developed algorithms to initiate and monitor treatment with immediate-release formulations of stimulant medication (for the MTA, see Greenhill et al, 2001[226] and Vitiello et al, 2001[227], and for the PATS, see Greenhill et al, 2006)[228]. These algorithms influenced treatment guidelines (see Plitszka et al, 2007[229]) and clinical practice (e.g., see Atzori et al, 2009[230]) with once-a-day controlled-release formulations of stimulant medications that essentially replaced treatment with multiple daily doses of immediate-release formulations (e.g., see Coghill and Seth, 2015)[231]. However, these advances have not improved outcome associated with treatment as-usual in modern clinical practices.

In a recent study of controlled discontinuation after long-term (>3 year) use of stimulant medication, significant deterioration was not detected in adolescents (see Matthijssen et al, 2019)[232], and in an extended prospective observational follow-up study (the MTA), relative benefit was not significant in the few cases with continuation of treatment from childhood into adolescence or adulthood (~7% of the cohort) compared to cases that stop or never started treatment with stimulant medication (see Swanson et al, 2017[233]).

Biederman et al (2010)[234] and Buitelaar et al (2012)[235] conducted controlled trials for use of controlled-release formulations of stimulant medication in adults. Based on controlled placebo-substitution studies and prospective follow-up studies when treatment was closely monitored and optimized, significant deterioration was not detected when medication was discontinued. An alternative explanation is that during extended treatment, tolerance (defined as a reduced efficacy over time in response to a constant dose of medication or the need to increase dose to maintain efficacy) may emerge and undermine long-term benefit. The consensus of clinicians is that chronic or long-term tolerance in clinical practice is not a serious issue, based on experience of maintenance of extended long-term treatment in some cases with limited need to increase dose. In exemplary clinical practice, the effective clinical dose varies widely (e.g., 6-fold) across cases, and treatment is initiated by dose-titration to elicit an adequate (or optimal) response based in reduction of symptoms, and when clinical response is monitored on a regular basis (e.g., monthly or quarterly), in some cases efficacy may dissipate in the initial stage of treatment, but this is assumed to be self-limiting or associated with increasing body mass, and a stable effective daily dose will stabilize at a level below the approved maximum clinical dose. Prospective trials indicate even exemplary clinical treatment has not been sufficient to maintain most cases in treatment for more than a few years, either when initiated in childhood or in adulthood. Naturalistic discontinuation occurs in most cases, so long-term adherence and persistence of medication use are poor.

Here we propose a model of long-term tolerance that emerges during the clinical use of stimulant medication to treat ADHD in children, adolescents, and adults, and we propose undermines efficacy and contributes to poor adherence and persistence. Based on basic research on neural mechanism underlying effects of stimulant medications on animals and humans, the development of once-a-day formulations of methylphenidate and amphetamine were based on the concept that acute tolerance undermined the duration of action of immediate-release doses of these drugs, which led to development of effective sustained-release formulations based on pharmacokinetic (PK)/pharmacodynamic (PD) principles to overcome tolerance by provide increasing delivery of stimulant medication across the day. In addition to dose increases, PK/PD principles suggest other strategies to overcome tolerance. For example, an adequate dose-delay will allow for dissipation of acute tolerance, preventing carry-over tolerance and emergence of chronic or long-term tolerance.

Further Discussion

Previously, the laboratory school approach (see Swanson et al, 2002)[236] was described that (a) provided PK/PD assessments to develop 2$^{nd}$ generation CR formulations (based on surrogate measures of response in controlled settings), (b) detected a possible design flaw (based on the observation that acute tolerance did not dissipate overnight and carry-over tolerance was present before administration of current CR formulations the next morning, which was rapidly overcome by the effect of the bolus component), (c) generated an innovative extension of PK/PD analysis (based on predicted carry-over tolerance that would slowly accumulate and undermine efficacy), (d) estimated the time course of onset and duration of alternative medications for the treatment of ADHD (e.g., atomoxetine, modafinil, mazindol, and other non-stimulant medications), and (c) evaluated behavior and performance of adults in simulated workplace settings (as well as children in classroom and playground school settings).

An alternative biochemical theory of ADHD and neuropharmacological response to stimulant medication had been developed more than 20 years ago based on animal studies by Grace (2001)[237], but was not elaborated to apply to humans and to long-term exposure to stimulant drugs, and thus was not generally accepted. Grace (2001)[238] proposed (a) two classes of DA receptors in the brain (presynaptic receptors activated by low tonic levels of DA and postsynaptic receptors activated by high phasic levels of DA), (b) bursts of phasic DA entrained to environmental stimuli (which elicit approach and exploratory behavior and suggest ADHD symptoms may associated with a DA excess rather than deficit), (c) an initial agonist effect of stimulant medication (associated with blockade of the transporter that decreases DA reuptake, increases level of phasic DA released into the synapse, allows DA to escape the synapse that increases level of presynaptic tonic DA), (d) a delayed compensatory antagonist effect mediated by the increase in tonic DA level that reduces release of phasic DA (resulting in a net antagonist effect within an hour that reduces the abnormally high level of phasic DA and normalizes behavior), and (c) neural adaptations to account for acute tolerance to single doses of stimulant medication in animals (which in the previous application was extended for multiple doses of stimulant medication administered orally to humans to address long-term tolerance during clinical treatment of ADHD).

In the historical literature, different condition were identified in which tolerance to stimulant medication was and was not expected to occur based on (a) clinical experience with IR formulations suggesting that tolerance did not occur (summarized in a classic article by Safer and Allen, 1989[239] entitled "Absence of Tolerance to the Behavioral Effects of Methylphenidate"), (b) sustained-release delivery of methylphenidate by outdated wax matrix technology summarized by Greenhill and Osman (1991)[240], who suggested bolus delivery may avoid tolerance (but continuous delivery would not), (c) a massive review of human and animal studies by Solanto (1998)[241], who concluded in typical clinical practice there was an "absence of tolerance to stimulant drug effects" (and no difference between acute and chronic use of stimulant medication), (d) brain imaging studies of methylphenidate and cocaine summarized by Volkow et al (1995)[242], who emphasized differences associated with route of administration and rapid changes in synaptic DA (with lack of euphoria associated with relatively slow onset after oral administration of methylphenidate and tolerance associated with slow clearance from the site of action in the brain), and (c) animal studies of repeated administration of methylphenidate, which were reviewed by Grace (1995)[243] who described a cascade of fast homeostatic processes that maintain baseline levels of DA and slow destabilizing neural responses that prevent this, and by Yano and Steiner (2007)[244], who described upregulation of striatal genes and neuroplasticity after repeated exposure to methylphenidate.

Positron Emission Tomography (PET) imaging has been applied to document neural adaptations to long-term exposure to stimulant medications associated with DA transporter (DAT) density, which revealed (a) prolonged DAT occupancy after acute doses of methylphenidate, (b) low DAT density in untreated adults with ADHD (Volkow et al, 2007)[245] (c) increased DAT density after long-term treatment (Wang et al, 2013)[246], (d) rebound effects in the nucleus accumbens after cessation of extended exposure in rhesus monkeys (Gill et al, 2012)[247], and (c) decreased bone strength in rodents (Thanos et al, 2010)[248].

Several observations are relevant for addressing unmet needs for formulations of medication to treat chronic ADHD: (a) approved dual-component formulations of stimulant medications are clinically effective during short-term treatment (but efficacy dissipates during long-term treatment), (b) symptoms and impairment persist in a majority of cases and are associated with risk for adverse long-term outcomes (but treatment is discontinued in most cases and the primary reasons given for stopping treatment are "medication stopped working/not needed" or "medication made me feel bad"), (c) popular formulations of stimulant medications have an IR component that results in rapid onset of efficacy (but has a short duration that requires a CR component), (d) the CR formulations are programmed for ascending delivery of stimulant medication for 8-10 hours followed by 12-14 hour medication-free period (but this is not sufficient for acute tolerance to dissipate completely each day and thus results in carry-over tolerance), and (c) in clinical practice after week to months of uninterrupted use of CR formulations efficacy wanes and upward adjustments to daily dose of stimulant medication are needed (but eventually the maximum approved dose is reached and treatment is usually discontinued).

Innovative proposals are developed for new formulations that maintain the bolus IR component of stimulant medication (to block the DA transporter and elicit the usual rapid clinical benefit) but replace the ascending component with a non-stimulant medication (that would target non-DA systems to maintain efficacy and allow additional time for acute tolerance to the bolus of stimulant medication to dissipate). To provide an improvement for medications for extended treatment of chronic ADHD, different combinations of stimulant and non-stimulant medications are proposed for new and innovative dual-component CR formulations. Each proposed combination includes an initial bolus IR component of stimulant medication to target striatal DA transporters and have rapid onset of efficacy associated with known PK/PD factors ($T_{max}$ and $T_{1/2}$) plus a CR component of promising non-stimulant medications (see Pozzi et al, 2020[249], including some approved for the treatment of ADHD, such as atomoxetine (which targets NE transporters in the prefrontal cortex), mazindol (which targets the orexin system), clonidine and guanfacine (which target the NE system), and some that are not approved but have been used off-label for the treatment of ADHD, such as modafinil (which targets NE transporters in locus coeruleus), buspirone (which targets the serotonin system), bupropion (which targets the NE system), and other non-stimulant medications that do not target DA).

The laboratory school protocol was applied successfully to conduct proof-of-principle studies 20 years ago for the development of $2^{nd}$ generations CR formulations of stimulant medications (see Swanson et al, 2002[250] for a summary). This proof-of-principle approach could be applied to evaluate whether carry-over tolerance emerges during extended treatment with the proposed new dual-component formulations (described above), before embarking on an extended long-term follow-up in the natural environment.

In addition, more than 20 years ago the MTA medication algorithm was implemented (consisting of monthly visits and monitoring of maintenance of effectiveness), which detected dissipation of effectiveness that emerged over the first year of observational follow-up. The loss of effectiveness was partially counteracted by regular adjustments to daily dose, which on average was increased by about 30% over the year and maintained a significant relative benefit at the end of the 14-month randomized controlled trial (but still was reduced by about 40% compared to the average for short-term controlled trials). This approach to detect long-term tolerance could be applied after the laboratory school phase was implemented to test the prediction that carry-over tolerance would not emerge during the initiation of the new innovative formulations of medication. In addition, the qualitative assessment of reasons for naturalistic discontinuation (which occurs in a majority of cases by 3 years after initiation of treatment with stimulant medication) could be implemented to provide additional assessment of attitudes and opinions regarding long-term use of the proposed new and innovative formulations of medication, to test the prediction that the primary reasons for stopping treatment ("medication stopped working/was not needed" and "medication made me feel bad") would be less likely than previously reported in follow-up studies. Finally, the methods developed to recent controlled discontinuation studies (based on the placebo substitution method) could be implemented in cases that do not spontaneously stop treatment to test the prediction that relative deterioration would be detected in a majority of cases when the new formulations were discontinued, which in a provide additional support that long-term tolerance does not emerge.

The approach and purpose of the proposed new formulations of medication described herein according to some implementations differ from other approaches and purposes for replacement of stimulant medications with non-stimulant medications. Other approaches have focused on avoiding stimulant-related side effects (e.g., decreased appetite, insomnia, growth suppression, etc.) or providing an alternative treatment for cases that do not respond favorably when stimulant medication is initiated. The innovative approach described here is based on replacement or partial replacement of the CR component of widely used stimulant medications with a non-stimulant component or other component that avoids tolerance during extended treatment to maintain a favorable clinical response. This is doubly innovative since the current consensus is that tolerance to stimulant medication does not occur (or is minimal or rare) and a common assumption is that long-term effectiveness dissipates primarily because exemplary long-term treatment is usually not provided in community settings (even though sparse data from the MTA follow-up indicates dissipation occurs even when extended exemplary long-term treatment is provided). It is likely there are multiple factors why long-term tolerance has not been recognized (e.g., short-term controlled trials document treatment is very effective, long-term controlled trials are very rare, and the emergence of long-term tolerance is gradual). Also, pre-post benefits are maintained (but this does not provide evidence of efficacy), which may mask the dissipation of relative benefits compared to alternatives (the appropriate source of scientific evidence). The innovative proposal presented here is based on the insight that long-term tolerance to stimulant medica-
tion has a plausible biological basis and is associated with
complex neural homeostatic adaptations that emerge gradu-
ally and eventually accumulate to undermine effectiveness.

Formulations and Methods

In view of the foregoing, it is proposed that dissipation of
relative benefit during long-term treatment is due to long-
term tolerance to stimulant medications. To improve adher-
ence (how often) and persistence (how long) of medication
use and meet the critical clinical need, it is advantageous to
develop medications that are not undermined by long-term
tolerance.

Based on new interpretations of pharmacokinetic (PK)
and pharmacodynamic (PD) properties of stimulant medi-
cation (see FIGS. 1A and 1B), re-evaluation of assumptions
about the rate of dissipation of acute tolerance (see FIG. 2),
re-consideration of an unaccepted hypothesis that oral
stimulant medication acts as a net dopamine antagonist
rather than agonist (see FIGS. 3A, 3B, and 3C), and exten-
sion of the implications for multiple oral administrations
across the day and across days, weeks, months, and years
(see FIGS. 4A and 4B), conclusions are drawn regarding the
dynamic properties of accumulated tolerance to stimulant
medications (see FIGS. 5A, 5B, and 5C).

Based on these innovative ideas and novel insights, in
accordance with certain implementations, an alternative
formulation of medication for the treatment of ADHD is
proposed, based on two principles: (a) retaining the initial
immediate-release component of controlled-release formu-
lations (i.e., a bolus oral dose of stimulant medication
designed to elicit an appropriately timed initial antagonist
effect mediated by inhibiting phasic dopamine release to
produce a clinical benefit without eliciting a euphoric
response by a competing agonist effect), and (b) replacing
the subsequent sustained-release component (i.e., an ascend-
ing delivery of stimulant medication to counteract acute
tolerance) with the new and innovative controlled-release
component designed to prevent carry-over effects on back-
ground tonic dopamine that ordinarily would operate to
provide homeostatic regulation that would be manifested as
long-term tolerance.

Tachyphylaxis is an acute and sudden decrease in
response to a drug following its administration. In other
words, it is rapid and short-term onset of drug tolerance that
can occur following an initial dose of medication and/or a
series of small doses of medication. Continuing to admin-
ister a drug that results in tachyphylaxis results in an
accumulation of tolerance over time. This accumulation of
tolerance results in the drug being less effective over time at
a particular dose.

As discussed hereinabove, one current method of treating
ADHD involves administering an extended-release formu-
lation of one or more stimulant medications in which the
drug is timed for immediate release of one dose amount
followed by increasingly larger dosage amounts through the
day to combat tachyphylaxis. Unfortunately and surpris-
ingly, it appears that such a dosage regimen does not avoid
the accumulation of tolerance to an administered stimulant
medication because the time between the delivery of the last
dose in the extended-release formulation and the time that
the next dose is to be taken is insufficient to allow tolerance
to fully dissipate. Accordingly, some tolerance still exists
when the patient takes the medication again the next morn-
ing according to the usual once-a-day dosage schedule, and
thus there is carry-over and tolerance accmulates. This results in the efficacy of the medication being gradually
reduced with each passing day.

These negative effects resulting from tachyphylaxis are
not seen with most non-stimulant drugs and/or other drugs
that may not induce tachyphylaxis that have some effective-
ness against ADHD and/or symptoms of ADHD, sometimes
referred to herein as "alternative ADHD drugs". It is to be
understood that drugs having effectiveness against ADHD
and/or symptoms of ADHD in the context of this application
are not limited to drugs that have been approved by a
regulatory body for treatment of ADHD or symptoms
thereof, and it also includes those drugs that have been
shown (e.g. in scientific or medical literature) to have
effectiveness or that are believed by at least some in the
medical or psychiatric arts to have effectiveness against
ADHD and/or symptoms thereof. Although certain alterna-
tive ADHD drugs have effectiveness against ADHD and/or
symptoms of ADHD, they do not act in the same manner as
the traditional stimulant drugs that target the neurotransmit-
ter dopamine that is considered to be the basis for inducing
tachyphylaxis and therefore have different mechanisms of
actions that result in effects in the patient. For example, it is
known that traditional stimulant drugs that induce tachy-
phylaxis used against ADHD are effective for initiating an
effect such as initially directing attention whereas alternative
ADHD drugs are oftentimes less effective than traditional
stimulants at directing attention but are effective at main-
taining effectiveness or efficacy, such as by maintaining
attention, over the course of the day.

Accordingly, in order to obtain the benefit of good ini-
tiation of effect such as an initial direction of attention by a
stimulant medication without the negative effect of tachy-
phylaxis and eventually accumulation of tolerance that leads
to a loss of effectiveness over time, it is proposed to
administer to a patient a first, immediate-release dose of a
stimulant drug having effectiveness against ADHD but
which causes tachyphylaxis, followed by administering or
delivering an extended-release formulation of an alternative
ADHD drug that does not induce or contribute to tachyphy-
laxis when the first stimulant drug wears off or reaches its
pharmacodynamic half-life, generally within about 1-4
hours of the first drug being delivered or administered. In
certain implementations, the stimulant drug has effective-
ness immediately (e.g., within about 1-30 minutes) upon
delivery. By the time the next time the stimulant portion or
component is administered (assuming once daily adminis-
tration of the regimen, as is standard for extended release
ADHD medications), it has been approximately 24 hours
since the last dose of stimulant, such that tachyphylaxis will
have dissipated completely and there would be no accumu-
lation of tolerance, thereby allowing the patient to obtain the
full benefit of the stimulant medication each day while still
effectively treating their ADHD symptoms for a similar time
frame as presently-known ADHD extended-release stimu-
lant drugs.

Stimulant drugs that have effectiveness against ADHD
and/or ADHD symptoms which induce or contribute to
tachyphylaxis include, but are not limited to dextroamphet-
amine, amphetamine, dexmethylphenidate, methylpheni-
date, lisdexamfetamine, and combinations thereof.

Alternative ADHD drugs, that is drugs that have some
effectiveness against ADHD and/or symptoms of ADHD and
which are non-stimulant drugs, drugs that are not dopamine
agonists, and/or stimulants that may not induce tachyphy-
laxis, include, but are not limited to mazindol, modafinil,
atomoxetine, clonidine, guanfacine, viloxazine, bupropion,
desipramine, imipramine, nortriptyline, and combinations thereof. Although certain alternative ADHD drugs may be considered to be "stimulants" (e.g., mazindol), they may not contribute to tachyphylaxis or accumulation of tolerance.

As used in the discussion herein, "administered" is used to describe the act of a patient taking a medication, such as by swallowing a pill, whereas "delivered" is used to describe when the drug is made available to the body of the patient. As an example, for an extended release tablet with an initial twelve-hour duration of action having an immediate-release component, the medication is administered when the patient swallows the tablet, the first, immediate-release component is both administered and delivered when the patient swallows the tablet, but the delayed-release components are administered at the time of swallowing, but not delivered until the later time that they become available to the body which may occur hours after administration.

In accordance with some implementations, a dose of a tachyphylaxis-inducing stimulant medication is administered and delivered to a patient. The amount and formulation of drug delivered may be as is known and used in the art for immediate-release formulations of the drug. The dose is preferably given in the morning or otherwise at the start of the patient's day or extended period of desired wakefulness. In the minutes and hours following delivery of the dose of the tachyphylaxis-inducing stimulant medication, the body begins to clear the drug from the bloodstream and the brain. It has been found that the clearance from the bloodstream (contributing to the pharmacokinetic half-life of the drug) is faster than the clearance of the drug from the brain and thus its effect on the brain (contributing to the pharmacodynamic half-life of the drug).

After a period of about 1 to 4 hours, including about 1.5 hours, about 2 hours, about 2.5 hours, about 3 hours and about 3.5 hours, the delivery of a first dose of an alternative ADHD drug is initiated. In some implementations, the delivery of a first dose of an alternative ADHD drug is initiated when the tachyphylaxis-inducing stimulant drug approaches or reaches its pharmacodynamic half-life, including about 30 minutes to 1.5 hours before or after the pharmacodynamic half-life, including about 0.5 hours, about 1 hour, about 1.5 hours, and ranges encompassed by any two of the foregoing values.

The alternative ADHD drug may be provided in an amount and formulation as is known and used in the art for controlled-, delayed- and/or extended-release formulations of the drug. In certain implementations, the drug is formulated so that the first dose of the alternative ADHD drug is delivered (or made bioavailable) at a desired time following the delivery of the tachyphylaxis-inducing stimulant, and/or the administration of a single unit dosage form containing both the tachyphylaxis-inducing stimulant and an alternative ADHD drug. In some implementations, the alternative ADHD drug is formulated to be delivered over a total period of about 5 to 13 hours (including about 6 to 12 hours, about 7 to 10 hours, about 8 to 10 hours, about 6 to 10 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, and other ranges encompassed by any two of the foregoing values). In some implementations, the alternative ADHD drug is formulated to be delivered beginning at a time about 1 to 6 hours (including about 2 to 4 hours, about 1 hour, 1.5 hours, about 2 hours, about 2.5 hours, about 3 hours, about 3.5 hours, about 4 hours, about 4.5 hours, about 5 hours, about 5.5 hours, about 6 hours, and other ranges encompassed by any two of the foregoing values) following delivery of the tachyphylaxis-inducing stimulant or administration of the extended-release alternative ADHD drug, either alone or together with the tachyphylaxis-inducing stimulant as part of a unit dosage form for once daily administration.

In certain implementations, the combinations of tachyphylaxis-inducing stimulant and alternative ADHD drugs are administered to a patient in need thereof in a single-unit dosage form. This single unit may take any suitable form, including an oral form such as a tablet (including caplets), a capsule, or even an osmotic dosage form, including but not limited to those known in certain commercially available formulations of methylphenidate. In some implementations, a tablet, caplet, capsule or osmotic dosage form formulated for extended-release of an alternative ADHD drug is coated or otherwise covered in whole or in part with an immediate-release formulation of a tachyphylaxis-inducing stimulant. In some implementations, a capsule contains a plurality of pharmaceutical-containing beads of three or more types wherein a first type of bead comprises an immediate-release formulation of a tachyphylaxis-inducing stimulant, and the second and third types of bead (and potentially additional types of bead) comprise an alternative ADHD drug formulated for delayed release (i.e. to be delivered at a time later than when the capsule is administered to the patient), with the second and third (and possibly additional) types of bead each being formulated for release or delivery at a different time and being present in a sufficient quantity to allow for delivery of a desired or pharmaceutically effective dose over an extended period of time. The first type of bead is also present in a quantity sufficient to allow for delivery of a single desired or pharmaceutically effective dose of the tachyphylaxis-inducing stimulant.

In some implementations, a single unit dosage form is to be administered once per day, at least 20-24 hours following the administration of the prior dose. In some implementations, a single unit dosage form is formulated to deliver drugs and/or have efficacy over a total period of 6 to 12 hours, including about 6 to 10 hours, over a period of about 4 to 16 hours, including about 6 to 14 hours, about 6 to 12 hours, and about 6 to 10 hours.

In other implementations, a pack is provided containing multiple individual doses of drugs. A pack may include, for example, a single immediate-release dose of tachyphylaxis-inducing stimulant, and one or more doses of alternative ADHD drug. If there is only one dose of alternative ADHD drug, it is preferably formulated for extended release. If there are two or more doses of alternative ADHD drug, they may be formulated for extended release or immediate release as needed to obtain the desired length of time of action of the drug. In some implementations, a pack is in the form of a blister pack containing 1 to 30 days, including 1 to 7 days and 1 to 14 days, worth of medication and comes with instructions as to which individual doses to take and when to take them together with the pack or printed on the pack. In other implementations, a pack is in the form of multiple bottles wherein each bottle contains either the immediate-release tachyphylaxis-inducing stimulant or an immediate or extended-release formulation of alternative ADHD drug together with instructions (including labeling on bottles provided to the consumer) providing instructions on how and when to take the different dose forms of the drugs.

As used herein "drug" is a broad term used to describe a therapeutic agent or composition used for treatment of a condition or symptoms of such a condition, such as ADHD. A pharmaceutical composition includes one or more drugs, together with any pharmaceutically acceptable excipients, such as fillers, dispersants, binders, solvents, lubricants, emulsifying agents, suspending agents, preservatives, and the like.

Terminology

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily can include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others. "Comprising" is intended to also include the narrower terms "consisting of" and "consisting essentially of," the latter term meaning that the scope is limited to the recited elements or steps and any others that do not materially affect the basic and novel characteristics of what is already recited; the term 'having' should be interpreted as 'having at least;' the term 'includes' should be interpreted as 'includes but is not limited to;' the term 'example' is used to provide examples of instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in particular implementations of the invention. Likewise, a group of items linked with the conjunction "and" should not be read as requiring that each and every one of those items be present in the grouping, but rather should be read as 'and/or' unless expressly stated otherwise.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

CITED REFERENCES IN THE SPECIFICATION

1. [0003/0004] DSM (1980): Diagnostic and Statistical Manual (DSM), Edition III. American Psychiatric Association. 1980; Washington DC.

2. [0003/0004] Swanson (1978): Swanson J, Kinsbourne M, Roberts W, Zucker K. Time-response analysis of the effect of stimulant medication on the learning ability of children referred for hyperactivity. Pediatrics. 1978; 61:21-29.

3. [0003/0004] Abikoff et al (1985): Abikoff, H., Gittelman, R. The normalizing effects of methylphenidate on the classroom behavior of ADDH children. J Abnorm Child Psychol, 1985: 13, 33-44.

4. [0003/0004] Swanson et al (1983): Swanson J, Sandman C, Deutsch C, Baren M. Methylphenidate hydrochloride given with or before breakfast: I. Behavioral, cognitive, and electrophysiologic effects. Pediatrics. 1983; 72:49-55. (Presented in 1984 at AACAP meeting).

5. [0004/0005] Arnold et al (1997): Arnold L E. Abikoff H B, Cantwell D P, et al for the MTA Group NIMH collaborative multimodal treatment study of children with ADHD (MTA): Design, methodology, and protocol evolution. J Attention Disorders, 1997: 2:141-158.

6. [0004/0005] Greenhill et al (2001): Greenhill L, Swanson J, Vitiello B, et al. Impairment and deportment responses to different methylphenidate doses in children with ADHD: the MTA titration trial. J Am Acad Child Adolesc Psychiat. 2001; 40:180-187.

7. [0004/0005] Vietiello et al (2001): Vitiello B, Severe J, Greenhill L, Arnold L, Abikoff H, Bukstein O, Elliott G, Hechtman L, Jensen P, Hinshaw S, March J, Newcorn J, Swanson J, and Cantwell D. Methylphenidate dosage for children with ADHD over time under controlled conditions. J Am Acad Child Adolesc Psychiat. 2001; 40:188-196.

8. [0005/0006] DSM-IV (1994): Diagnostic and Statistical Manual (DSM), Edition IV. American Psychiatric Association. 1994; Washington DC.

9. [0005/0006] Swanson et al (1999): Swanson J, Gupta S, Guinta D, Flynn D, Agler D, Lerner M, Williams L, Shoulson I, Wigal, S. Acute tolerance to methylphenidate in the treatment of ADHD in children. Clin Pharmacol Ther. 1999; 66:295-305.

10. [0005/0006] Swanson et al (2003): Swanson J, Gupta S, Lam A, Shoulson I, Lerner M, Modi N, Lindemulder E, Wigal S. Development of a new once-a-day formulation of methylphenidate for the treatment of ADHD: Proof-of-concept and proof-of-product studies. Arc Gen Psy. 2003; 60: 204-211.

11. [0006/0007] Swanson et al (1998): Swanson J, Wigal S, Greenhill L, Browne R, Waslik B, Lerner M, Williams L, Flynn D, Agler D, Crowley K, Fineberg E, Regino R, Baren M, Cantwell D. Objective and subjective measures of the pharmacodynamic effects of Adderall in the treatment of children with ADHD in a controlled laboratory classroom setting. Psychopharmacology Bulletin. 1998; 34:55-60. (presented in 1997 at the NCDEU Mecting).

12. [0006/0007] McCracken et al (2003): McCracken J T, Biederman J, Greenhill L L, Swanson J M, McGough J J, Spencer T J et al. Analog classroom assessment of a once-daily mixed amphetamine formulation, SLI381 (Adderall XR), in children with ADHD._J Am Acad Child Adolesc Psychiatry. 2003; 42:673-683.

13. [0008/0009] Mattingly et al (2021): Mattingly G, Wilson J, Ugarte L, and Glaser P. Individualization of attention-deficit/hyperactivity disorder treatment: pharmacotherapy considerations by age and co-occurring conditions. CNS Spectrums, 2021: 26, 202-221.

14. [0009/0010] Swanson and Volkow (2008): Volkow N and Swanson J. Basic Neuropsychopharmacology. In M Rutter (Ed.), *Rutter's Child and Adolescent Psychiatry, 5th Edition*. Blackwell Publishing. 2008; 212-233.

15. [0009/0010] Swanson (1998): Swanson J, Wigal S, Greenhill L, Browne R, Waslik B, Lerner M, Williams L, Flynn D, Agler D, Crowley K, Fineberg E, Baren M, Cantwell D. Analog classroom assessment of Adderall in children with ADHD. J Am Acad Child Adolesc Psychiatry. 1998; 37:519-526.

16. [0009/0010]: Swanson et al (1999): Swanson J, Gupta S, Guinta D, Flynn D, Agler D, Lerner M, Williams L, Shoulson I, Wigal, S. Acute tolerance to methylphenidate in the treatment of ADHD in children. Clin Pharmacol Ther. 1999; 66:295-305.

17. [0009/0010] Greenhill et al (2003): Greenhill L, Swanson J, Steinhoff K, Fried J, Posner K, Lerner M, Wigal S, Clausen S, Zhang Y, Tulloch S. A pharmacokinetic/ pharma-codynamic study comparing a single morning dose of Adderall to twice-daily dosing in children with ADHD. J Am Acad Child Adolesc Psychiatry. 2003; 42:1234-1241.

18. [0009/0010] Swanson et al (2000): Swanson J, Greenhill L, Pelham W, Wilens T, Wolraich M, Abikoff H, Atkins M, August G, Biederman J, Bukstein O, Conners C K, Efron L, Ficbelkorn K, Fried J, Hoffman M, Lambrecht L, Lerner M, Leventhal B, McBurnett K et al. Initiating Concerta (OROS methyphenidate HC1) qd in children with ADHD. J Clinical Rescarch. 2000; 3:9-76.

19. [0009/0010] McCracken et al (2003): McCracken J, Biederman J, Greenhill L, Swanson J, McGough J, Spencer T, et al. Analog classroom assessment of a once-daily mixed amphetamine formulation, SLI381 (Adderall XR) in children with ADHD. J Am Acad Child Adolesc Psychiat. 2003; 42:673-683.

20. [0009/0010] Wigal et al (2003): Wigal S, Sanchez D, DeCory H, D'Imperio J, Swanson J. Selection of the optimal dose ratio for a controlled-delivery formulation of methylphenidate. The Journal of Applied Research. 2003; 3:46-63

21. [0034/0035] Swanson and Volkow (2002): Swanson J and Volkow N. Pharmacokinetic and pharmacodynamic properties of stimulants: implications for the design of new treatments for ADHD. Behav Brain Res 2002; 130: 73-78.

22. [0034/0035] Volkow et al (2007): Volkow N, Wang G, Newcorn J, Fowler J, Telang F, Solanto M, Logan J, Wong C, Ma Y, Swanson J, Schulz K, Pradhan K. Brain dopamine transporter levels in treatment and drug naïve adults with ADHD. NeuroImage. 2007; 34:1182-1190.

23. [0034/0035] Wang et al (2013): Wang G-J, Volkow N, Wigal T, Kollins S, Newcorn J, Telang F, Logan J, Jayne M, Wong C, Han H, Fowler J, Zhu W, Swanson J. Long-term stimulant treatment affects brain dopamine transporter level in patients with attention deficit hyperactive disorder. PLoS One. 2013. 8: e63023.

24. [0035/0036]: Swanson et al (2012): Swanson J. Short and Long-term Tolerance to Stimulant Medication. Presentation at AACAP. 2012; San Francisco CA 25. [0036/0037] Faraone et al (2021): Faraone S, Banaschewski T, Coghill D, Zheng Y, Biederman J, Bellgrove M, et al. The World Federation of ADHD international consensus statement: 208 evidence-based conclusions about the disorder. Neuroscience & Biobehavioral Reviews. 2021; 128: 789-818.

26. [0036/0039] UN (2020): United Nations, International Narcotics Control Board (INCB), Annual Report Psychotropic Substances. 2020; New York City NY.

27. [0036/0037] Storebo et al (2015): Storebo O, Ramstad E, Krough H, Nilausen T, Skoog M, Holmskov M, Rosendal S, Groth C, Magnusson F et al. Methylphenidate for children and 28. [0036/0037] Cortese et al (2018): Cortese S, Adamo N, del Glovane C, Mahr-Jensen C, Mayes A, Carucci S, Atkinson L Z, Tessari L, Banaschewski T, Coghill D, Hollis C, Simonhoff E, Zuddas A, Barbui C, Purgato M, Steinhausen H-C, Shokranch F, Xia J, and Cipriani A. Comparative efficacy and tolerability of medications for attention-deficit hyperactivity disorder in children, adolescents, and adults: a systematic review and network meta-analysis. Lancet Psychiatry, 2018. 5:727-738.

29. [0036/0037] Bhat and Hechtman et al (2016): Bhat V and Hechtman L. Considerations for selecting treatments for ADHD. Clinical Pharmacist. 2016. 8: 1-5.

30. [0036/0037] Molina and Swanson (2020): Molina B and Swanson J. Why Are Long-term Benefits of Stimulant Medication So Difficult to Detect? The ADHD Report, 2020. 28:1-7.

31. [0036/0037] Gajria et al (2014): Gajria K, Mei, L, Sikirica V, Greven P, Zhong Y, ADHD—a systematic literature review. Neuropsych. Disease and Treatment, 2014:10, 1543-1569.

32. [0036/0037] Ahmed and Aslani (2013): Ahmed R and Aslani P. An update on medication adherence and persistence in children. Expert Review Pharmacoeconomics Outcome Rescarch, 2013. 13: 791-815.

33. [0036/0037] Charach and Fernandez (2013): Charach A and Fernandez R. Enhancing ADHD Medication Adherence: Challenges and Opportunities. Curr Psychiatry Reports, 2013; 15:371-378.

34. [0037/0038] Cortese et al (2019): Cortese S. Debate: Are Stimulant Medications for Attention-Deficit/Hyperactivity Disorder Effective in the Long Term? Journal of the American Academy of Child and Adolescent Psychiatry. 2019; 58, 936-949.

35. [0037/0038] Coghill D (2019): Coghill D. Proponent: Are Stimulant Medications for Attention-Deficit/Hyperactivity Disorder Effective in the Long Term? Journal of the American Academy of Child and Adolescent Psychiatry. 2019; 58, 936-949.

36. [0037/0038] Swanson (2019): Swanson J. Opponent: Are Stimulant Medications for Attention-Deficit/Hyperactivity Disorder Effective Are Effective in the Long Term? Journal of the American Academy of Child and Adolescent Psychiatry. 2019; 58, 936-949.

37. [0038/0039] Molina and Swanson (2020): Molina B and Swanson J. Why Are Long-term Benefits of Stimulant Medication So Difficult to Detect? The ADHD Report, 2020. 28:1-7.

38. [0048/0049] DSM-5 (2013): Diagnostic and Statistical Manual (DSM), Edition IV. American Psychiatric Association. 2013; Washington DC.

39. [0048/0049] ICD-11 (2019: Internation Classification of Diseases (ICD), Version 11. World Health Organization. 2019; Geneva.

40. [0048/0049] Faraone et al (2021): Faraone S et al. The World Federation of ADHD international consensus statement. 208 evidence-based conclusions about the disorder. Neuroscience & Biobehavioral Reviews. 2021; 128: 789-818.

41. [0048/0049] ICD-9 (1979): Internation Classification of Diseases (ICD), Version 9. World Health Organization. 1979; Geneva.

42. [0048/0049] DSM-III (1980): Diagnostic and Statistical Manual (DSM), Edition III. American Psychiatric Association. 1980; Washington DC.

43. [0048/0049] Polanczyk et al (2014): Polanczyk G, Willcutt E, Salum G et al. ADHD prevalence estimates across three decades: an updated systematic review and meta-regression analysis. Int J Epidemiol. 2014:43:434-442.

44. [0049/0050] Bradley (1937): Bradley, C. The behavior of children receiving benzedrine. The American Journal of Psychiatry. 1937; 94, 577-585.

45. [0049/0050] Safer and Allen (1976): Safer D and Allen R. Hyperactive Children: Diagnosis and Management: 1976, University Park Press, Baltimore.

46. 10049/00501 NRC (1989): National Research Council, Research on Children and Adolescents with Mental, Behavioral, and Developmental Disorders: Mobilizing a National Initiative. 1989; Washington, DC: The National Academies Press.

47. 10049/005 wasson et al (1993): Swanson J, McBurnett K, Wigal T, Pfiffner L, Lerner M, Williams L, Christian D, Tamm L, Willcutt E, Crowley K, Clevenger W, Khouzam N, Woo C, Crinella F, Fisher, T. Effect of stimulant medication on children with attention deficit disorder: A "Review of Reviews". Exceptional Children. 1993; 60:154-162.

48. 10049/00501 NRC (1989): National Research Council, Research on Children and Adolescents with Mental, Behavioral, and Developmental Disorders: Mobilizing a National Initiative. 1989; Washington, DC: The National Academies Press.

49. [0049/0050] RFA (1992): Request for Application (RFA) MH-92-03 P101. Cooperative Agreement for a multi-site treatment study of ADHD, NIH Guide. 1992; 21:9, 1-25

50. [0049/0050] Time (1994): Wallis C. Behavior: Attention Deficit Disorder: Life in Overdrive. Time Magazine, 1994 July 18, Vol. 144 No. 3.

51. [0050/0051] RFA (1992): Request for Application (RFA) MH-92-03 P1O1. Cooperative Agreement for a multi-site treatment study of ADHD, NIH Guide. 1992; 21:9, 1-25.

52. [0050/0051] DSM-IV (1994): Diagnostic and Statistical Manual (DSM), Edition IV. American Psychiatric Association. 1994; Washington DC.

53. [0050/0051] Arnold et al (1997): Arnold L, Abikoff H, Cantwell D, Conners C, Elliott G, Greenhill L, et al. for the MTA Group. National Institute of Mental Health collaborative multimodal treatment study of children with ADHD (MTA): design, methodology, and protocol evolution. *Journal of Attention Disorders.* 1997, 2:141-50.

54. [0050/0051] Greenhill et al (2001): Greenhill L, Swanson J, Vitiello B, Davies M, Clevenger W, Wu M, Arnold L, Abikoff H, Bukstein, O, Conners C, Elliott G, Hechtman L, Hinshaw S, Hoza B, Jensen P, Kraemer H, March J, Newcorn J, Severe J, Wells K, Wigal T. Impairment and deportment responses to different methylphenidate doses in children with ADHD: the MTA titration trial. J Am Acad Child Adolesc Psychiatry. 2001, 40:180-187.

55. [0050/0051] MTA Group (1999a): MTA Cooperative Group. A 14-month randomized clinical trial of treatment strategies for attention deficit hyperactivity disorder. Arch Gen Psychiatry; 1999; 56:1073-108.

56. [0050/0051] Vitiello et al (2001): Vitiello B, Severe J, Greenhill L, Arnold L, Abikoff H, Bukstein O, Elliott G, Hechtman L, Jensen P, Hinshaw S, March J, Newcorn J, Swanson J, and Cantwell D for the MTA Group. Methylphenidate dosage for children with ADHD over time under controlled conditions: lessons from the MTA. J Am Acad Child Adolesc Psychiat. 2001: 40:188-196.

57. [0051/0052] MTA Group (2004a): MTA Cooperative Group. National Institute of Mental Health Multimodal Treatment Study of ADHD follow-up: changes in effectiveness and growth after the end of treatment. Pediatrics, 2004a, 113:762-769.

58. [0051/0052] MTA Group, 2004b): MTA Cooperative Group. National Institute of Mental Health Multimodal Treatment Study of ADHD follow-up: 24-month outcomes of treatment strategies for ADHD. Pediatrics. 2004. 113:754-761.

59. [0051/0052] Jensen et al (2007): Jensen P, Arnold L, Swanson J, Vitiello B, Abikoff H, Greenhill L, Hechtman L, Hinshaw S, Pelham W, Wells K, Conners C, Elliott G, Epstein J, Hoza B, March J, Molina B et al. 3-year follow-up of the NIMH MTA study. J Am Acad Child Adolesc Psychiatry. 2007: 46:989-1002.

60. [0051/0052] Swanson et al (2007a): Swanson J, Elliott G, Greenhill L, Wigal T, Arnold L, Vitiello B, Hechtman L, Epstein J, Pelham W, Abikoff H, Newcorn J, Molina B, Hinshaw S, Wells K, Hoza B, Jensen P, Gibbons R, Hur K, Stchli A, Davies M, March J, Conners C, Caron M, Volkow N. Effects of stimulant medication on growth rates across 3 years in the MTA follow-up. J Am Acad Child Adolesc Psychiatry. 2007; 46:1015-27.

61. [0051/0052] Swanson et al (2007b): Swanson J, Hinshaw S, Arnold L, Gibbons R, Marcus S, Hur K, Jensen P, Vitiello B, Abikoff H, Greenhill L, Hechtman L, Pelham W et al. Secondary evaluations of MTA 36-month outcomes: propensity score and growth mixture model analyses. J Am Acad Child Adolesc Psychiatry. 2007; 46:1003-1014.

62. [0051/0052] Molina et al (2007): Molina B, Flory K, Hinshaw S, Greiner A, Arnold L, Swanson J, Hechtman L, Jensen P, Vitiello B, Hoza B, Pelham W, Elliott G, Wells K, Abikoff H, Gibbons R, Marcus S, Conners C, Epstein J, Greenhill L, March J, Newcorn J, Severe J, Wigal T. Delinquent behavior and emerging substance use in the MTA at 36 months: prevalence, course, and treatment effects. J Am Acad Child Adolesc Psychiatry. 2007; 46: 1028-1040.

63. [0051/0052] Molina et al (2009): Molina B, Hinshaw S, Swanson J, Arnold L, Vitiello B, Jensen P, Epstein J, Hoza B, Hechtman L, Abikoff H, Elliott G, Greenhill L, Newcorn J, Wells K, Wigal T, Gibbons R, Hur K, Houck P. The MTA at 8 years: Prospective follow-up of children treated for combined-type ADHD in a multisite study. J Am Acad Child Adolesc Psychiatry. 2009; 48: 484-500.

64. [0051/0052] Molina et al (2013): Molina B, Hinshaw S, Arnold L, Swanson J, Pelham W, Hechtman L, Hoza B, Epstein J, Wigal T, Abikoff H, Greenhill L, Jensen P, Wells K, Vitiello B, Gibbons R, Howard A, Houck P, Hur K, Lu B, Marcus S. Adolescent substance use in the Multimodal Treatment Study of ADHD (MTA) as a function of childhood ADHD, random assignment to childhood treatments, and subsequent medication. J Am Acad Child Adolesc Psychiatry. 2013; 52: 250-262.

65. [0051/0052] Sibley et al (2016): Sibley M, Swanson J, Arnold L, et al. Defining ADHD symptom persistence in adulthood: optimizing sensitivity and specificity. *Journal of Child Psychology and Psychiatry.* 2017; 58:655-62.

66. [0051/0052] Hechtman et al (2016): Hechtman L, Swanson J, Sibley M, et al. Functional adult outcomes 16 years after childhood diagnosis of attention-deficit/hyperactivity disorder: MTA results. *Journal of the American Academy of Child and Adolescent Psychiatry.* 2016; 55:937-44.

67. [0051/0052] Swanson et al (2017): Swanson J, Arnold L, Molina B, et al. Young adult outcomes in the follow up of the multimodal treatment study of ADHD: symptom persistence, source discrepancy, and height suppression. *Journal of Child Psychology and Psychiatry.* 2017; 58: 663-78.

68. 0052/0053 Safer and Allen (1976): Safer D and Allen R. Hyperactive Children: Diagnosis and Management: 1976, University Park Press, Baltimore.

69. [0052/0053] Greenhill and Osman (1991): L Greenhill and B Osman, Editors. *Ritalin: Theory and Management.* 1991; Mary Ann Liebert: New York City: NY.

70. [0052/0053] Swanson et al (1999): Swanson J, Gupta S, Guinta D, Flynn D, Agler D, Lerner M, Williams L, Shoulson I, Wigal, S. Acute tolerance to methyphenidate in the treatment of ADHD in children. Clin Pharmacol Ther. 1999; 66: 295-305.

71. [0052/0053] Greenhill et al (2003): Greenhill L, Swanson J, Steinhoff K, Fried J, Posner K, Lerner M, Wigal S, Clausen S, Zhang Y, Tulloch S. A pharmacokinetic/pharmaco-dynamic study comparing a single morning dose of Adderall to twice-daily dosing in children with ADHD. J Am Acad Child Adolesc Psychiat. 2003; 42: 1234-1241.

72. [0052/0053] Swanson et al (2002): Swanson J, Lerner M, Wigal T, Steinhoff K, Greenhill L, Posner K, Freid J, Wigal S. The use of a laboratory school protocol to evaluate concepts about efficacy and side effects of new formulations of stimulant medications. J Atten Disord. 2002; 6: S73-S88.

73. [0052/0053] Swanson et al (2000): Swanson J, Greenhill L, Pelham W, Wilens T, Wolraich M, Abikoff H, Atkins M, August G, Biederman J, Bukstein O, Conners C K, Efron L, Ficbelkorn K, Fried J, Hoffman M, Lambrecht L, Lerner M, Leventhal B, McBurnett K, Morse E, Palumbo D, Pfiffner L, Stein M, Wigal S, Winans E. Initiating Concerta (OROS methyphenidate HC1) qd in children with ADHD. J Clinical Research. 2000; 3: 9-76.

74. [0052/0053] Greenhill et al (2003): Greenhill L, Swanson J, Steinhoff K, Fried J, Posner K, Lerner M, Wigal S, Clausen S, Zhang Y, Tulloch S. A pharmacokinetic/pharmaco-dynamic study comparing a single morning dose of Adderall to twice-daily dosing in children with ADHD. J Am Acad Child Adolesc Psychiat. 2003; 42: 1234-1241.

75. [0052/0053] Swanson and Volkow (2009): Swanson J and Volkow N. Psycho-pharmacology: concepts and opinions about the use of stimulant medications. J Child Psychol Psychiatry. 2009; 50: 180-193.

76. [0053/0054] Bradley (1937): Bradley C. The behavior of children receiving benzedrine. The American Journal of Psychiatry. 1937; 94, 577-585.

77. [0053/0054] Polanczyk et al (2014): Polanczyk G, Willcutt E, Salum G et al. ADHD prevalence estimates across three decades: an updated systematic review and meta-regression analysis. Int J Epidemiol. 2014; 43: 434-442.

78. [0053/0054] IDEA (1994): Individuals with Disabilities Education Act. US Congress: Reauthorization of the Education for All Handicapped Children Act (Public Law 94-142).

79. [0053/0054] Raman et al (2019): Raman S, Man K, Bahmanyar S, Berard A, Bilder S, Boukhris T, Buchnell G, Crystal S, Furu K, Yang Y, Karsstad O, Kieler H, Kubota K, Lai E, Martikainen J, Maura G, Moore N, Montero D, Nakamura H, Pate A, Pottegard A, Pratt N L, Roughead E, Saint-Gerans D, Sturmer T, Su C, Zoega H, Sturkenbroom M, Chan E, Coghill D, Ip P, Wong I. Lancet Psychiatry. 2019; 5: 824-835.

80. [0053/0054] Gajria et al (2014): Gajria K, Mei, L, Sikirica V, Greven P, Zhong Y, Qin P, Xie J. Adherence, persistence, and medication discontinuation in patients with attention-deficit/hyperactivity disorder—a systematic literature review. Neuropsychiatric Disease and Treatment. 2014; 10, 1543-1569.

81. [0053/0054] Ahmed and Aslani (2013): Ahmed R and Aslani P. An update on medication adherence and persistence in children. Exper Rev Pharmacoeconomics Outcome Research. 2013; 13: 791-815.

82. [0053/0054] Vitiello et al (2001): Vitiello B, Severe J, Greenhill L, Arnold L, Abikoff H, Bukstein O, Elliott G, Hechtman L, Jensen P, Hinshaw S, March J, Newcorn J, Swanson J, and Cantwell D. Methylphenidate dosage for children with ADHD over time under controlled conditions. J Am Acad Child Adolesc Psychiat. 2001; 40: 188-196.

83. [0053/0054] Charach et al (2004): Charach A, Ickowicz A, and Schachar R. Stimulant treatment over five years: Adherence, effectiveness, and adverse effects. Journal of the American Academy of Child and Adolescent Psychiatry. 2004; 43: 559-567.

84. [0053/0054] Zetterviqst et al (2013): Zetterqvist J, Asherson P, Halldner L, Långstrçm N, Larsson H. Stimulant and non-stimulant ADHD drug use: total population study of trends and discontinuation patterns 2006-2009. Acta Psychiatr Scand, 2013: 128: 70-77.

85. [0053/0054] Miller et al (2004): Miller A, Lalonde C, and McGrail K. Children's persistence with methylphenidate therapy: A population-based study. Canadian Journal of Psychiatry. 2004; 49: 761-768.

86. [0054/0055] Pliszka et al (2007): Pliszka S and AACAP Workgroup. Practice Parameter for the Assessment and Treatment of Children and Adolescents with ADHD. J Am Acad Child Adolesc Psychiatry. 2007; 46: 894-921.

87. [0054/0055] Swanson, Lerner, and Williams (1995): Swanson J, Lerner M, Williams L. Letter to the Editor. More frequent diagnosis of attention deficit-hyperactivity disorder. New England Journal of Medicine. 1995; 333: 944.

88. [0054/0055] Swanson and Volkow (2009): Swanson J and Volkow N. Psycho-pharmacology: concepts and opinions about the use of stimulant medications. J Child Psychol Psychiatry. 2009; 50:180-193.

89. [0055/0056] Coghill (2022): Coghill D. The benefits and limitations of stimulants in treating ADHD. Curr Top Behav Neurosci. 2022; 57: 51-77.

90. [0055/0056] Molina and Swanson (2020): Molina B and Swanson J. Why are long term benefits of stimulant medication so difficult to detect? The ADHD Report. 2020; 28: 1-7.

91. [0055/0056] Faraone et al (2021): Faraone S, Banaschewski T, Coghill D et al. The World Federation of ADHD international consensus statement: 208 evidence-based conclusions about the disorder. Neuroscience Biobehavioral Reviews. 2021; 128: 789-818

92. [0055/0056] Barkley (2020): Barkley R, Matza L, Jensen P, Schor N, Katz J, Alpern I, Tomar E, Wiznitzer M, Bajnrauh H, Johnson T, Gauthier B, Gower-Getz A, Nadeau K, Tuckman A, Keepnews D, Hughes R, Cattoi R. The Adverse Health Outcomes, Economic Burden, and Public Health Implications of Unmanaged ADHD: A Call to Action to Improve the Quality of Life and Life Expectancy of People with ADHD. ADHD Public Health Summit. 2020; Washington DC.

93. [0056/0057] Cortese, Coghill, and Swanson (2019): Cortese S, Swanson J, Coghill D. Debate: Are stimulant medications for Attention-Deficit/Hyperactivity Disorder Effective in the Long Term? J Amer Acad Child and Adolescent Psychiatry. 2019; 58: 936-139.

94. [0056/0057] Swanson et al (2002): Swanson J, Lerner M, Wigal T, Steinhoff K, Greenhill L, Posner K, Freid J, Wigal S. The use of a laboratory school protocol to evaluate concepts about efficacy and side effects of new formulations of stimulant medications. J Atten Disord. 2002; 6: S73-S88.

95. [0056/0057] Swanson et al (2017): Swanson J, Arnold L, Molina B, et al. Young adult outcomes in the follow up of the multimodal treatment study of ADHD: symptom persistence, source discrepancy, and height suppression. Journal of Child Psychology and Psychiatry. 2017; 58: 663-78.

96. [0056/0057] Miller et al (2004): Miller A, Lalonde C, and McGrail K. Children's persistence with methylphenidate therapy: A population-based study. Canadian Journal of Psychiatry. 2004; 49: 761-768.

97. [0056/0057] Zetterviqst et al (2013): Zetterqvist J, Asherson P, Halldner L, Långstrçm N, Larsson H. Stimulant and non-stimulant ADHD drug use: total population study of trends and discontinuation patterns 2006-2009. Acta Psychiatr Scand, 2013: 128: 70-77.

98. [0056/0057] Wong et al (2019): Raman S, Man K, Bahmanyar S, Berard A, Bilder S, Boukhris T, Buchnell G, Crystal S, Furu K, Yang Y, Karsstad O, Kieler H, Kubota K, Lai E, Martikainen J, Maura G, Moore N, Montero D, Nakamura H, Pate A, Pottegard A, Pratt N, Roughead E, Saint-Gerans D, Sturmer T, Su C, Zoega H, Sturkenbroom M, Chan E, Coghill D, Ip P, Wong I. Lancet Psychiatry. 2019; 5: 824-835.

99. [0056/0057] Lawson et a (2012): Lawson K, Johnsrud M, Hodgkins P, Sasané R, Crismon M. Utilization Patterns of Stimulants in ADHD in the Medicaid Population. Clinical Therapeutics. 2012; 34: 944-956.

100. [0056/0057] Biederman et al (2019): Biederman J, Fried R, DiSalvo M, Storch B, Pulli A, Woodworth K, Biederman I, Faraone S, Perlis R. Evidence of low adherence to stimulant medication among children and youths with ADHD: An Electronic Health Records Study. Psychiatric Services, 2019: 70: 874-880

101. [0056/0057] Coghill (2019): Coghill D. Proponent: Are stimulant medications for Attention-Deficit/Hyperactivity Disorder Effective in the Long Term? J Amer Acad Child and Adolescent Psychiatry, 2019; 58: 936-139.

102. [0056/0057] Marcus and Durkin (2011): Marcus S and Durkin M. Stimulant adherence and academic performance in urban youth with attention-deficit/hyperactivity disorder. Journal of the American Academy of Child and Adolescent. Psychiatry, 2011; 50: 480-489

103. [0056/0057] Swanson et al (2023): Swanson J. Invited Presentation (Hot Topic: Special Issues on Pharmacological Treatment of ADHD): Acute and late tolerance: Are these real problems using stimulants? World Federation of ADHD. 2023: Amsterdam 104. [0058/0059] Volkow et al (2017): Volkow N, Wiers C, Shokri-Kojori E, Tomasi D, Wang G-J, Baler R. Neurochemical and metabolic effects of acute and chronic alcohol in the human brain: Studies with PET. Neuropharm. 2017; 122: 175-188.

105. [0058/0059] Volkow et al (2002): Volkow N, Wang G-J, Fowler J, Logan J, Franceschi D, Maynard L, Ding Y, Gatley S, Gifford A, Zhu W, Swanson J. Relationship between blockade of dopamine transporters by oral methylphenidate and the increases in extracellular dopamine: therapeutic implications. Synapse. 2002; 43:181-187.

106. [0058/0059] Volkow et al (2009): Volkow N, Wang G-J, Kollins S, Wigal T, Newcorn J, Telang F, Fowler J, Zhu W, Logan J, Ma Y, Pradhan K, Wong C, Swanson J. Evaluating dopaminc reward pathway in ADHD: clinical implications. JAMA. 2009; 302: 1084-1091.

107. [0058/0059] Volkow and Swanson (2008): Volkow N and Swanson J. Basic Neuro-psychopharmacology. In M Rutter (Ed.), Rutter's Child and Adolescent Psychiatry, 5th Edition. Blackwell Publishing. 2008; 212-233.

108. [0059/0060] Volkow et al (1995): Volkow D, Ding Y, Fowler J, Wang G-J, Logan J, Gatley J S, Dewey S, Ashby C, Liebermann J, Hitzemann R, et al. Is methylphenidate like cocaine? Studies on their pharmacokinetics and distribution in the human brain. Arch Gen Psychiatry, 1995; 52: 456-463.

109. [0059/0060] Volkow et al (2007): Volkow N, Wang G-J, Newcorn J, Fowler J, Telang F, Solanto M, Logan J, Wong C, Ma Y, Swanson J, Schulz K, Pradhan K. Brain dopamine transporter levels in treatment and drug naïve adults with ADHD. NeuroImage. 2007; 34: 1182-1190.

110. [0059/0060] Volkow et al (2009): Volkow N, Wang G-J, Kollins S, Wigal T, Newcorn J, Telang F, Fowler J, Zhu W, Logan J, Ma Y, Pradhan K, Wong C, Swanson J. Evaluating dopamine reward pathway in ADHD: clinical implications. JAMA. 2009; 302: 1084-1091.

111. [0059/0060] Wang et al (2013): Wang G J, Volkow N D, Wigal T, Kollins S H, Newcorn J H, Telang F, Logan J, Jayne M, Wong C T, Han H, Fowler J S, Zhu W, Swanson J M. Long-term stimulant treatment affects brain dopamine transporter level in patients with attention deficit hyperactive disorder. PLoS One. 2013; 15; 8: e63023.

112. [0060/0061] Grace et al (2019): Grace A and Gomes F. The Circuitry of Dopamine System Regulation and its Disruption in Schizophrenia: Insights into Treatment and Prevention: Review. Schizophr Bull: 2019; 45(1): 148-157.

113. [0061/0062] Grace (2001): Grace A. Psychostimulant actions on dopamine and limbic system function: Relevance to the pathophysiology and treatment of ADHD. In M Solanto, A Arnsten, and F Castellanos (Editors): Stimulant Drugs and ADHD: Basic and Clinical Neuroscience. 2001; Oxford University Press: New York NY.

114. [0061/0062] Grace (2000): Grace A. The tonic/phasic model of dopamine system regulation and its implications for understanding drug and alcohol craving. Addiction. 2000; Suppl 2: S119-128.

115. [0061/0062] Goto and Grace (2005): Goto Y and Grace A. Dopaminergic modulation of limbic and cortical drive of nucleus accumbens in goal-directed behavior. Nature Neuroscience: 2005; 8: 805-812.

116. [0061/0062] Goto and Grace (2007): Goto Y, Otani S, and Grace A. The Yin and Yang of dopamine release: a new perspective. Neuropharm Mini-review. 2007; 53: 583e587.

117. [0068/0069] Volkow et al (2002): Volkow N, Wang G, Fowler J, Logan J, Franceschi D, Maynard L, Ding Y, Gatley S, Gifford A, Zhu W, Swanson J. Relationship between blockade of dopamine transporters by oral methylphenidate and the increases in extracellular dopamine: therapeutic implications. Synapse. 2002; 43: 181-187.

118. [0068/0069] Volkow et al (2007): Volkow N, Wang G, Newcorn J, Fowler J, Telang F, Solanto M, Logan J, Wong C, Ma Y, Swanson J, Schulz K, Pradhan K. Brain dopamine transporter levels in treatment and drug naïve adults with ADHD. NeuroImage. 2007; 34: 1182-1190.

119. [0068/0069] Wang et al (2013): Wang G-J, Volkow N, Wigal T, Kollins S, Newcorn J, Telang F, Logan J, Jayne M, Wong C, Han H, Fowler J, Zhu W, Swanson J. Long-term stimulant treatment affects brain dopamine transporter level in patients with attention deficit hyperactive disorder. PLoS One. 2013, 8: e63023.

120. [0069/0070] Swanson (2012): Swanson J. Short and Long-term Tolerance to Stimulant Medication. Presentation at AACAP. 2012; San Francisco CA.

121. [0070/0079] Faraone et al (2021): Faraone S, Banaschewski T, Coghill D . . . and Wang Y. The World Federation of ADHD international consensus statement: 208 evidence-based conclusions about the disorder. Neuroscience Biobehavioral Reviews, 2021; 128:789-818.

122. [0070/0071] INCD (2020): United Nations, International Narcotics Control Board (INCB). 2020: Annual Report Psychotropic Substances. New York City: NY.

123. [0070/0071] Storebo et al (2015): Storebo O, Ramstad E, Krough H, Nilausen T, Skoog M, Holmskov M, Rosendal S, Groth C, Magnusson F et al. Methylphenidate for children and adolescents with ADHD, Cochrane Library Review. 2015; 11: 1-766.

124. [0070/0071] Cortese et al (2018): Cortese S, Adamo N, del Glovane C, Mahr-Jensen C, Mayes A, Carucci S, Atkinson L Z, Tessari L, Banaschewski T, Coghill D, Hollis C, Simonhoff E, Zuddas A, Barbui C, Purgato M, Steinhausen H-C, Shokranch F, Xia J, and Cipriani A. Comparative efficacy and tolerability of medications for attention-deficit hyperactivity disorder in children, adolescents, and adults: a systematic review and network meta-analysis. Lancet Psychiatry, 2018; 5: 727-738.

125. [0070/0071] Bhat and Hechtman et al (2016): Bhat V and Hechtman L. Considerations for selecting treatments for ADHD. Clinical Pharmacist. 2016. 8: 1-5.

126. [0070/0071] Molina and Swanson (2020): Molina B and Swanson J. Why Are Long-term Benefits of Stimulant Medication So Difficult to Detect? The ADHD Report. 2020; 28: 1-7.

127. [0070/0071] Gajria et al (2014): Gajria K, Mei, L, Sikirica V, Greven P, Zhong Y, Qin P, Xie J. Adherence, persistence, and medication discontinuation in patients with attention-deficit/hyperactivity disorder—a systematic literature review. Neuropsychiatric Disease and Treatment. 2014; 10, 1543-1569.

128. [0070/0071] Ahmed and Aslani (2013): Ahmed R and Aslani P. An update on medication adherence and persistence in children. Exper Rev Pharmacoeconomics Outcome Research. 2013; 13: 791-815.

129. [0070/0071] Charach and Fernandez (2013): Charach A and Fernandez R. Enhancing ADHD Medication Adherence: Challenges and Opportunities. Curr Psychiatry Reports, 2013; 15: 371-378.

130. [0071/0072] Cortese et al (2019): Cortese S, Swanson J, Coghill D. Debate: Are stimulant medications for Attention-Deficit/Hyperactivity Disorder Effective in the Long Term? J Amer Acad Child and Adolescent Psychiatry. 2019; 58: 936-139.

131. [0071/0072] Coghill (2019): Coghill D. Proponent: Are stimulant medications for Attention-Deficit/Hyperactivity Disorder Effective in the Long Term? J Amer Acad Child and Adolescent Psychiatry; 2019; 58: 936-139.

132. [0071/0072] Swanson (2019): Swanson J. Opponent: Are stimulant medications for Attention-Deficit/Hyperactivity Disorder Effective in the Long Term? J Amer Acad Child and Adolescent Psychiatry. 2019; 58: 936-139.

133. [0095/0096] Polanczyk et al (2014): Polanczyk G, Willcutt E, Salum G et al. ADHD prevalence estimates across three decades: an updated systematic review and meta-regression analysis. Int J Epidemiol. 2014; 43: 434-442.

134. [0095/0096] Faraone et al (2021): Faraone S, Banaschewski T, Coghill D et al. The World Federation of ADHD international consensus statement: 208 evidence-based conclusions about the disorder. Neuroscience Biobehavioral Reviews. 2021; 128: 789-818.

135. [0095/0096] DSM-II (1968): Diagnostic and Statistical Manual of the American Psychiatric Association: Edition II. APA. 1968; Washington DC.

136. [0095/0096] DSM-5 (2013): Diagnostic and Statistical Manual of the American Psychiatric Association: Edition 5. APA, 2013; Washington DC.

137. [0096/0097] Bradley (1937): Bradley C. The behavior of children receiving benzedrine. The American Journal of Psychiatry. 1937; 94: 577-585.

138. [0096/0097] Bradley (1950): Bradley C. Benzedrine and dexedrine in the treatment of children's behavior disorders. Pediatrics. 1950; 5: 24-37.

139. [0096/0097] DSM-II (1968): Diagnostic and Statistical Manual (DSM), Edition II. Ametican Psychiatric Association. 1968: Washington DC.

140. [0096/0098] Wender (1971): Wender P. Minimal Brain Dysfunction in Children. Wiley-Interscience. 1971; New York City, NY 141. [0096/0097] Greenhill and Osman (1991): Greenhill L. Methylphenidate in the Clinical Office Practice of Child Psychiatry. In L Greenhill and B Osman (Editors): Ritalin: Theory and Patient Management: Mary Ann Liebert. 1991; New York City, NY.

142. [0097/0098] Safer and Allen (1976): Safer D and Allen R. Hyperactive Children: Diagnosis and Management. University Park Press. 1976; Baltimore, MD.

143. [0097/0098] DSM-III (1980): Diagnostic and Statistical Manual of the American Psychiatric Association: Edition III. APA. 1980; Washington DC.

144. [0097/0098] Shaywitz et al (1982): Shaywitz S, Hunt R, et al. Psychopharmacology of attention disorder: Pharmacokinetic neuroendocrine and behavioral measures following acute and chronic treatment with methylphenidate. Pediatrics. 1982; 6: 688-694.

145. [0097/1998] Swanson et al (1978): Swanson J, Kinsbourne M, Roberts W, Zucker K. Time-response analysis of the effect of stimulant medication on the learning ability of children referred for hyperactivity. Pediatrics. 1978; 61: 21-2.

146. [0098/0099] Safer and Allen (1989): Safer D and Allen R. Absence of tolerance to the behavioral effects of methylphenidate in hyperactive and inattentive children. J Pediatrics. 1989; 115: 1003-1008.

147. [0099/0100] Swanson et al (1978): Swanson J, Kinsbourne M, Roberts W, Zucker K. Time-response analysis of the effect of stimulant medication on the learning ability of children referred for hyperactivity. Pediatrics. 1978; 61: 21-29.

148. [0099/0100] Swanson et al (1991): Swanson J, Cantwell D, Lerner M, Hanna G. Effects of stimulant medication on learning in children with ADHD. Journal Learning Disability. 1991; 24:219-229.

149. [0100/0101] Pelham et al (1995): Pelham W, Swanson J, Bender M, and Schwindt H. Pemoline Effects on Children with ADHD: A Time-Response by Dose-Response Analysis on Classroom Measures.] Am Acad Child Adolesc Psychiatry. 1995; 34: 1504-1513.

150. [0100/0101] Swanson et al (1998): Swanson J, Wigal S, Greenhill L, Browne R, Waslik B, Lerner M, Williams L, Flynn D, Agler D, Crowley K, Fineberg E, Baren M, Cantwell D. Analog classroom assessment of Adderall in children with ADHD. J Am Acad Child Adolesc Psychiatry. 1998; 37: 519-526.

151. [0100/0101] MTA Group (1999): MTA Cooperative Group. A 14-month randomized clinical trial of treatment strategies for ADHD. Arch Gen Psychiatry. 1999; 56: 1073-1086.

152. [0101/0102] Vitiello et al (2001): Vitiello B, Severe J, Greenhill L, Arnold L, Abikoff H, Bukstein O, Elliott G, Hechtman L, Jensen P, Hinshaw S, March J, Newcorn J, Swanson J, and Cantwell D. Methylphenidate dosage for children with ADHD over time under controlled conditions: lessons from the MTA. J Am Acad Child Adolesc Psychiat. 2001; 40: 188-196.

153. [0102/1103] Greenhill and Osman (1991): Greenhill L. Methylphenidate in the Clinical Office Practice of Child Psychiatry. In L Greenhill and B Osman (Editors): Ritalin: Theory and Patient Management: Mary Ann Liebert. 1991; New York City, NY.

154. [0102/0103] Swanson, Lerner, and Williams (1995): Swanson J, Lerner M, Williams L. Letter to the Editor. More frequent diagnosis of attention deficit-hyperactivity disorder. New England Journal of Medicine. 1995; 333: 944

155. [0103/0104] Greenhill et al (1987): Fried J, Greenhill L, Torres D, Martin J, Solomon M. Sustained-release methylphenidate: long-term clinical efficacy in ADDH males. Am Acad Child Adolesc Psychiatry: Sci. Proc Annual Meeting. 1987; 3:47.

156. [0103/0104] Swanson et al (1991): Swanson J, Cantwell D, Lerner M, Hanna G. Effects of stimulant medication on learning in children with ADHD. Journal of Learning Disabilities. 1991; 24: 219-229.

157. [0104/0105] Swanson et al (1999): Swanson J, Gupta S, Guinta D, Flynn D, Agler D, Lerner M, Williams L, Shoulson I, Wigal, S. Acute tolerance to methylphenidate in the treatment of ADHD in children. Clin Pharmacol Ther. 1999; 66: 295-305.

158. [0105/0106] Swanson et al (2003): Swanson J, Gupta S, Lam A, Shoulson I, Lerner M, Modi N, Lindemulder E, Wigal S. Development of a new once-a-day formulation of methylphenidate for the treatment of ADHD: Proof-of-concept and proof-of-product studies. Arc Gen Psychiatry. 2003; 60: 204-211.

159. [0106/0107] Swanson et al (2004): Swanson J, Wigal S, Wigal T, Sonuga-Barke E, Greenhill L, Biederman J, Kollins S, Nguyen A, DeCory H, Hirshey-Dirksen S, Hatch S, COMACS Study Group. A comparison of once-daily extended-release methylphenidate formulations in children with attention-deficit/hyperactivity disorder in the laboratory school (The COMACS Study). Pediatrics. 2004; 113: e206-e216.

160. [0106/0107] Wigal et al (2003): Wigal S, Sanchez D, DeCory H, D'Imperio J, Swanson J. Selection of the optimal dose ratio for a controlled-delivery formulation of methylphenidate. The Journal of Applied Research. 2003; 3: 46-63.

161. [0107/0108] Swanson et al (1998): Swanson J, Wigal S, Greenhill L, Browne R, Waslik B, Lerner M, Williams L, Flynn D, Agler D, Crowley K, Fineberg E, Regino R, Baren M, Cantwell D. Objective and subjective measures of the pharmacodynamic effects of Adderall in the treatment of children with ADHD in a controlled laboratory classroom setting. Psychopharm Bulletin. 1998; 34: 55-60.

162. [0107/0108] Swanson et al (1998): Swanson J, Wigal S, Greenhill L, Browne R, Waslik B, Lerner M, Williams L, Flynn D, Agler D, Crowley K, Fineberg E, Baren M, Cantwell D. Analog classroom assessment of Adderall in children with ADHD. J Am Acad Child Adolesc Psychiatry. 1998; 37: 519-526.

163. [0107/0108] Greenhill et al (2003): Greenhill L L, Swanson J M, Steinhoff K, Fried J, Posner K, Lerner M, Wigal S, et al. A pharmacokinetic pharmacodynamic study comparing a single morning dose of Adderall to twice-daily dosing in children with ADHD. J Am Acad Child Adolesc Psychiatry; 2003; 42: 1234-1241.

164. [0107/0108] McGough et al (2003): McGough J, Biederman J, Greenhill L, McCracken J, Spencer T, Posner K, Wigal S, Gornbein J, Tulloch S, Swanson J. Pharmacokinetics of SLI381, an extended-release formulation of Adderall. J Am Acad Child Adolesc Psychiat; 2003, 42: 684-691.

165. [0107/0108] Greenhill et al (2003): Greenhill L, Swanson J, Steinhoff K, Fried J, Posner K, Lerner M, Wigal S, Clausen S, Zhang Y, Tulloch S. A pharmacokinetic/pharmacodynamic study comparing a single morning dose of Adderall to twice-daily dosing in children with ADHD. J Am Acad Child Adolesc Psychiatry. 2003; 42: 1234-1241.

166. [0107/0108] McCracken et al (2003): McCracken J, Biederman J, Greenhill L, Swanson J, McGough J, Spencer T, Posner K, Wigal S, Pataki C, Zhang Y, Tulloch S. Analog classroom assessment of a once-daily mixed amphetamine formulation, SLI381 (Adderall XR) in children with ADHD. J Am Acad Child Adolesc Psychiat; 2003, 42: 673-683.

167. [0109/1110] Pliszka et al (2007): Pliszka S and AACAP Workgroup. Practice parameter for the assessment and treatment of children and adolescents with ADHD. J Am Acad Child Adolesc Psychiatry, 2007, 46: 894-921.

168. [1009/0110] NICE (2018): National Institute on Clinical Excellence. NICE guideline: 2018 (Update on 14 Mar. 2018), www.nice.org.uk/guidance/ng87

169. [0109/0110] Walkup et al (2009): Walkup J and Work Group on Quality Issues. Practice Parameter on the Use of Psychotropic Medication in Children and Adolescents, J Am Acad Child Adolesc Psychiatry, 2009, 48: 961-973.

170. [0109/1110] Wolraich et al (2019): Wolraich M, Hagan J, Allan C, Chan E, Davison D, Earls M, Evans S, Flinn S, Frochlich T, Frost J, Holbrook J, Lehmann C, Lessin H, Okechukwu K, Pierce K, Winner J, Zurhellen W for the Subcommittee on Children and Adolescents with ADHD. Pediatrics, 2019, 144: 1-25.

171. [0109/0110] Faraone et al (2021): Faraone S, Banaschewski T, Coghill D, Zheng Y, Biederman J, Bellgrove M, et al. The World Federation of ADHD international consensus statement: 208 evidence-based conclusions about the disorder. Neuroscience & Biobehavioral Reviews. 2021, 128: 789-818.

172. [0109/0110] Storebo et al (2015): Storebo O, Ramstad E, Krough H, Nilausen T, Skoog M, Holmskov M, Rosendal S, Groth C, Magnusson F et al. Methyl-phenidate for children and adolescents with ADHD, Cochrane Library Review, 2015; 11: 1-766.

173. [0109/0110] Cortese et al (2018): Cortese S, Adamo N, del Glovane C, Mahr-Jensen C, Mayes A, Carucci S, Atkinson L Z, Tessari L, Banaschewski T, Coghill D, Hollis C, Simonhoff E, Zuddas A, Barbui C, Purgato M, Steinhausen H-C, Shokranch F, Xia J, and Cipriani A. Comparative efficacy and tolerability of medications for attention-deficit hyperactivity disorder in children, adolescents, and adults: a systematic review and network meta-analysis. Lancet Psychiatry. 2018; 5: 727-738.

174. [0109/0110] Faraone et al (2021): Faraone S, Banaschewski T, Coghill D et al. The World Federation of ADHD international consensus statement: 208 evidence-based conclusions about the disorder. Neuroscience Biobehavioral Reviews. 2021; 128: 789-818.

175. [0110/0111] Swanson et al (2012): Swanson J. Short and Long-term Tolerance to Stimulant Medication. Presentation at AACAP 2012. San Francisco CA.

176. [0110/0111] Greenhill et al (2003): Greenhill L, Swanson J, Steinhoff K, Fried J, Posner K, Lerner M, Wigal S, Clausen S, Zhang Y, Tulloch S. A pharmacokinetic/pharmacodynamic study comparing a single morning dose of Adderall to twice-daily dosing in children with ADHD. J Am Acad Child Adolesc Psychiatry. 2003; 42: 1234-1241.

177. [0110/0111] McCracken et al (2003): McCracken J, Biederman J, Greenhill L, Swanson J, McGough J, Spencer T, Posner K, Wigal S, Pataki C, Zhang Y, Tulloch S. Analog classroom assessment of a once-daily mixed amphetamine formulation, SLI381 (Adderall XR) in children with ADHD._J Am Acad Child Adolesc Psychiat. 2003: 42: 673-683.

178. [0110/0111] Swanson et al (2004): Swanson J, Wigal S, Wigal T, Sonuga-Barke E, Greenhill L, Biederman J, Kollins S, Nguyen A, DeCory H, Hirshey-Dirksen S, Hatch S, COMACS Study Group. A comparison of once-daily extended-release methylphenidate formulations in children with attention-deficit/hyperactivity disorder in the laboratory school (The COMACS Study). Pediatrics. 2004; 113: e206-e216.

179. [0110/0111] Wigal et al (2003): Wigal S, Sanchez D, DeCory H, D'Imperio J, Swanson J. Selection of the optimal dose ratio for a controlled-delivery formulation of methylphenidate. The Journal of Applied Research. 2003; 3: 46-63.

180. [0111/0112] MTA Group (1999a): MTA Cooperative Group. A 14-month randomized clinical trial of treatment strategies for attention deficit hyperactivity disorder. Arch Gen Psychiatry. 1999; 56: 1073-108.

181. [0111/0112] Philipsen et al (2015): Philipsen A, Jans T, Graf E, Matthies S, Borel P, Colla M, Gentschow L, Langner D, Jacob C, Groβ-Lesch S, Sobanski E, Alm B, Schumacher-Stien M, Roesler M, Retz W, Retz-Junginger P, Kis B, Abdel-Hamid Heinrich V, Huss M, Kornmann C, Bürger A, Perlov E, Ihorst G, Schlander M, Berger M, Tebartz van Elst M, for the Comparison of Methylphenidate and Psychotherapy in Adult ADHD Study (COMPAS) Consortium. Effects of Group Psychotherapy, Individual Counseling, Methylphenidate, and Placebo in the Treatment of Adult ADHD: A Randomized Clinical Trial. JAMA Psychiatry. 2015; 72:1199-1210.

182. [0112/0113] MTA Group (1999b): MTA Cooperative Group. Moderators and mediators of treatment response for children with attention-deficit/hyperactivity disorder. Arch Gen Psychiatry. 1999; 56: 1088-1096.

183. [0113/0114] Faraone et al (2021): Faraone S V, Banaschewski T, Coghill D, et al. The World Federation of ADHD international consensus statement: 208 evidence-based conclusions about the disorder. Neuroscience Biobehavioral Reviews. 2021; 128: 789-818.

184. [0113/0114] Hechtman et al (2016): Hechtman L, Swanson J, Sibley M, et al. Functional adult outcomes 16 years after childhood diagnosis of ADHD: MTA results. *Journal of the American Academy of Child and Adolescent Psychiatry.* 2016; 55: 937-44.

185. [0114/0115] Gajria et al (2014): Gajria K, Mei, L, Sikirica V, Greven P, Zhong Y, Qin P, Xie J. Adherence, persistence, and medication discontinuation in patients with attention-deficit/hyperactivity disorder—a systematic literature review. Neuropsychiatric Disease and Treatment. 2014; 10, 1543-1569.

186. [0114/0115] Ahmed and Aslani (2013): Ahmed R and Aslani P. An update on medication adherence and persistence in children. Exper Rev Pharmacoeconomics Outcome Research. 2013; 13: 791-815.

187. [0114/0115] Vrijens et al (2012): Vrijens B et al. A new taxonomy for describing and defining adherence to medications. Br J Clin Pharmacol. 2012; 73:691-705

188. [0115/0116] Storebo et al (2015): Storebo O, Ramstad E, Krough H, Nilausen T, Skoog M, Holmskov M, Rosendal S, Groth C, Magnusson F, Moreira-Maia C, Gillies D, Ramussen K, Gauci D, Zwi M, Kirubakaran R, Forsbol B, Simonsen E, and Gluud C. Methylphenidate for children and adolescents with ADHD, Cochrane Library Review. 2015; 11; 1-766.

189. [0115/0116] MTA Group (1999): MTA Cooperative Group. A 14-month randomized clinical trial of treatment strategies for attention deficit hyperactivity disorder. Arch Gen Psychiatry. 1999; 56: 1073-1086.

190. [0115/0116] Cortese et al (2018): Cortese S, Adamo N, del Glovane C, Mahr-Jensen C, Mayes A, Carucci S, Atkinson L Z, Tessari L, Banaschewski T, Coghill D, Hollis C, Simonhoff E, Zuddas A, Barbui C, Purgato M, Steinhausen H-C, Shokranch F, Xia J, and Cipriani A. Comparative efficacy and tolerability of medications for attention-deficit hyperactivity disorder in children, adolescents, and adults: a systematic review and network meta-analysis. Lancet Psychiatry. 2018; 5: 727-738.

191. [0115/0116] Philipsen et al (2015): Philipsen A, Jans T, Graf E, Matthies S, Borel P, Colla M, Gentschow L, Langner D, Jacob C, Groß-Lesch S, Sobanski E, Alm B, Schumacher-Stien M, Roesler M, Retz W, Retz-Junginger P, Kis B, Abdel-Hamid Heinrich V, Huss M, Kornmann C, Bürger A, Perlov E, Ihorst G, Schlander M, Berger M, Tebartz van Elst M, for the Comparison of Methylphenidate and Psychotherapy in Adult ADHD Study (COMPAS) Consortium. Effects of Group Psychotherapy, Individual Counseling, Methylphenidate, and Placebo in the Treatment of Adult ADHD: A Randomized Clinical Trial. JAMA Psychiatry. 2015; 72: 1199-1210.

192. [0116/0117] Storebo et al (2015): Storebo O, Ramstad E, Krough H, Nilausen T, Skoog M, Holmskov M, Rosendal S, Groth C, Magnusson F et al. Methylphenidate for children and 193. [0116/0117] Cortese et al (2018): Cortese S, Adamo N, del Glovane C, Mahr-Jensen C, Mayes A, Carucci S, Atkinson L Z, Tessari L, Banaschewski T, Coghill D, Hollis C, Simonhoff E, Zuddas A, Barbui C, Purgato M, Steinhausen H-C, Shokranch F, Xia J, and Cipriani A. Comparative efficacy and tolerability of medications for attention-deficit hyperactivity disorder in children, adolescents, and adults: a systematic review and network meta-analysis. Lancet Psychiatry, 2018; 5: 727-738.

194. [0116/0117] Storebo et al (2015): Storebo O, Ramstad E, Krough H, Nilausen T, Skoog M, Holmskov M, Rosendal S, Groth C, Magnusson F et al. Methylphenidate for children and adolescents with ADHD, Cochrane Library Review. 2015; 11: 1-766.

195. [0116/0117] MTA Group (1999): MTA Cooperative Group. A 14-month randomized clinical trial of treatment strategies for attention deficit hyperactivity disorder. Arch Gen Psychiatry. 1999; 56: 1073-1086.

196. [0116/0117] Cortese et al (2018): Cortese S, Adamo N, del Glovane C, Mahr-Jensen C, Mayes A, Carucci S, Atkinson L Z, Tessari L, Banaschewski T, Coghill D, Hollis C, Simonhoff E, Zuddas A, Barbui C, Purgato M, Steinhausen H-C, Shokranch F, Xia J, and Cipriani A. Comparative efficacy and tolerability of medications for attention-deficit hyperactivity disorder in children, adolescents, and adults: a systematic review and network meta-analysis. Lancet Psychiatry. 2018; 5: 727-738.

197. [0116/0117] Philipsen et al (2015): Philipsen A, Jans T, Graf E, Matthies S, Borel P, Colla M, Gentschow L, Langner D, Jacob C, Groß-Lesch S, Sobanski E, Alm B, Schumacher-Stien M, Roesler M, Retz W, Retz-Junginger P, Kis B, Abdel-Hamid Heinrich V, Huss M, Kornmann C, Bürger A, Perlov E, Ihorst G, Schlander M, Berger M, Tebartz van Elst M, for the Comparison of Methylphenidate and Psychotherapy in Adult ADHD Study (COMPAS) Consortium. Effects of Group Psychotherapy, Individual Counseling, Methylphenidate, and Placebo in the Treatment of Adult ADHD: A Randomized Clinical Trial. JAMA Psychiatry. 2015; 72: 1199-1210.

198. [0117/0118] Cortese et al (2018): Cortese S, Adamo N, del Glovane C, Mahr-Jensen C, Mayes A, Carucci S, Atkinson L Z, Tessari L, Banaschewski T, Coghill D, Hollis C, Simonhoff E, Zuddas A, Barbui C, Purgato M, Steinhausen H-C, Shokranch F, Xia J, and Cipriani A. Comparative efficacy and tolerability of medications for attention-deficit hyperactivity disorder in children, adolescents, and adults: a systematic review and network meta-analysis. Lancet Psychiatry, 2018; 5: 727-738.

199. [0117/0118] Storebo et al (2015): Storebo O, Ramstad E, Krough H, Nilausen T, Skoog M, Holmskov M, Rosendal S, Groth C, Magnusson F, et al. Methylphenidate for children and adolescents with ADHD, Cochrane Library Review. 2015; 11: 1-766.

200. [0117/0118] Cortese et al (2018): Cortese S, Adamo N, del Glovane C, Mahr-Jensen C, Mayes A, Carucci S, Atkinson L, Tessari L, Banaschewski T, Coghill D, Hollis C, Simonhoff E, Zuddas A, Barbui C, Purgato M, Steinhausen H-C, Shokranch F, Xia J, and Cipriani A. Comparative efficacy and tolerability of medications for attention-deficit hyperactivity disorder in children, adolescents, and adults: a systematic review and network meta-analysis. Lancet Psychiatry. 2018; 5:727-738.

201. [0118/0119] Gajria et al (2014): Gajria K, Mei, L, Sikirica V, Greven P, Zhong Y, Qin P, Xie J. Adherence, persistence, and medication discontinuation in patients with attention-deficit/hyperactivity disorder—a systematic literature review. Neuropsychiatric Disease and Treatment. 2014; 10, 1543-1569.

202. [0118/0119] Ahmed and Aslani (2013): Ahmed R and Aslani P. An update on medication adherence and persistence in children. Exper Rev Pharmacoeconomics Outcome Research. 2013:13: 791-815.

203. [0119/0120] MTA Group (2004): MTA Cooperative Group. National Institute of Mental Health Multimodal Treatment Study of ADHD follow-up: changes in effectiveness and growth after the end of treatment. Pediatrics, 2004, 113: 762-769.

204. [0119/0120] Lam et al (2019): Lam A, Matthies S, Graf E, Colla M, Jacob C, Sobanski E, Alm B, Rösler M, Retz W, Retz-Junginger P, Kis B, Abdel-Hamid M, Müller H, Lücke C, Huss M, Jans T, Berger M, Tebartz van Elst L, Philipsen A for the Comparison of Methylphenidate and Psychotherapy in Adult ADHD Study (COMPAS) Consortium. Long-term Effects of Multimodal Treatment on Adult ADHD Symptoms: Follow-up Analysis of the COMPAS Trial, JAMA Network Open. 2019; 2:e194980, 1-17.

205. [0119/0120] Jensen et al (2007): Jensen P, Arnold L, Swanson J, Vitiello B, Abikoff H, Greenhill L, Hechtman L, Hinshaw S, Pelham W, Wells K, Conners C, Elliott G, Epstein J, Hoza B, March J, Molina B, Newcorn J, Severe J, Wigal T, Gibbons R, Hur K. 3-year follow-up of the NIMH MTA. J Am Acad Child Adolesc Psychiatry. 2007; 46: 989-1002.

206. [0119/0120] Swanson et al (2007a): Swanson J, Elliott G, Greenhill L, Wigal T, Arnold L, Vitiello B, Hechtman L, Epstein J, Pelham W, Abikoff H, Newcorn J, Molina B, Hinshaw S, Wells K, Hoza B, Jensen P, Gibbons R, Hur K, Stehli A, Davies M, March J, Conners C, Caron M, Volkow N. Effects of stimulant medication on growth rates across 3 years in the MTA follow-up. J Am Acad Child Adolesc Psychiatry. 2007; 46: 1015-27.

207. [0119/0120] Swanson et al (2007b): Swanson J, Hinshaw S, Arnold L, Gibbons R, Marcus S, Hur K, Jensen P, Vitiello B, Abikoff H, Greenhill L, Hechtman L, Pelham W, et al. Secondary evaluations of MTA 36-month outcomes: propensity score and growth mixture model analyses. J Am Acad Child Adolesc Psychiatry. 2007; 46: 1003-1014.

208. [0119/0120] Molina et al (2007): Molina B, Flory K, Hinshaw S, Greiner A, Arnold L, Swanson J, Hechtman L, Jensen P, Vitiello B, Hoza B, Pelham W, Elliott G, Wells K, Abikoff H, Gibbons R, Marcus S, Conners C, Epstein J, Greenhill L, March J, Newcorn J, Severe J, Wigal T. Delinquent behavior and emerging substance use in the MTA at 36 months: prevalence, course, and treatment effects. J Am Acad Child Adolesc Psychiatry. 2007; 46: 1028-1040.

209. [0119/0120] Molina et al (2009): Molina B, Hinshaw S, Swanson J, Arnold L, Vitiello B, Jensen P, Epstein J, Hoza B, Hechtman L, Abikoff H, Elliott G, Greenhill L, Newcorn J, Wells K, Wigal T, Gibbons R, Hur K, Houck P. The MTA at 8 years: Prospective follow-up of children treated for combined-type ADHD in a multisite study. J Am Acad Child Adolesc Psychiatry. 2009; 48: 484-500.

210. [0119/0120] Molina et al (2013): Molina B, Hinshaw S, Arnold L, Swanson J, Pelham W, Hechtman L, Hoza B, Epstein J, Wigal T, Abikoff H, Greenhill L, Jensen P, Wells K, Vitiello B, Gibbons R, Howard A, Houck P, Hur K, Lu B, Marcus S. Adolescent substance use in the Multimodal Treatment Study of ADHD (MTA) as a function of childhood ADHD, random assignment to childhood treatments, and subsequent medication. J Am Acad Child Adolesc Psychiatry. 2013; 52: 250-263.

211. [0119/0120] Swanson et al (2017): Swanson J, Arnold L, Molina B, et al. Young adult outcomes in the follow up of the multimodal treatment study of ADHD: symptom persistence, source discrepancy, and height suppression. *Journal of Child Psychology and Psychiatry.* 2017; 58: 663-678.

212. [0119/0120] MTA Group (1999b): MTA Cooperative Group. Moderators and mediators of treatment response for children with attention-deficit/hyperactivity disorder. Arch Gen Psychiatry. 1999. 56: 1088-1096.

213. [0119/0120] Swanson et al (2020): Swanson J for the MTA Group. Presentation at the CHADD Annual Meeting: 2020. Dallas Texas.

214. [0120/0121] Swanson et al (2017): Swanson J, Arnold L, Molina B, et al. Young adult outcomes in the follow up of the multimodal treatment study of ADHD: symptom persistence, source discrepancy, and height suppression. *Journal of Child Psychology and Psychiatry.* 2017; 58: 663-678.

215. [0120/0121] Swanson et al (2017): Swanson J, Arnold L, Molina B, et al. Young adult outcomes in the follow up of the multimodal treatment study of ADHD: symptom persistence, source discrepancy, and height suppression. *Journal of Child Psychology and Psychiatry.* 2017; 58: 663-678.

216. [0121/0122] Shaw et al (2012): Shaw M, Caci H, Kahle J, Woods A and Arnold L. A systematic review and analysis of long-term outcomes in attention deficit hyperactivity disorder. BMC Medicine, 2012, 10: 99-113.

217. [0121/0122] Arnold et al (2015): Arnold L, Hodgkins P, Caci H, Kahle J, and Young S. Effect of treatment modality in long-term outcomes in attention-deficit/hyperactivity disorder: A systematic review. PLOS One. 2015, 10:1-19.

218. [0122/0123] Gajria et al (2014): Gajria K, Mei, L, Sikirica V, Greven P, Zhong Y, Qin P, Xie J. Adherence, persistence, and medication discontinuation in patients with attention-deficit/hyperactivity disorder—a systematic literature review. Neuropsychiatric Disease and Treatment. 2014, 10: 1543-1569.

219. [0122/0123] Molina et al (2009): Molina B, Hinshaw S, Swanson J, Arnold L, Vitiello B, Jensen P, Epstein J, Hoza B, Hechtman L, Abikoff H, Elliott G, Greenhill L, Newcorn J, Wells K, Wigal T, Gibbons R, Hur K, Houck P. The MTA at 8 years: Prospective follow-up of children treated for combined-type ADHD in a multisite study. J Am Acad Child Adolesc Psychiatry. 2009; 48: 484-500.

220. [0122/0123] Molina and Swanson (2020): Molina B and Swanson J. Why Are Long-term Benefits of Stimulant Medication So Difficult to Detect? The ADHD Report, 2020. 28: 1-7.

221. [0122/0123] Swanson et al (1999): Swanson J, Gupta S, Guinta D, Flynn D, Agler D, Lerner M, Williams L, Shoulson I, Wigal, S. Acute tolerance to methylphenidate in the treatment of ADHD in children. Clin Pharmacol Ther. 1999; 66: 295-305.

222. [0122/0123] MTA Group (1999): MTA Cooperative Group. A 14-month randomized clinical trial of treatment strategies for attention deficit hyperactivity disorder. Arch Gen Psychiatry. 1999; 56: 1073-1086.

223. [0123/0124] Coghill et al (2021): Coghill D. et al, EAGG.

224. [0123/0124] Brinkman et al (2018): Brinkman W, Simon J, and Epstein J. Reasons Why Children and Adolescents with ADHD Stop and Restart Taking Medicine, Acad Pediatr. 2018; 18: 273-280.

225. [0124/0125] Swanson et al (2003): Swanson J, Gupta S, Lam A, Shoulson I, Lerner M, Modi N, Lindemulder E, Wigal S. Development of a new once-a-day formulation of methylphenidate for the treatment of ADHD: Proof-of-concept and proof-of-product studies. Arc Gen Psy. 2003; 60: 204-211.

226. [0124/0125] Greenhill et al (2001): Greenhill L, Swanson J, Vitiello B, Davies M, Clevenger W, Wu M, Arnold L, et al. Impairment and deportment responses to different methylphenidate doses in children with ADHD: the MTA titration trial. J Am Acad Child Adolesc Psychiatry. 2001, 40: 180-187.

227. [0124/0125] Vitiello et al (2001): Vitiello B, Severe J, Greenhill L, Arnold L, Abikoff H, Bukstein O, Elliott G, Hechtman L, Jensen P, Hinshaw S, March J, Newcorn J, Swanson J, and Cantwell D. Methylphenidate dosage for children with ADHD over time under controlled conditions: lessons from the MTA. J Am Acad Child Adolesc Psychiat. 2001; 40: 188-196.

228. [0124/0125] Greenhill et al (2006): Greenhill L, Kollins S, Abikoff H, McCracker J, Riddle M, Swanson J, McGough J, Wigal S, Wigal T, Vitiello B, Skrobala A, Posner K, Ghuman J, Cunningham S, Davies M, Chuang S, Cooper T. Efficacy and safety of immediate-release methylphenidate treatment for preschoolers with ADHD. J Am Acad Child Adolesc Psychiatry. 2006; 45: 1284-1293.

229. [0124/0125] Pliszka et al (2007): Pliszka S and AACAP Workgroup. Practice Parameter for the Assessment and Treatment of Children and Adolescents with ADHD. J Am Acad Child Adolesc Psychiatry, 2007, 46: 894-921.

230. [0124/0125] Atzori et al (2009): Atzori P, Usala T, Carucci S, Danjou F, and Zuddas A. Predictive factors for persistent use and compliance of immediate-release methylphenidate. Journal Child Adolescent Psychopharmacology, 2009; 19: 673-681.

231. [0124/0125] Coghill and Seth (2015): Coghill D and Seth S. Effective management of attention-deficit/hyperactivity disorder (ADHD) through structured re-assessment: the Dundee ADHD clinical care pathway. Child and Adolescent Psychiatry and Mental Health, 2015; 9: 52-65.

232. [0124/0125] Matthijssen et al (2019): Matthijssen A, Dietrich A, Bierens M, Deters R, van de Loo-Neus G, van den Hoofdakker B, Buitelaar J, and Hoekstra P. Continued Benefits of Methylphenidate in ADHD After 2 Years in Clinical Practice: A Randomized Placebo-Controlled Discontinuation Study, American Journal of Psychiatry, 2019; 176: 754-762.

233. [0124/0125] Swanson et al (2017): Swanson J, Arnold L, Molina B, et al. Young adult outcomes in the follow up of the multimodal treatment study of ADHD: symptom persistence, source discrepancy, and height suppression. *Journal of Child Psychology and Psychiatry.* 2017; 58: 663-678.

234. [0125/0126] Biederman et al (2010): Biederman, Mick E, Surman C, Doyle R, Hammerness P, Kotarski M, et al. A randomized, 3-phase, 34-week, double-blind, long-term efficacy study of osmotic-release oral system-methylphenidate in adults with attention-deficit/hyperactivity disorder. J. Clin. Psychopharmacol. 2010; 30, 549-553.

235. [0125/0126] Buitelaar et al (2012): Buitelaar J, Sobanski E, Stieglitz R., Dejonckheere J, Waechter S, and Schauble B. Predictors of placebo response in adults with attention-deficit/hyperactivity disorder: Data from 2 randomized trials of osmotic-release oral system methylphenidate. J. Clin. Psychiatry, 2012; 73: 1097-1102.

236. [0127/0128] Swanson et al (2002): Swanson J, Lerner M, Wigal T, Steinhoff K, Greenhill L, Posner K, Freid J, Wigal S. The use of a laboratory school protocol to evaluate concepts about efficacy and side effects of new formulations of stimulant medications. J Atten Disord. 2002; 6: S73-S88.

237. [0128/0129] Grace (2001): Grace A. Psychostimulant actions on dopamine and limbic system function: Relevance to the pathophysiology and treatment of ADHD. In M Solanto, A Arnsten, and F Castellanos (Editors): Stimulant Drugs and ADHD: Basic and Clinical Neuroscience. 2001; Oxford University Press: New York NY.

238. [0128/0129] Grace (2001): Grace A. Psychostimulant actions on dopamine and limbic system function: Relevance to the pathophysiology and treatment of ADHD. In M Solanto, A Arnsten, and F Castellanos (Editors): Stimulant Drugs and ADHD: Basic and Clinical Neuroscience. 2001; Oxford University Press: New York NY.

239. [0129/0130] Safer and Allen (1989): Safer D and Allen R. Absence of tolerance to the behavioral effects of methylphenidate in hyperactive and inattentive children. J Pediatrics. 1989; 115: 1003-1008.

240. [0129/0130] Greenhill and Osman (1991): Greenhill L. Methylphenidate in the Clinical Office Practice of Child Psychiatry. In L Greenhill and B Osman (Editors): Ritalin: Theory and Patient Management: 1991; Mary Ann Liebert: New York City, NY.

241. [0129/0130] Solanto (1998): Solanto M. Neuropsychopharmacological mechansims of stimulant drug action in ADHD: A review and integration. Behav Brain Res, 1998; 94: 127-152.

242. [0129/0130] Volkow et al (1995): Volkow D, Ding Y, Fowler J, Wang G-J, Logan J, Gatley J S, Dewey S, Ashby C, Liebermann J, Hitzemann R, et al. Is methylphenidate like cocaine? Studies on their pharmacokinetics and distribution in the human brain. Arch Gen Psychiatry, 1995; 52: 456-463.

243. [0129/0130] Grace (1995): Grace A. The tonic/phasic model of dopamine system regulation: Its relevance for understanding how stimulant abuse can alter basal ganglia function. Drug Alcohol Depend, 1995; 37: 111-129.

244. [0129/0130] Yano and Steiner (2007): Yano M and Steiner H. Methylphenidate and cocaine: the same effects on gene regulation? Trends in Pharmacological Sciences. 2007; 28: 588-596.

245. [0130/0131] Volkow et al (2007): Volkow N, Wang G, Newcorn J, Fowler J, Telang F, Solanto M, Logan J, Wong C, Ma Y, Swanson J, Schulz K, Pradhan K. Brain dopamine transporter levels in treatment and drug naïve adults with ADHD. NeuroImage. 2007; 34: 1182-1190.

246. [0130/0131] Wang et al (2013): Wang G-J, Volkow N, Wigal T, Kollins S, Newcorn J, Telang F, Logan J, Jayne M, Wong C, Han H, Fowler J, Zhu W, Swanson J. Long-term stimulant treatment affects brain dopamine transporter level in patients with attention deficit hyperactive disorder. PLoS One. 2013. 8: e63023

247. [0130/0131] Gill et al (2012): Gill K, Pierre P, Daunais J, Bennett A, Martelle S, Gage H, Swanson J, Nader M, and Porrino L. Chronic Treatment with Extended Release Methylphenidate Does Not Alter Dopamine Systems or Increase Vulnerability for Cocaine Self-Administration: A Study in Nonhuman Primates. Neuropsychopharmacology. 2012; 37: 2555-2565.

248. [0130/0131] Thanos et al (2010): Thanos P, Swanson J, Mary M, Janda H, Snearly C, Abrams W, Robison L, Ananth M, Wigal T, Hadjiargyrou M, Wang G-J, Volkow N, Komatsu D. Skeletal Deficits and Recovery in Methylphenidate Treated Rats. American College of Neuropsychopharmacology, 2010: Poster presentation.

249. [0132/0133] Pozzi et al (2020): Pozzi M, Bertella S, Gatti S, Peeters G, Carnovale C, Zambrano S and Nobile M. Emerging drugs for the treatment of attention-deficit hyperactivity disorder (ADHD), Expert Opinion on Emerging Drugs. 2020; 25:4, 395-407.

250. [0133/0134] Swanson et al (2002): Swanson J, Lerner M, Wigal T, Steinhoff K, Greenhill L, Posner K, Freid J, Wigal S. The use of a laboratory school protocol to evaluate concepts about efficacy and side effects of new formulations of stimulant medications. J Atten Disord. 2002; 6: S73-S88.

What is claimed is:

1. A method of treating or reducing, in a human being, carry-over tolerance of methylphenidate and emergence of accumulated tolerance of methylphenidate that undermines long-term efficacy of methylphenidate against attention-deficit/hyperactivity disorder (ADHD), the method comprising:

administering an immediate-release formulation of methylphenidate having effectiveness against ADHD, wherein methylphenidate causes acute tolerance to methylphenidate when administered daily as a once-a-day formulation with a drug delivery profile to maintain efficacy, wherein failure of the acute tolerance to methylphenidate to dissipate between daily administrations results in the carry-over tolerance which accumulates as the accumulated tolerance and emerges over time as long-term tolerance to methylphenidate; and administering an extended-release formulation of mazindol or modafinil that improves attention and wakefulness; wherein the mazindol or modafinil does not elicit acute tolerance to the mazindol or modafinil and allows the carry-over tolerance to the methylphenidate to dissipate fully each day;

wherein, when administered on a once-daily basis, administration of the methylphenidate in combination with the administration of the mazindol or modafinil treats ADHD or symptoms thereof without accumulating tolerance for the methylphenidate.

2. The method of claim 1, wherein the methylphenidate and the mazindol or modafinil are administered simultaneously.

3. The method of claim 1, wherein the methylphenidate and the mazindol or modafinil are administered at different times.

4. The method of claim 1, wherein the mazindol or modafinil is in a solid dosage form and the formulation of methylphenidate is in the form of a coating applied upon at least a part of an outer surface of the mazindol or modafinil.

5. The method of claim 1, wherein the methylphenidate and the mazindol or modafinil are contained in a capsule containing therein one or more first beads comprising the methylphenidate for immediate release and two or more second beads comprising the mazindol or modafinil for extended release.

6. A method of treating or reducing, in a human being, carry-over tolerance of methylphenidate and emergence of accumulated tolerance of methylphenidate that undermines long-term efficacy of methylphenidate, methylphenidate having effectiveness against attention-deficit/hyperactivity disorder (ADHD), the method comprising:

administering once daily to the human being a pharmaceutical composition in a single dosage form, the pharmaceutical composition comprising:

a first component comprising a dose of methylphenidate having effectiveness against ADHD, wherein methylphenidate causes acute tolerance to methylphenidate when administered daily as a once-a-day formulation with a drug delivery profile to maintain efficacy, wherein failure of the acute tolerance to methylphenidate to dissipate between daily administrations results in the carry-over tolerance which accumulates as the accumulated tolerance and emerges over time as long-term tolerance to methylphenidate; and a second component comprising a delayed-release formulation of mazindol or modafinil that improves attention and wakefulness, wherein the mazindol or modafinil does not elicit acute tolerance to the mazindol or modafinil and allows the acute tolerance to the methylphenidate to dissipate fully each day;

wherein when administered once daily, the pharmaceutical composition maintains effectiveness against ADHD and allows the accumulated tolerance to the methylphenidate to dissipate before the next daily administration without the carry-over tolerance to the methylphenidate, which maintains the efficacy of the methylphenidate during long-term treatment; and wherein administrating the pharmaceutical composition daily effectively treats ADHD symptoms for a similar time frame as the methylphenidate administered daily as the once-a-day formulation with the drug delivery profile.

7. The method of claim 6, wherein the dose of the methylphenidate comprises a bolus dose of the methylphenidate.

8. The method of claim 6, wherein the second component is a solid dosage form and the first component is in the form of a coating applied upon at least a part of an outer surface of the second component.

9. The method of claim 6, wherein the pharmaceutical composition is in the form of a capsule containing therein one or more first beads comprising the first component for immediate release and two or more second beads comprising the second component for extended release.

10. The method of claim 6, wherein the pharmaceutical composition is effective for a period of about 10 to 16 hours following administration.

11. A method of treating or reducing, in a human being, carry-over tolerance and/or tachyphylaxis of methylphenidate having effectiveness against ADHD and to prevent, in the human being, emergence of accumulated tolerance of methylphenidate that undermines long-term efficacy of methylphenidate the stimulant drug-against attention-deficit/hyperactivity disorder (ADHD), the method comprising:

administering once daily a pharmaceutical composition in a single dosage form, the pharmaceutical composition comprising:

a first component comprising a dose of methylphenidate, having the effectiveness against ADHD, wherein methylphenidate causes the carry-over tolerance and/or the tachyphylaxis when administered daily as a once-a-day formulation with a drug delivery profile to maintain efficacy; and a second component comprising a delayed-release formulation of mazindol or modafinil that improves attention and wakefulness, wherein the mazindol or modafinil does not elicit acute tolerance to the mazindol or modafinil and allows the carry-over tolerance and/or the tachyphylaxis to the methylphenidate to dissipate fully each day;

wherein when administered once daily, the pharmaceutical composition maintains effectiveness against ADHD and allows the carry-over tolerance and/or the tachyphylaxis to the methylphenidate to dissipate before the next daily administration without the carry-over tolerance and/or tachyphylaxis to the methylphenidate, which maintains the efficacy of the methylphenidate during long-term treatment.

12. The method of claim 11, wherein administrating the pharmaceutical composition daily effectively treats ADHD symptoms for a similar time frame as the methylphenidate administered daily as the once-a-day formulation with the drug delivery profile.

13. The method of claim 11, wherein the methylphenidate is delivered before the mazindol or modafinil, and wherein the dose of the methylphenidate has a pharmacodynamic half-life.

14. The method of claim 13 further comprising initiating delivery of the mazindol or modafinil within a window defined by a period of time beginning one hour before and ending one hour after the methylphenidate reaches its pharmacodynamic half-life.

15. The method of claim 11, wherein the mazindol or modafinil is a solid dosage form and the methylphenidate is in the form of a coating applied upon some or all of an outer surface of the mazindol or modafinil.

16. The method of claim 11, wherein the methylphenidate and the mazindol or modafinil are contained in a capsule containing therein one or more first beads comprising the methylphenidate for immediate release and two or more second beads comprising the mazindol or modafinil for extended release.

* * * * *